(12) United States Patent
Yu

(10) Patent No.: US 10,611,723 B2
(45) Date of Patent: Apr. 7, 2020

(54) LIGAND-ENABLED META-C-H ACTIVATION USING A TRANSIENT MEDIATOR

(71) Applicants: Jin-Quan Yu, San Diego, CA (US); The Scripps Research Institute, LaJolla, CA (US)

(72) Inventor: Jin-Quan Yu, San Diego, CA (US)

(73) Assignee: The Scripps Research Institute, LaJolla, CA (US)

( * ) Notice: Subject to any disclaimer, the term of this patent is extended or adjusted under 35 U.S.C. 154(b) by 0 days.

(21) Appl. No.: 15/547,014

(22) PCT Filed: Jan. 28, 2016

(86) PCT No.: PCT/US2016/015396
§ 371 (c)(1),
(2) Date: Jul. 27, 2017

(87) PCT Pub. No.: WO2016/123361
PCT Pub. Date: Aug. 4, 2016

(65) Prior Publication Data
US 2018/0009739 A1    Jan. 11, 2018

Related U.S. Application Data

(60) Provisional application No. 62/108,852, filed on Jan. 28, 2015.

(51) Int. Cl.
| | | |
|---|---|---|
| C07C 233/15 | (2006.01) |
| C07D 209/48 | (2006.01) |
| C07B 43/06 | (2006.01) |
| C07C 231/12 | (2006.01) |
| C07D 209/42 | (2006.01) |
| C07D 307/84 | (2006.01) |
| C07C 233/59 | (2006.01) |
| C07D 209/04 | (2006.01) |
| C07D 307/77 | (2006.01) |

(52) U.S. Cl.
CPC ............ *C07C 233/15* (2013.01); *C07B 43/06* (2013.01); *C07C 231/12* (2013.01); *C07C 233/59* (2013.01); *C07D 209/04* (2013.01); *C07D 209/42* (2013.01); *C07D 209/48* (2013.01); *C07D 307/77* (2013.01); *C07D 307/84* (2013.01); *C07C 2602/10* (2017.05)

(58) Field of Classification Search
None
See application file for complete search history.

(56) References Cited

PUBLICATIONS

Wihelm et al., *Org Lett* 7:4053-4056 (2005).
Dong et al., *J Am Chem Soc* 135:18350-18353 (2013).
Motti et al., *J Organomet Chem* 689:3741-3749 (2004).
Catellani et al, *Angew Chem Int Ed Engl* 36:119-122 (1997).
Leow et al., *Nature* 486:518-522 (2012).
Tang er al., *Nature* 507:215-220 (2014).
Wang et al., *Nature* 519:334-338 (Mar. 19, 2015).
WO 2016/015396 International Search Report.
WO 2016/015396 Written Opinion.
*C&EN* 27 (Mar. 16, 2015) ACS Publications, Washington, D.C.

*Primary Examiner* — Heidi Reese
(74) *Attorney, Agent, or Firm* — Husch Blackwell LLP

(57) ABSTRACT

An alternative approach to formation of a C—C bond at a meta-position of an aromatic compound is disclosed that employs an ethylenically unsaturated bicyclic compound as a transient mediator to achieve meta-selective C—H activation with a simple and common ortho-directing group. The use of a pyridine-based ligand assists in relaying the palladium catalyst to the meta-position by the unsaturated bicyclic compound following initial ortho-C—H activation.

15 Claims, No Drawings

LIGAND-ENABLED META-C-H ACTIVATION USING A TRANSIENT MEDIATOR

CROSS-REFERENCE TO RELATED APPLICATION

This application claims priority from provisional application No. 62/108,852 filed Jan. 28, 2016, whose disclosures are incorporated herein by reference.

GOVERNMENTAL SUPPORT

This invention was made with governmental support under NIGMS 1 RO1 GM102265 awarded by the National Institutes of Health. The government has certain rights in the invention.

BACKGROUND ART

Achieving site selectivity in C—H functionalization reactions is a significant challenge when the target C—H bonds are remote to existing functional groups. The development of a series of end-on templates has allowed for site-selective activation of remote meta-C—H bonds (more than 10 bonds away from the directing atom) [Leow et al., Nature 486, 518-522 (2012); Tang et al., Nature 507, 215-220 (2014); Lee et al., J. Am. Chem. Soc. 135, 18778-18781 (2013); Wan et al., J. Am. Chem. Soc. 135, 18056-18059 (2013); and Yang et al., J. Am. Chem. Soc. 136, 10807-10813 (2014)].

Coordination of a functional group to a metal catalyst is often a key driving force and control element in many important reactions including asymmetric hydrogenation [Brown, Chem. Soc. Rev. 22, 25-41 (1993)], epoxidation [Johnson et al., In Catalytic Asymmetric Synthesis, 2nd ed. (ed. Ojima, I.) 231-280 (John Wiley & Sons, Inc., Hoboken, 2005); and Li et al., Acc. Chem. Res. 46, 506-518 (2013)] and lithiation [Hartung et al., In Modern Arene Chemistry (ed. Astruc, D.) 330-367 (Wiley-VCH Verlag GmbH & Co. KGaA, Weinheim, 2004)]. Exploitation of this effect has permitted the development of a diverse range of directed C—H activation reactions [Lyons et al., Chem. Rev. 110, 1147-1169 (2010); Daugulis et al., Acc. Chem. Res. 42, 1074-1086 (2009); Engle et al., Acc. Chem. Res. 45, 788-802 (2012); Colby et al., Chem. Rev. 110, 624-655 (2010); and Wencel-Delord et al., Chem. Soc. Rev. 40, 4740-4761 (2011)].

However, these traditional C—H activation methods are limited to proximal C—H bonds that are spatially and geometrically accessible from the directing functional group. Development of meta-selective C—H functionalizations remains a significant challenge [Saidi et al., J. Am. Chem. Soc. 133, 19298-19301 (2011); Duong et al., Angew. Chem. Int. Ed. 50, 463-466 (2011); and Hofmann et al., J. Am. Chem. Soc. 135, 5877-5884 (2013)].

The inventor and co-workers recently developed a U-shaped template to overcome this constraint, which enables activation of remote meta-C—H bonds [Leow et al., Nature 486, 518-522 (2012); and Tang et al., Nature 507, 215-220 (2014)] illustrated schematically below. Although this Covalent Template Strategy for Remote C—H Activation

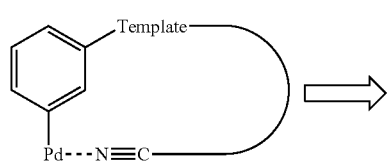

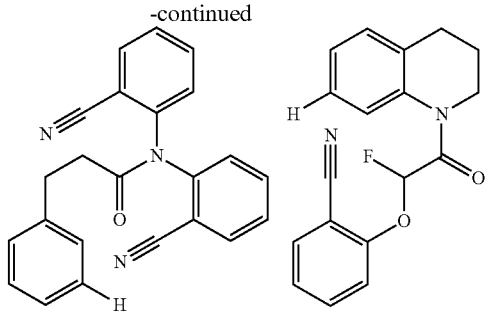

approach has proven applicable for a diverse set of substrates and catalytic transformations [Lee et al., J. Am. Chem. Soc. 135, 18778-18781 (2013); Wan et al., J. Am. Chem. Soc. 135, 18056-18059 (2013); and Yang et al., J. Am. Chem. Soc. 136, 10807-10813 (2014)], the need for a covalently attached complex template is a significant drawback for synthetic applications. Inspired by the unique reactivity of norbornene in palladium-catalyzed reactions discovered by Catellani and co-workers, below, [Catellani et al., Angew. Chem. Int.

Ortho-Alkylation and Ipso-Olefination in the Catellani Reaction

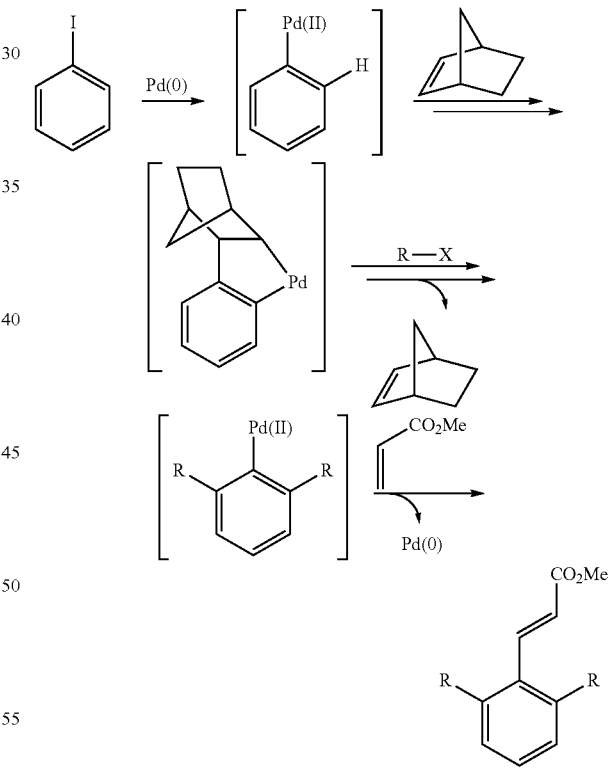

Ed. 36, 119-122 (1997); Faccini et al., J. Am. Chem. Soc. 126, 78-79 (2004); Martins et al., Top. Curr. Chem. 292, 1-33 (2010); Cardenas et al., J. Am. Chem. Soc. 128, 5033-5040 (2006); and Dong et al., J. Am. Chem. Soc. 135, 18350-18353 (2013)] it was hypothesized that ortho-palladacycle I could react with norbornene to provide an intermediate that can undergo activation of the meta-C—H bond (intermediate II), as shown below where $Ar_F$ is perfluorinated p-tolyl [4-$(CF_3)C_6F_4$].

Norbornene as a Transient Mediator for Meta-C—H Activation

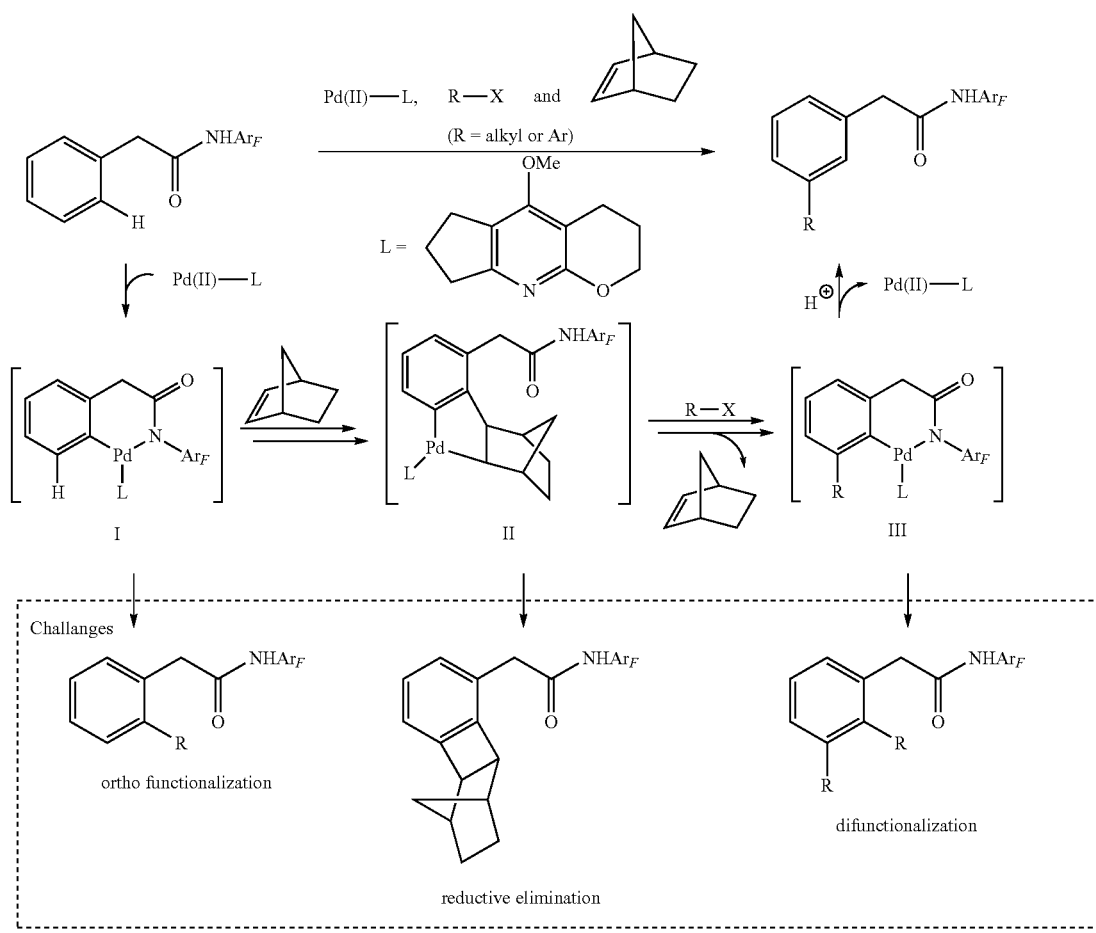

Reaction of palladacycle II with a coupling partner would form a new C—C or C-heteroatom bond and subsequent β-carbon elimination of norbornene followed by protodemetalation of the aryl-palladium bond would regenerate the palladium catalyst. As such, this reaction pathway would provide a new approach to achieve catalytic meta-selective C—H activation using standard ortho-directing groups with norbornene as a transient mediator.

The discussion that follows discloses the realization of this concept through the design of a pyridine-based ligand that suppresses several undesired reaction pathways and promotes meta-selective alkylation and -arylation of phenylacetic acid derivatives. This approach enables many previously reported ortho-C—H activation reactions to be achieved with high levels of meta-selectivity.

BRIEF SUMMARY OF THE INVENTION

The present invention contemplates a method of forming a carbon-to-carbon (C—C) bond at a position meta to a substituent previously present on the ring of an aromatic reactive substrate compound at the 1-position of the ring. This method comprises the steps of a providing a reaction mixture that contains i) the aromatic reactive substrate compound of Formula I dissolved or dispersed in a non-aqueous polar solvent having a boiling point at 1 atmosphere of about 100° to about 200° C., and further contains dissolved or dispersed therein ii) a catalytic amount of a Pd(II) catalyst, iii) a catalytic amount of pyridine or a substituted pyridine ligand, iv) an ethylenically unsaturated bicyclic compound of Formula II as a transient mediator present in excess over the amount of reactive substrate, v) about 1.5 to about 5 equivalents of an oxidant based on the amount of said reactive substrate, and vi) about 1.1 to about 10 equivalents of a reactive coupling agent. The reaction mixture is b) heated to a temperature of about 70° to about 120° C. and maintaining that temperature for a time period sufficient to carry out the C—C bond formation at a position meta to the 1-position substituent and form a reaction product. In that reaction mixture, the aromatic reactive substrate compound has a structural formula shown in Formula I, below:

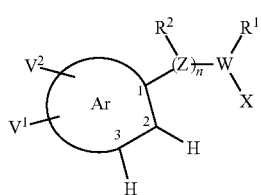

I wherein, the circled Ar is a heteroaromatic or is preferably a carbocyclic aromatic ring structure in which the bond shown to Z is at the 1-position of the ring and the substituent bonded at the 1-position constitutes the substituent previously present on the ring. The position rotated clock-wise from the 1-position is the 2- or ortho-position at which a hydrogen (H) is bonded. The next position clock-wise from position-2 at which another hydrogen (H) is bonded is the 3- or meta-position and is the position at which the new C—C bond is formed. The aromatic ring structure of Formula I contains a single ring, or two or three fused rings in which one ring contains 6 ring atoms and the other one or two rings independently contain 6 or 5 ring atoms, and in which a heteroaromatic ring structure contains one, two or three heteroatoms that can independently be nitrogen, oxygen or sulfur atoms. In formula I, n is zero (0) or one, such that Z and $R^2$ are absent when n is zero, and present when n is one. Z is O (oxygen), or C (carbon), such that when present as carbon, $R^2$ is $H_2$, HY, or $HR^3$, wherein Y is a protected hydroxyl or a protected amino group, and $R^3$ is a $C_1$-$C_{10}$-hydrocarbyl group that is straight, branched or includes a 4- to 6-membered ring bonded to a straight or branched chain, or $R^3$ together with the adjacent ring carbon atom, other than the ortho carbon noted above at the 2-position, and their associated atoms form a 5- or 6-membered aliphatic ring that can include one hetero atom in the ring that is O or protected N (nitrogen).

W is C (carbon) or N (nitrogen). When nitrogen, i) W is a ring atom of an aromatic ring system that contains at least one additional nitrogen atom that is adjacent to W in the aromatic ring, and can contain a third nitrogen ring atom or an oxygen ring atom, and ii) when W is carbon, a) W-X is a carbonyl group as discussed below, or b) W is the carbon of a >CH— group, or c) W, X and $R^1$ together form a heteroaromatic ring structure that contains one ring or two fused rings that each contains 5- or 6-members and a total of one to four heteroatoms that are independently nitrogen, oxygen or sulfur.

X is i) =O (oxo), ii) a nitrogen of an aromatic ring system formed with W, or iii) a N-sulfonamido or N-carboxamido group when W is the carbon of a >CH— group. $R^1$ is i) a perfluoro $C_1$-$C_{12}$-hydrocarbyl-amino group when W-X is carbonyl, or ii) together with the nitrogens of W and X forms an aromatic ring system that can contain a third nitrogen ring atom or an oxygen ring atom, or iii) is a $C_1$-$C_6$-hydrocarbyl carboxylate. $V^1$ and $V^2$ are the same or different substituents and are independently selected from the group consisting of hydrogen, halogen, a $C_1$-$C_6$-hydrocarbyl group, a perfluoro $C_1$-$C_6$-hydrocarbyl group and a $C_1$-$C_6$-hydrocarbyloxy group.

The transient mediator is an ethylenically unsaturated bicyclic compound of Formula II

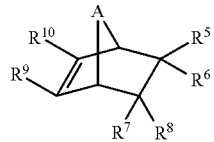

II wherein

A is $CH_2$, C=O or O, each of $R^5$, $R^6$, $R^7$, $R^8$, $R^9$, and $R^{10}$ is independently H, $C_1$-$C_6$-hydrocarbyl, $C_1$-$C_6$-hydrocarbyloxy, $C_1$-$C_6$-hydrocarbyl carboxylate, $C_1$-$C_6$-hydrocarboyl, one or both of $R^5$ plus $R^6$ and $R^7$ plus $R^8$ together with the carbon atom to which they are bonded form one or two carbonyl groups, or one each of $R^5$ and $R^6$, or $R^7$ and $R^8$ together with the atoms to which they are bonded form a further 4- to 6-membered aliphatic or aromatic ring that itself can be independently substituted with one or two substituent groups selected from the group consisting of a $C_1$-$C_6$-hydrocarbyl, a $C_1$-$C_6$-hydrocarbyloxy, a $C_1$-$C_6$-hydrocarbyl carboxylate and a nitro group.

In a preferred embodiment, one or both of $V^1$ and $V^2$ are other than hydrido. In other embodiments, Z is C, whereas in others W is C and X is =O, and preferably, $R^1$ is a 4-$(CF_3)C_6F_4NH$— group.

In still other preferred embodiments, $R^2$ is $H_2$, or HY, or $HR^3$.

In some preferred embodiments, the reactive coupling agent is an aromatic, benzylic or aliphatic bromide or iodide compound of the Formula $R^{15}$-Q, where $R^{15}$ is an aromatic group, a straight, branched or cyclic aliphatic $C_1$-$C_{10}$-hydrocarbyl group, or a benzylic group, and Q is bromo or iodo.

In a preferred embodiment, the transient mediator is a norbornene. A preferred pyridine or substituted pyridine ligand corresponds in structure to Formula L, below,

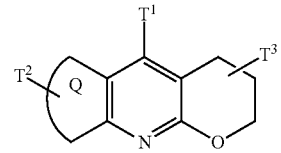

L where Q is a 5- or 6-membered ring that is aliphatic or aromatic; $T^1$ is hydrido, a $C_1$-$C_6$-hydrocarbyl group, a di-$C_1$-$C_6$-hydrocarbyl secondary amino group or the two hydrocarbyl groups along with the amine nitrogen atom forms a 5- or 6-membered ring that can contain an additional oxygen atom; and $T^2$ and $T^3$ are independently hydrido or the same or different $C_1$-$C_6$-hydrocarbyl group.

A contemplated method can include the further step of recovering the reaction product, although the reaction product can be left without recovery as a reactant in further reaction steps.

The present invention has several benefits and advantages.

One benefit is that it provides a new route to the preparation of meta-substituted aromatics that are either not possible to readily synthesize by other means or can be synthesized but require the presence of a chemically bonded directing ligand.

An advantage of the invention is that one can prepare meta-substituted aromatic compounds using aromatic reactive substrates whose substituent group(s) would usually direct a new C—C bond to an ortho position.

Another benefit of the invention is that the meta-directing ligand not being bonded to the aromatic substrate need not be removed by a separate reaction as compared to removal by physical separation.

Another advantage of the invention is that the desired products can often be prepared in yields that are greater than about 50%.

Still further benefits and advantages of the invention will be apparent to the skilled worker from the discussion that follows.

Definitions

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

The words "ortho", "meta" and "para" are used in their usual manner to describe benzenoid compounds that are substituted "1-2", "1-3" and "1-4", respectively. Those same words are also used herein as a convenience to describe those same substitution patterns in aliphatic compounds.

The word "hydrocarbyl" is used herein as a short hand term for a non-aromatic group that includes straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter.

Where a specific aliphatic hydrocarbyl substituent group is intended, that group is recited; i.e., $C_1$-$C_4$ alkyl, methyl or hexenyl. Exemplary hydrocarbyl groups contain a chain of 1 to about 7 carbon atoms, and preferably 1 to about 4 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl, octyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, n-propoxy, isopropoxy, allyloxy, n-butoxy, iso-butoxy, sec-butoxy, tert-butoxy, cyclohexenyloxy groups and the like. On the other hand, a hydrocarbyl group containing a —C(O)O— functionality is referred to as a hydrocarboyl (acyl) group inasmuch as there is no ambiguity in using that suffix. Exemplary hydrocarboyl and hydrocarboyloxy groups include acyl and acyloxy groups, respectively, such as acetyl and acetoxy, acryloyl and acryloyloxy.

As a skilled worker will understand, a substituent that cannot exist such as a $C_1$ alkenyl group is not intended to be encompassed by the word "hydrocarbyl", although such substituents with two or more carbon atoms are intended.

A "carboxyl" substituent is a —C(O)OH group. A $C_1$-$C_6$ hydrocarbyl carboxylate is a $C_1$-$C_6$ hydrocarbyl ester of a carboxyl group [—C(═O)—O—$C_1$-$C_6$ hydrocarbyl].

The term "aryl", alone or in combination, means a phenyl or naphthyl or other aromatic radical. An aryl group can be carbocyclic, containing only carbon atoms in the ring(s) or heterocyclic as a heteroaryl group discussed hereinafter. A "heteroaryl" group is an aromatic heterocyclic ring substituent that preferably contains one, or two, up to three or four, atoms in the ring other than carbon. Those heteroatoms can be nitrogen, sulfur or oxygen. A heteroaryl group can contain a single 5- or 6-membered ring or a fused ring system having two 6-membered rings or a 5- and a 6-membered ring. Exemplary heteroaryl groups include 6-membered ring substituents such as pyridyl, pyrazyl, pyrimidinyl, and pyridazinyl; 5-membered ring substituents such as 1,3, 5-, 1,2,4- or 1,2,3-triazinyl, imidazyl, (uranyl, thiophenyl, pyrazolyl, oxazolyl, isoxazolyl, thiazolyl, 1,2,3-, 1,2,4-, 1,2, 5-, or 1,3,4-oxadiazolyl and isothiazolyl groups; 6-/5-membered fused ring substituents such as benzothiofuranyl, isobenzothiofuranyl, benzisoxazolyl, benzoxazolyl, purinyl and anthranilyl groups; and 6-/6-membered fused rings such as 1,2-, 1,4-, 2,3- and 2,1-benzopyronyl, quinolinyl, isoquinolinyl, cinnolinyl, quinazolinyl, and 1,4-benzoxazinyl groups.

The term "halogen" means fluorine, chlorine or bromine. The term perfluorohydrocarbyl means a hydrocarbyl group wherein each hydrogen is replaced by a fluorine atom. Examples of such perfluorohydrocarbyl groups, in addition to trifluoromethyl, which is preferred, are perfluorobutyl, perfluoroisopropyl, perfluorododecyl and perfluorodecyl.

The terms "amino-protecting group" and "amine-protecting group" as used herein refer to one or more selectively removable substituents on the amino group commonly employed to block or protect the amino functionality. Examples of such amine-protecting groups include the formyl ("For") group, the trityl group ("Trt"), the phthalimido group ("Phth"), the trichloroacetyl group, the chloroacetyl, bromoacetyl, and iodoacetyl groups. Urethane blocking groups, such as t-butoxy-carbonyl ("Boc"), 2-(4-biphenylyl)propyl-(2)oxycarbonyl ("Bpoc"), 2-phenylpropyl(2)oxycarbonyl ("Poc"), 2-(4xenyl)-isopropoxycarbonyl, 1,1-diphenyl-ethyl(1)oxycarbonyl, 1,1-diphenylpropyl(1)-oxycarbonyl, 2-(3,5-dimethoxyphenyl) propyl(2)oxycarbonyl ("Ddz"), 2-(p-5-toluyl)-propyl(2) oxycarbonyl, cyclopentanyl-oxycarbonyl, 1-methylcyclopentanyloxycarbonyl, cyclohexanyloxycarbonyl, 1-methylcyclohexanyl-oxycarbonyl, 2-methylcyclohexanyloxycarbonyl, 2-(4-toluylsulfonyl) ethoxycarbonyl, 2-(methyl-sulfonyl)-ethoxycarbonyl, 2-(triphenylphosphino)-ethoxy-carbonyl, 9-fluoroenylmethoxycarbonyl ("Fmoc"), 2-(trimethyl-silyl)ethoxycarbonyl, allyloxycarbonyl, 1-(trimethyl-silylmethyl)prop-1-enyloxycarbonyl, 5-benzisoxalyl-methoxycarbonyl, 4-acetoxybenzyloxycarbonyl, 2,2,2-trichloro-ethoxycarbonyl, 2-ethynyl (2) propoxy-carbonyl, cyclopropylmethoxycarbonyl, isobornyloxycarbonyl, 1-piperidyloxycarbonyl, benzyloxycarbonyl ("Z"), 4-phenylbenzyloxycarbonyl, 2-methylbenzyloxy-carbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chloro-benzyloxycarbonyl, 2-chlorobenzyloxycarbonyl, dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxy-carbonyl, and the like, the benzoylmethylsulfonyl group, dithiasuccinoyl ("Dts') group, the 2-(nitro)-phenylsulfenyl group ("Nps"), the 2- or 4-nitro-phenylsulfonyl ("Nos") group, 4-toluenesulfonyl ("Ts"), the diphenylphosphine oxide group, and like amino-protecting groups.

The species of amine-protecting group employed is usually not critical so long as the derivatized amino group is stable to the conditions of the subsequent reactions and can be removed at the appropriate point without disrupting the remainder of the compound. A preferred amine-protecting group is a phthalimido group.

Further examples of amino-protecting groups embraced to, by the above term are well known in organic synthesis and the peptide art and are described by, for example: T. W. Greene and P. G. M. Wuts, *Protective Groups in Organic Synthesis*, 2nd ed., John Wiley and Sons, New York. N.Y., Chapter 7, 1991; M. Bodanzsky, *Principles of Peptide Synthesis*, 1st and 2nd revised ed., Springer-Verlag, New York, N.Y., 1984 and 1993; and Stewart and Young, *Solid Phase Peptide Synthesis*, 2nd ed., Pierce Chemical Co, Rockford, Ill. 1984.

The related term "protected amino" or "protected amine" defines an amino group substituted with an amino-protecting group discussed above.

The terms "hydroxy-protecting group" and "hydroxyl-protecting group" refer to readily cleavable groups bonded to hydroxyl groups, such as the tetrahydropyranyl, 2-methoxyprop-2-yl, 1-ethoxyeth-1-yl, methoxymethyl, methylthiomethyl, β-methoxyethoxymethyl, t-butyl, t-amyl, trityl, 4-methoxytrityl, 4,4'-dimethoxytrityl, 4,4',4''-trimethoxytrityl, benzyl, allyl, trimethylsilyl ("TMS"), t-butyldiphenylsilyl ("TBDPS"), (t-butyl)dimethylsilyl ("TBS" or "TBDMS"), triisopropylsilyl ("TIPS"), and 2,2,2-trichloro-ethoxycarbonyl groups, and the like. Ester groups such as $C_1$-$C_6$-hydrocarboyl esters such as acetate ("OAc"), propionate and hexanoate are also useful, as is a benzyl ether ("Bn") group. The species of hydroxyl-protecting groups is also usually not critical so long as the derivatized (protected) hydroxyl group is stable to the conditions of subsequent reaction(s) and the protecting group can be removed at the appropriate point without disrupting the remainder of the compound.

Further examples of hydroxy-protecting groups are described by C. B. Reese and E Haslam, *Protective Groups in Organic Chemistry*, J. G. W. McOmie Ed., Plenum Press, New York, N.Y., Chapters 3 and 4, 1973, and T. W. Greene and P. G. M. Wuts, *Protective Groups in Organic Synthesis*, 2nd ed., John Wiley and Sons, New York, N.Y., Chapters 2 and 3, 1991.

DETAILED DESCRIPTION OF THE INVENTION

The present invention contemplates a method of forming a carbon-to-carbon bond [C—C] at a position meta to a substituent previously present on the ring of an aromatic molecule that is referred to herein as a substrate. The structural formula of a contemplated reactive substrate molecule is shown in Formula I, below.

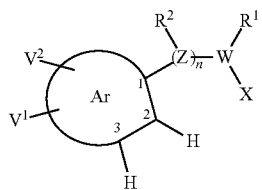

I

In a compound of Formula I, the circled Ar is an aromatic (heteroaromatic or carbocyclic aromatic) ring structure in which the bond shown to "Z" is deemed to be at the 1-position of the ring and constitutes the above substituent previously present on the ring. The position rotated clockwise from the 1-position is the 2- or ortho-position at which a hydrogen (H) is bonded. The next position clock-wise from position-2 at which another hydrogen (H) is bonded is the 3- or meta-position and is the position at which the new C—C bond is formed. (Positions 1, 2 and 3 within the Ar ring are numbered as such for convenience.) A contemplated aromatic ring structure can contain a single ring, one or two fused rings in which one ring contains 6 ring atoms and the other two or three rings independently contain 6 or 5 ring atoms. A heteroaromatic ring structure can contain one, two or three heteroatoms that can independently be nitrogen, oxygen or sulfur atoms.

In Formula I:

n is zero (0) or one, such that Z and $R^2$ are absent when n is zero, and present when n is one.

Z is O (oxygen), or C (carbon), such that $R^2$ is absent when Z is O, and when present, $R^2$ is $H_2$, HY, or $HR^3$, wherein Y is a protected hydroxyl or a protected amino group, and $R^3$ is a $C_1$-$C_{10}$-hydrocarbyl group that is straight, branched or includes a 4- to 6-membered ring bonded to a straight or branched chain, or $R^3$ together with the adjacent ring carbon atom other than the ortho carbon noted above at the 2-position and their associated atoms forms a 5- or 6-membered aliphatic ring that can include one hetero atom in the ring that is O or protected N (nitrogen).

W is C (carbon) or N (nitrogen), wherein when nitrogen, W is a ring atom of an aromatic ring system that contains at least one additional nitrogen atom that is adjacent to W in the aromatic ring, and can contain a third nitrogen ring or a ring oxygen atom. When W is carbon, a) W-X is a carbonyl group as discussed below, or b) W is a carbon of a >CH— group, or c) W, X and $R^1$ together form a heteroaromatic ring structure that contains one ring or two fused rings that each contains 5- or 6-members and a total in that ring structure of one to four heteroatoms that are independently nitrogen, oxygen or sulfur.

X is i) =O (oxo), ii) a nitrogen of an aromatic ring system formed with W, or iii) a N-sulfonamido [—NHS(O)$_2$—] or N-carboxmido [—NHC(O)—] group when W is the carbon of a >CH— group. In some preferred embodiments, W is C and X is =O so that W-X is a carbonyl group (C=O). In other preferred embodiments, where W is the carbon of a >CH— group, X is N-sulfonamido or carboxamido group and $R^1$ is a $C_1$-$C_6$-hydrocarbyl carboxylate.

$V^1$ and $V^2$ are the same or different substituents and are independently selected from the group consisting of hydrogen (hydrido), halogen (fluoro, chloro or bromo), a $C_1$-$C_6$-hydrocarbyl group, a perfluoro $C_1$-$C_6$-hydrocarbyl group and a $C_1$-$C_6$-hydrocarbyloxy group. Thus, if one or both of $V^1$ and $V^2$ are other than hydrido, one or two of the named substituents is present.

A reactive substrate compound of Formula I is present in a reaction mixture dissolved or dispersed in a comprises a non-aqueous polar solvent having a boiling point at 1 atmosphere of about 100° to about 200° C. that further contains dissolved or dispersed therein a) a catalytic amount of a Pd(II) catalyst, b) a catalytic amount of pyridine or a substituted pyridine ligand, c) an ethylenically unsaturated bicyclic compound of Formula II as a transient mediator present in excess over the amount of reactive substrate, d) about 1.5 to about 5 equivalents of an oxidant, and e) about 1.1 to about 10 equivalents of a coupling agent, a second reactant, that is typically an aliphatic or aromatic halide, preferably an iodide or bromide. The reaction mixture is heated and maintained at a temperature of about 70° to about 120° C. for a time period sufficient to carry out the insertion (C—O bond formation) and form a reaction product.

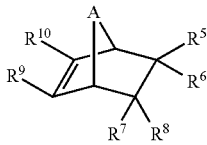

In Formula II of the transient mediator ethylenically unsaturated bicyclic compound, A is $CH_2$ (methylene), C=O (carbonyl) or O (oxygen).

Each of $R^5$, $R^6$, $R^7$, $R^8$, $R^9$, and $R^{10}$ is independently H (hydrido), $C_1$-$C_6$-hydrocarbyl, $C_1$-$C_6$-hydrocarbyloxy, $C_1$-$C_6$-hydrocarbyl carboxylate [—C(=O)O—$C_1$-$C_6$], $C_1$-$C_6$-hydrocarboyl, one or both of $R^5$ plus $R^6$ and $R^7$ plus $R^8$ together with the carbon atom to which they are bonded form one or two carbonyl (C=O) groups, or one each of $R^5$ and $R^6$, or $R^7$ and $R^8$ together with the atoms to which they are bonded form a further 4- to 6-membered aliphatic or aromatic ring that itself can be independently substituted with one or two substituent groups selected from the group consisting of a $C_1$-$C_6$-hydrocarbyl, a $C_1$-$C_6$-hydrocarbyloxy, a $C_1$-$C_6$-hydrocarbyl carboxylate and a nitro group. A $C_1$-$C_6$-hydrocarbyl, $C_1$-$C_6$-hydrocarbyloxy, $C_1$-$C_6$-hydrocarbyl carboxylate or $C_1$-$C_6$-hydrocarboyl portion of a substituent preferably contains one or two carbon atoms.

Illustrative transient mediator ethylenically unsaturated bicyclic compounds are shown below.

Illustrative Transient Mediator Compounds

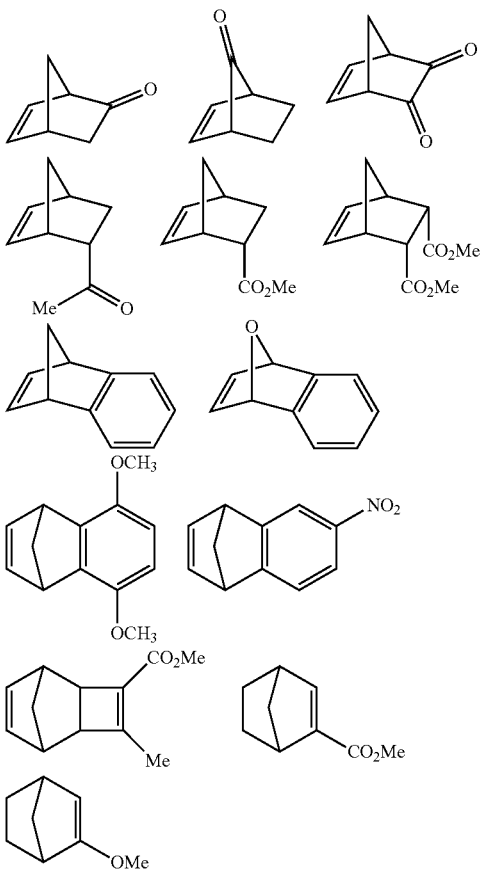

A contemplated coupling agent is typically an aromatic, benzylic or aliphatic bromide or iodide compound. A contemplated coupling agent can consequently be described as a $R^{15}$-Q compound in which $R^{15}$ is an aromatic (phenyl or naphthyl) group, a straight, branched or cyclic aliphatic $C_1$-$C_{10}$-hydrocarbyl group, or a benzylic group, and Q is bromo or iodo.

Illustrative aliphatic compounds include an iodo-substituted $C_1$-$C_{10}$-hydrocarbyl group that is straight, branched or cyclic such as methyl iodide and ethyl iodide whose use are illustrated herein. Another contemplated coupling agent is a benzyl halide such as benzyl bromide. The phenyl ring of a benzyl halide coupling agent can have one or two substituent groups $R^{16}$ and $R^{17}$ that are the same or different and independently selected from the group consisting of hydrido, a $C_1$-$C_6$-hydrocarbyl group, a halo (fluoro, chloro or bromo) group, a $C_1$-$C_6$-hydrocarboyl group and a perfluoro $C_1$-$C_6$-hydrocarbyl group. An aromatic iodide contains an aromatic ring can itself be further substituted with one or two substituent groups $R^{18}$ and $R^{19}$ that are the same or different and independently selected from the group consisting of hydrido, a $C_1$-$C_6$-hydrocarbyl group, a halo (fluoro, chloro or bromo) group, a $C_1$-$C_6$-hydrocarboyl group, a perfluoro $C_1$-$C_6$-hydrocarbyl group and a $C_1$-$C_6$-hydrocarboyloxy carboxylate group.

Useful Pd(II) catalysts are well known in the art. Exemplary catalysts include $PdCl_2$, $Pd(TFA)_2$, $Pd(PiV)_2$, $[PdCl(C_3H_5)]_2$, $PdCl_2(PPh_3)_2$, $Pd(PPh_3)_4$, $Pd_2(dba)_3$, $[PdCl_2(MeCN)_2]$, $[Pd(OTf)_2·4MeCN]$, and $[Pd(BF_4)_2·4MeCN]$. Of these catalysts, $Pd(TFA)_2$, $Pd(Piv)_2$ and $Pd(OAc)_2$ are presently preferred. A contemplated catalyst is utilized in a catalytic amount. That amount is typically about 5 to about 40 mole percent based on the moles of reactive substrate, and more preferably about 10 to about 30 mole percent.

Pyridine or a substituted pyridine ligand is typically present in the reaction composition at about 10 to about 50 mole percent based on the moles of reactive substrate. Preferably, the ligand is present at about 20 to about 40 mole percent. An exemplary pyridine derivative corresponds in structure to Formula L, below,

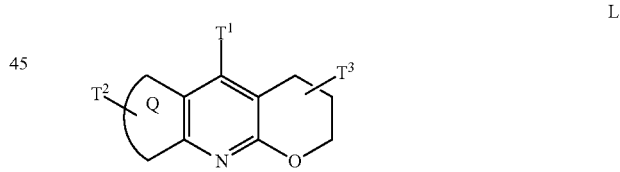

wherein

Q is a 5- or 6-membered ring that is aliphatic or aromatic.

$T^1$ is hydrido, a $C_1$-$C_6$-hydrocarbyl group or a di-$C_1$-$C_6$-hydrocarbyl secondary amino group or the two hydrocarbyl groups along with the amine nitrogen atom forms a 5- or 6-membered ring that can contain an additional oxygen atom.

$T^2$ and $T^3$ are independently hydrido or the same or different $C_1$-$C_6$-hydrocarbyl group.

As is seen hereinafter, the structure of a pyridine derivative ligand can be extremely varied. Substituted monocyclic, bicyclic and tricyclic derivatives are all useful. A tricyclic compound in which the pyridyl ring is substituted with a methoxy group at the 4-position and fused on one side to form a 6-membered oxygen-containing ring and fused on the other side to form a 5-membered carbocyclic ring that is referred to herein as ligand L19 is particularly preferred.

A contemplated method utilizes an excess, about 1.5 to about 5 equivalents (moles) of an oxidant per mole of reactive substrate, and preferably about 2 to about 4 equivalents of oxidant. A silver oxidant is typically used, although oxygen and other mild oxidants can also be used.

Illustrative catalysts include Ag(Piv), Ag(OAc), Ag$_2$O, AgTFA, AgOTf, Ag$_2$CO$_3$,

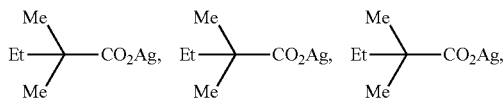

and Cu(OAc)$_2$. Ag(OAc) is a preferred oxidant.

A contemplated reaction is carried out with the ingredients dissolved or dispersed in a solvent and with agitation as can be provided by the use of a magnetic stir bar. Additional means of agitation such as shaking can also be utilized. Exemplary solvents include $^t$BuCO$_2$Me, hexafluoro-isopropanol (HFIP), $^t$BuCN, $^t$BuOMe, t-amylOH, $^t$Bu(C=O)Me, n-hexane, C$_6$F$_6$, dichloromethane (DCM), and 1,2-dichloroethane (DCE). DCE, t-amylOH and HFIP are preferred among these materials.

A contemplated method is preferably carried out under anhydrous conditions. A bench-scale reaction using about 0.05 to about 0.10 mmoles of reactive substrate and appropriate amounts of other ingredients is typically carried out in about 0.5 to about 3 mL of solvent. Larger quantities can be readily scaled from those proportions.

A reaction mixture formed in carrying out a method of the invention is maintained at a temperature of about 70° to about 120° C., and preferably at a temperature of about 90° to about 110° C., for a time period sufficient to carry out the electrophilic insertion and form a reaction product. More preferably, that temperature is about 80° to about 100° C. Reaction times are typically about 15 to about 50 hours, with times of about 18-30 hours being usual.

A contemplated reaction is preferably carried out in a sealed reaction vessel, so the pressure under which the ingredients are maintained is mostly that created by the solvent used, with some contribution from the reactants, at the reaction temperature. Upon completion of the reaction, the desired product can be recovered by usual work-up procedures, or can be left in situ and reacted further as desired.

It is also to be noted that the addition product of the transient mediator and the reactive substrate, a benzocyclobutane, can usually be recovered in high yield after a reaction time of about 2 to about 5 hours when the coupling agent is omitted from the reaction mixture. Lower yields of benzocyclobutane are typically obtained along with increasing yields of a desired meta-insertion product in the presence of the coupling agent.

Results and Discussion

It was possible that the above-proposed meta-C—H activation with norbornene as a transient mediator would face several key challenges. First, it was unclear if 1,2-migratory insertion with norbornene could occur from a cyclopalladated intermediate (I) and whether this pathway would be faster than the competitive reaction of the palladacycle with a terminal electrophile. In a recent report from the Bach's group, the C2-selective C—H alkylation of indoles via the initial aminopalladation of norbornene with the indolyl N—H bonds was inspiring. [Jiao et al., J. Am. Chem. Soc. 133, 12990-12993 (2011); and Jiao et al., J. Am. Chem. Soc. 134, 14563-14572 (2012)] Second, the resultant intermediate II could undergo reductive elimination to form a benzocyclobutene thereby preventing the desired meta-C—H functionalization. [Catellani et al., Synthesis 769-772 (1996)] Third, rather than undergoing protodemetalation, intermediate III could be further functionalized to afford the undesired ortho,meta-difunctionalized products.

This investigation was initiated with a phenylacetic acid-derived N-2,3,5,6-tetrafluoro-4-trifluoromethylphenyl amide reactive substrate. This auxiliary has been proven effective in the ortho-C—H activation of C(sp$^2$)-H bonds by Pd(II) catalysts. [Engle et al., Acc. Chem. Res. 45, 788-802 (2012)]

To probe the feasibility of each step in the proposed catalytic cycle, reactive substrate Compound 1a was first treated with Pd(OAc)$_2$ and norbornene under various conditions in an attempt to identify conditions for 1,2-migratory insertion without success (as is discussed hereinafter). Although, ortho-C—H activation of Compound 1a does not require ligands [Wang et al., J. Am. Chem. Soc. 135, 10326-10329 (2013)], the recent finding that 9-methylacridine promotes directed ortho-C—H activation [Zhu et al., J. Am. Chem. Soc. 136, 13194-13197 (2014)] prompted a search for pyridine-type ligands that would facilitate the 1,2-migratory insertion.

It was found that the addition of pyridine as a ligand enables 1,2-migratory insertion of norbornene into the putative ortho-palladacycle intermediate. Subsequent meta-C—H palladation and reductive elimination presumably then took place to give benzocyclobutene Compound 2a in 61% yield (below). Notably, formation of Compound 2a was not observed in the absence of pyridine ligand.

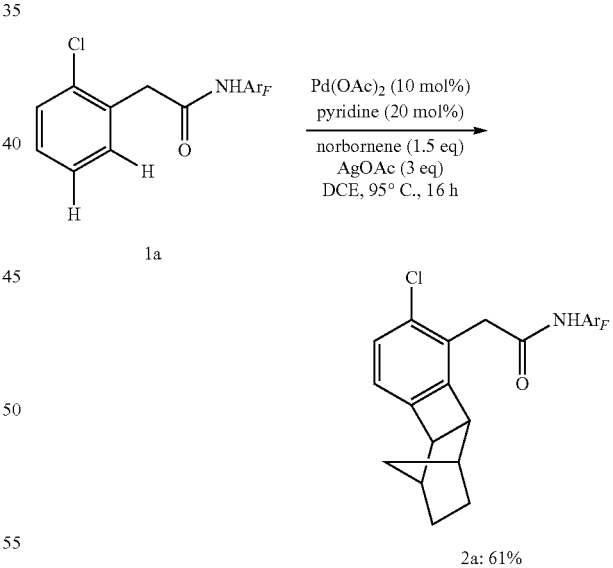

Having established the first step in the proposed catalytic cycle (1,2-migratory insertion), conditions to prevent benzocyclobutene formation and promote meta-functionalization with an electrophile were sought. Encouragingly, in the presence of methyl iodide, the desired meta-methylated product Compound 3a was obtained in 15% yield, and formation of Compound 2a was reduced to 15% yield (below; L1=pyridine).

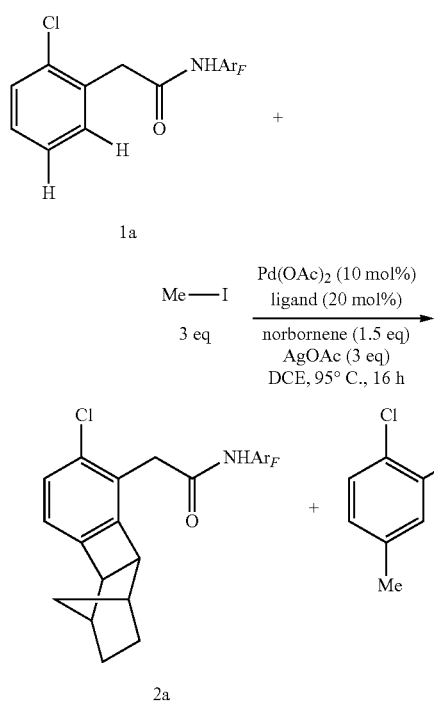

1a

Pd(OAc)$_2$ (10 mol%)
ligand (20 mol%)
Me—I  →
3 eq   norbornene (1.5 eq)
       AgOAc (3 eq)
       DCE, 95° C., 16 h 2a     3a Further screening of simple pyridine ligands revealed that alkyl substitution at the 2-position improved the yield of meta-methylation (L2 and L5, 29% and 37% yield, respectively). It was further found that pyridine ligands with electron-donating substituents lead to improved product selectivity (L6-L9), whereas electron-deficient pyridine ligands provided both poor selectivity and reactivity (L10-L12). These ligands and their product yields of Compound 2a and Compound 3a are shown below.

no ligand no reaction

L1

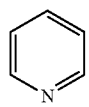

2a: 15%;
3a: 15%

L2

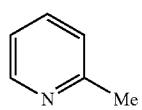

2a: 16%;
3a: 29%

L3

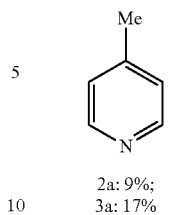

2a: 8%;
3a: 13%

L4

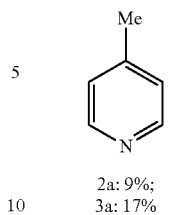

2a: 9%;
3a: 17%

L5

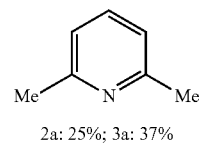

2a: 25%; 3a: 37%

L6

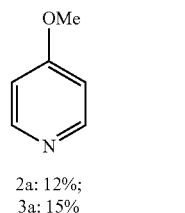

2a: 12%;
3a: 15%

L7

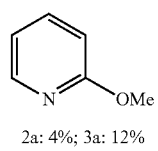

2a: 4%; 3a: 12%

L8

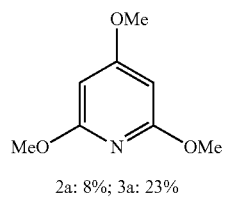

2a: 8%; 3a: 23%

L9

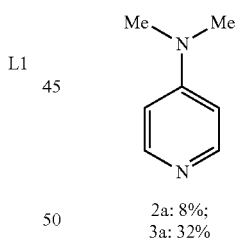

2a: 8%;
3a: 32%

L10

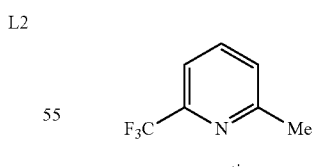

no reaction

L11

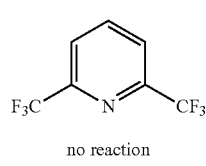

no reaction

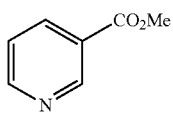

L12

2a: 8%; 3a: 9%

Prompted by recent progress in developing quinoline-based ligands for C—H activation [He et al., *Science* 343, 1216-1220 (2014); and Li et al., *J. Am. Chem. Soc.* 136, 5267-5270 (2014)], that class of ligands was also examined. Although the use of quinoline (L13), 2-methylquinoline (L14) and acridine (L15) as ligands led to increased reactivity, formation of benzocyclobutene Compound 2a was favored for L14 and L15, as shown below.

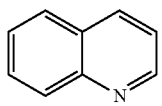

L13

2a: 22%; 3a: 30%

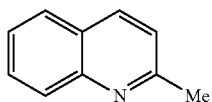

L14

2a: 51%; 3a: 28%

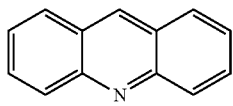

L15

2a: 58%; 3a: 28%

Because electron-donating substituents enhance selectivity for the meta-methylation pathway, several quinoline ligands containing alkoxy groups at the 2-position were examined, as shown below. Although 2-(isobutoxy)quinoline (L16) is an ineffective ligand, the use of ligand L17, containing a 2-alkoxy group with a constrained conformation in a fused ring, led to full conversion, affording Compound 3a in 80% yield. Installation of a highly electron-donating amine substituent on a similar ligand L18 did not improve the selectivity. Ligand L19, containing a fused cyclopentane ring, further improved the selectivity for meta-methylation, providing Compound 3a in 85% yield.

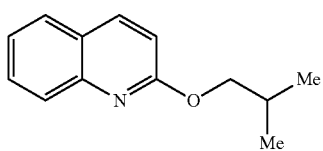

L16

2a: 3%; 3a: 13%

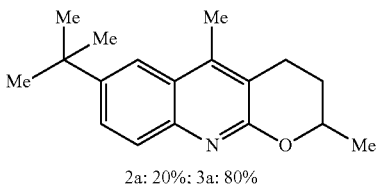

L17

2a: 20%; 3a: 80%

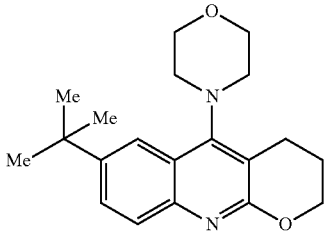

L18

2a: 20%; 3a: 80%

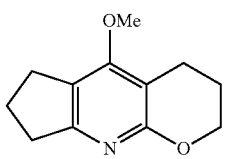

L19

2a: 15%; 3a: 85%
(80% isolated yield)

Selective meta-alkylation with ethyl iodoacetate as coupling partner is also achieved under optimized conditions to give the desired product Compound 4a in 67% yield as shown below.

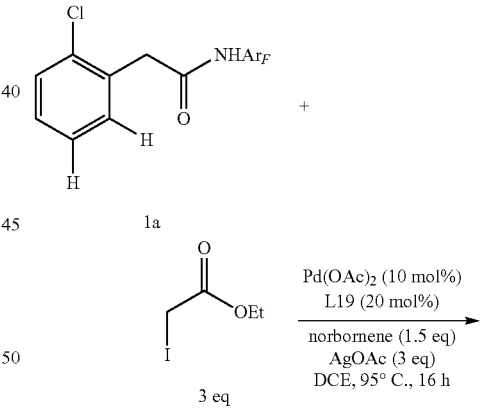

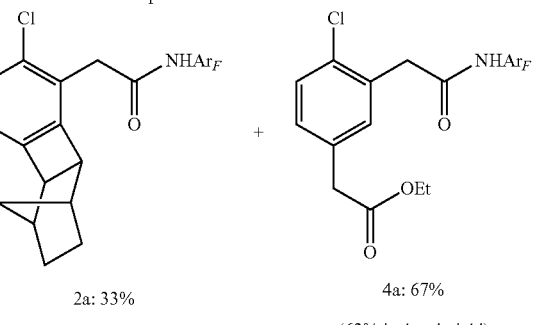

2a: 33%

4a: 67%
(63% isolated yield)

Yields were determined by crude $^1$H NMR analysis.

The scope of this norbornene-mediated meta-alkylation was investigated using methyl iodide (Compounds 3a-3x) and ethyl iodoacetate (Compounds 4a-4x) as coupling partners with ligand L19 in the reaction shown schematically below. Results of these studies are discussed and shown thereafter. In the structures shown above and those below, R—I=methyl iodide or ethyl iodoacetate; X, Y=generic substituents; Ac=acetyl; Bn=benzyl; Phth=phthaloyl; Ts=4-toluenesulfonyl.

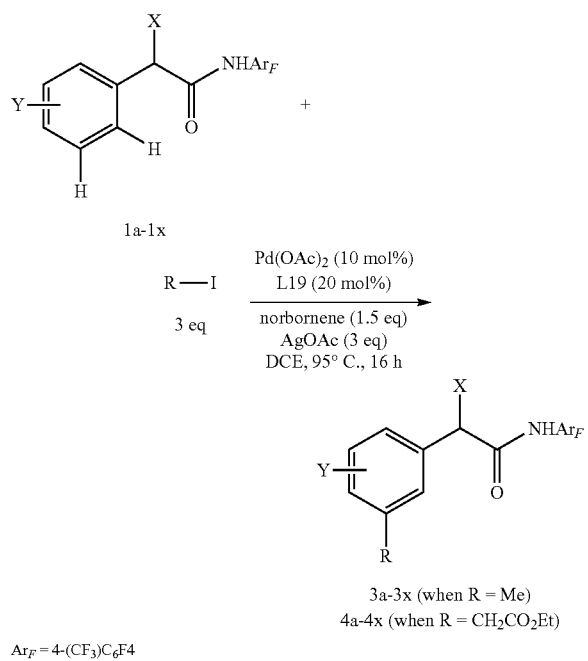

Ar$_F$ = 4-(CF$_3$)C$_6$F$_4$

Electron-donating and -withdrawing ortho-substituents are tolerated in this transformation, providing moderate to excellent yields (Compounds 3a-3h and 4a-4h). An ortho-bromide substituent is also compatible with this protocol (Compounds 3d and 4d). Results for production of Compounds 3g,h and 4g,h were obtained using 15 mol % Pd(OAc)$_2$ and 30 mol % L19.

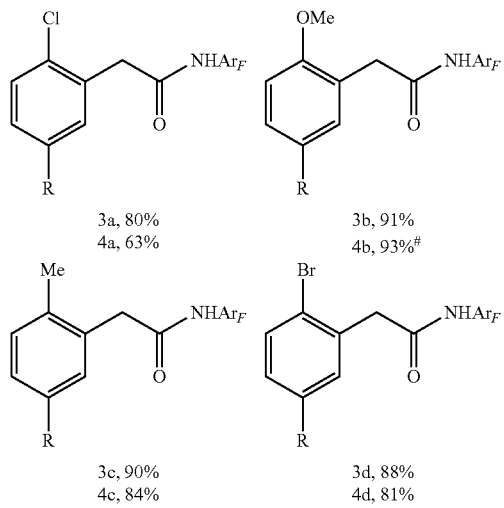

3a, 80%
4a, 63%

3b, 91%
4b, 93%#

3c, 90%
4c, 84%

3d, 88%
4d, 81%

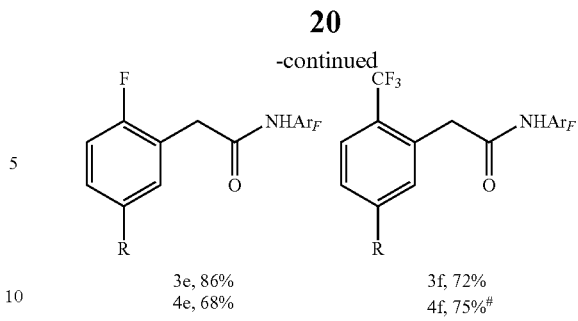

3e, 86%
4e, 68%

3f, 72%
4f, 75%#

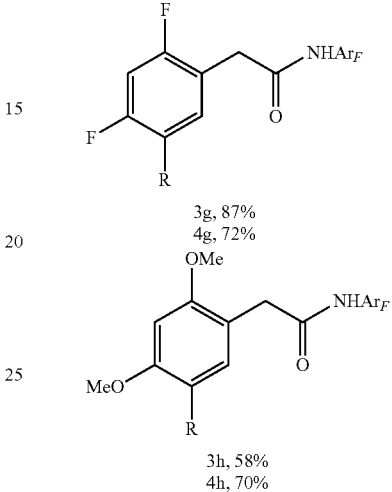

3g, 87%
4g, 72%

3h, 58%
4h, 70%

Alkylation of 1-naphthylacetic amide Compound 1i occurred exclusively at the 3-position, rather than the 8-position (Compounds 3i and 4i). When an unsubstituted amide reactive substrate Compound 1j was used with 20 mol % Pd(OAc)$_2$ and 40 mol % L19, methylation occurred at both meta positions to provide dimethylated product Compound 3j in 80% yield. Coupling of ethyl iodoacetate with this reactive substrate and the same ligand concentration, however, mainly produced the benzocyclobutene byproduct; the yield of the desired dialkylated product Compound 4j was <10%. This result demonstrates the subtle reactivity differences between these two alkylating reagents.

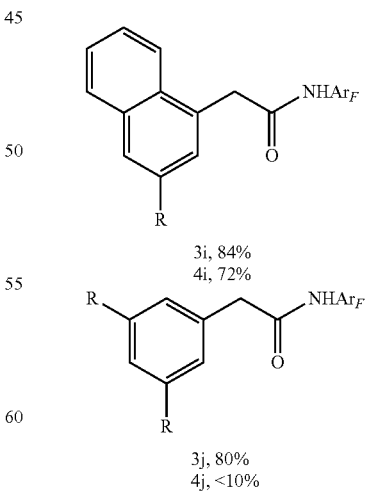

3i, 84%
4i, 72%

3j, 80%
4j, <10%

Reactive substrates bearing electron-donating or -withdrawing meta-substituents were also reactive with this protocol (Compounds 3k-3n and 4k-4n). A ligand concentration of 15 mol % Pd(OAc)$_2$ and 30 mol % L19 were used in the production of Compounds 3l, 3m and 4m, whereas concentrations of 20 mol % Pd(OAc)$_2$ and 40 mol % L19 were used for the preparation of Compounds 3k and 4k.

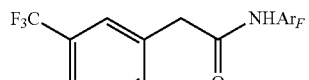

3k, 72%
4k, 51%

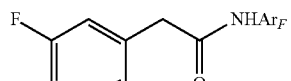

3l, 90%
4l, 86%

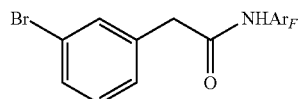

3m, 56%
4m, 47%

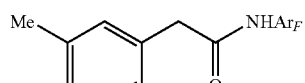

3n, 84%
4n, 32%

Methylation of the more sterically hindered p-MeO-substituted reactive substrate Compound 1o using concentrations of 20 mol % Pd(OAc)$_2$ and 40 mol % L19 was sluggish and poor yielding, providing Compound 3o in <10% yield. Interestingly, mono-alkylation of Compound 1o with ethyl iodoacetate under the same conditions afforded Compound 4o in 68% yield. A reactive substrate containing the less sterically hindered F-group reacted well with both coupling partners using concentrations of 20 mol % Pd(OAc)$_2$ and 40 mol % L19 to afford di-alkylated product Compounds 3p and 4p in 85% and 59% yields, respectively.

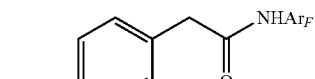

3o, <10%
4o, 68%

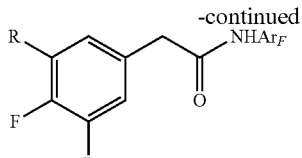

3p, 85%
4p, 59%

Using slightly altered reaction conditions (20 mol % Pd(OAc)$_2$, 40 mol % L19, 5 eq R—I, 5 eq AgOAc, 3 eq of norbornene), the methylation reaction was found to proceed effectively with a broad range of α-substituents, including methyl, acetoxyl, benzyloxy and phthaloyl-protected amino groups to give the di-methylated products in good yields (Compounds 3q-3t). Thus, this transformation enables the direct meta-functionalization of key biologically-active building-blocks, such as mandelic acid (Compounds 3r and 3s) and phenylglycine (Compound 3t). In contrast, ethoxycarbonylmethylation reaction was effective only for Compound 1s, containing a benzyloxy group at the benzylic position (Compound 4s).

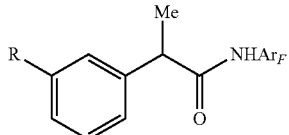

3q, 72%
4q, <10%

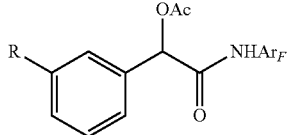

3r, 75%
4r, <10%

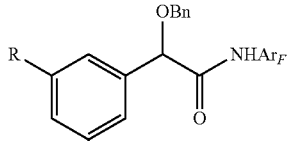

3s, 72%
4s, 52%

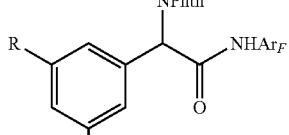

3t, 82%
4t, <10%

Notably, both alkylation reactions are compatible with tetrahydronapthalene (Compound 1u) and tetralone (Compound 1v) reactive substrates, despite the amide-directing groups being out of plane with the target Caryl)-H bonds. Product Compounds 3u,4u and 3v,4v were prepared using 15 mol % Pd(OAc)2, 30 mol % L19. Using 20 mol % Pd(OAc)2, 40 mol % L19, product Compounds 3w and 3x were prepared by meta-methylation of the heterocyclic dihydrobenzofuran- and indoline-containing substrate Compounds 1w and 1x. However, ethoxycarbonylmethylation of these heterocycles provided only trace products.

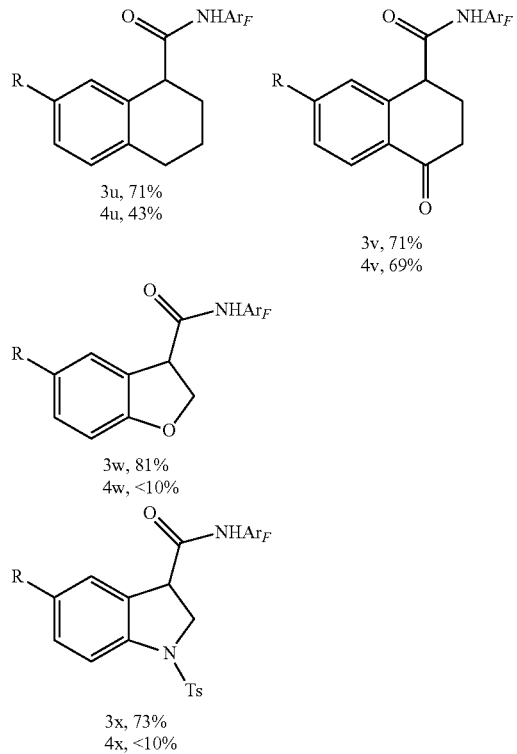

The generality of this meta-C—H functionalization strategy was examined by investigating additional organohalide coupling partners (below). Ethylation with ethyl iodide under standard conditions leads to exclusive formation of the undesired benzocyclobutene byproduct. Increasing the loading of ethyl iodide (6 eq) affords meta-ethylated product Compound 5 in 21% yield, with the benzocyclobutene still formed as the major product. We were pleased to find that meta-alkylation with benzyl bromide, a more reactive electrophile, proceeds smoothly to afford Compound 6a in 66% yield. Both electron-donating and -withdrawing substituents on the ortho-, meta- and para-positions of the benzyl bromide coupling partner are tolerated, providing meta-benzylated product Compounds 6b-6g in 60-75% yield.

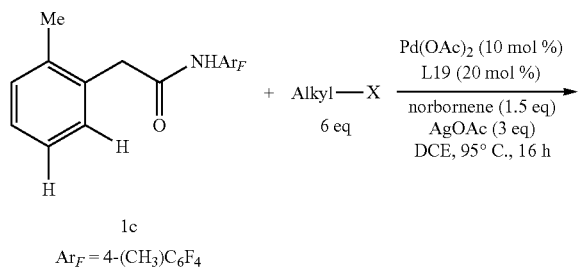

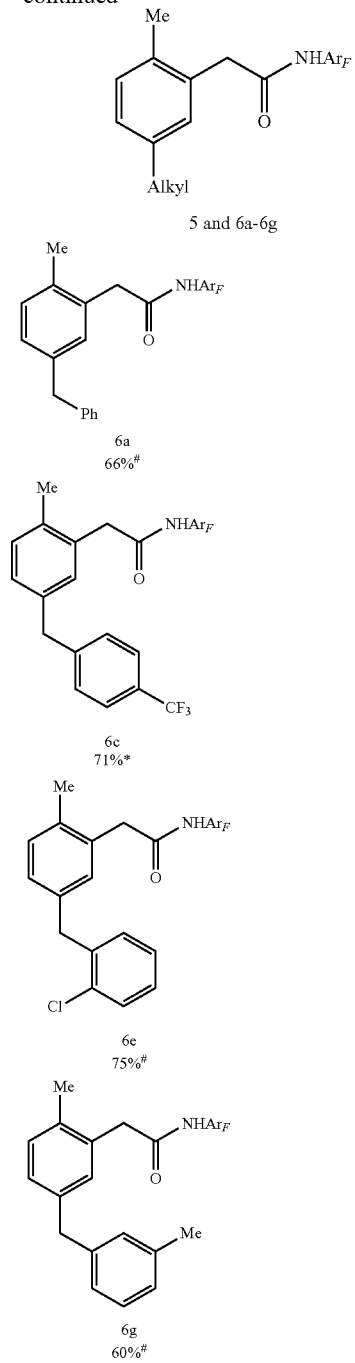

# = 15 mol % Pd(OAc)₂ and 30 mol % L19.
* = dichloromethane as solvent.

Also studied was whether this approach for meta-C—H functionalization could be adapted to achieve meta-C—H arylation, thereby providing a method for the synthesis of biaryl compounds. Gratifyingly, arylation with methyl 2-iodobenzoate in t-butyl methyl ether (TBME) provided the meta-arylated product Compound 7a in 64% yield. The use of methyl 3-iodobenzoate or methyl 4-iodobenzoate, however, resulted in the formation of the benzocyclobutene adduct as the major product.

These studies suggested that the presence of an ortho-coordinating group would be useful to promote oxidative addition of the aryl halide, consistent with previous studies. [Faccini et al., *J. Am. Chem. Soc.* 126, 78-79 (2004); and Martins et al., *Org. Lett.* 12, 5186-5188 (2010)] As such, other substituted 2-iodobenzoates (Ar—I) were examined and the desired products were obtained in moderate yields (Compounds 7b-7d).

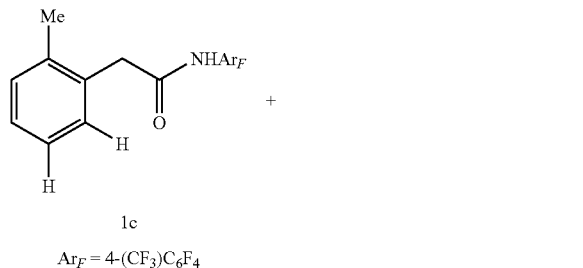

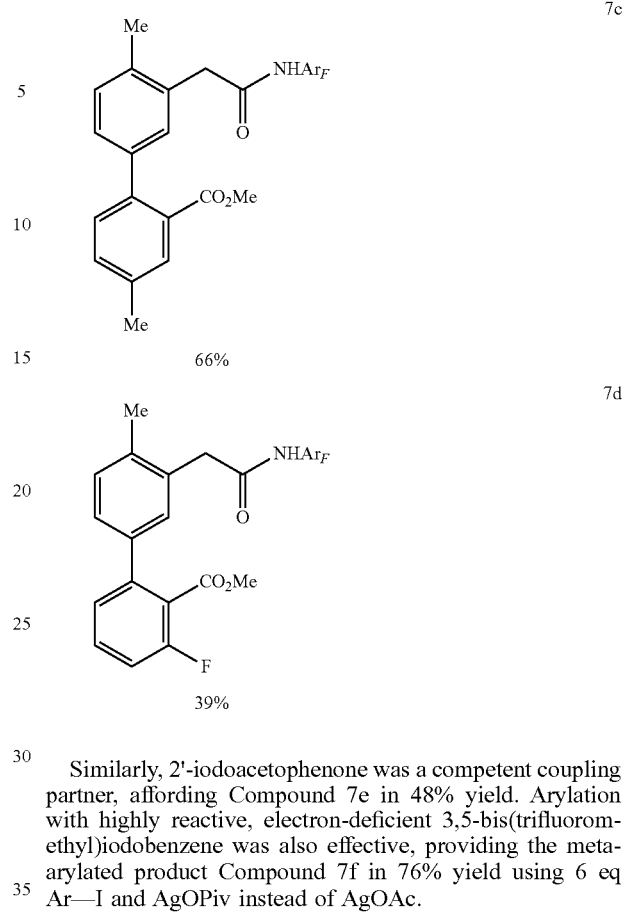

Similarly, 2'-iodoacetophenone was a competent coupling partner, affording Compound 7e in 48% yield. Arylation with highly reactive, electron-deficient 3,5-bis(trifluoromethyl)iodobenzene was also effective, providing the meta-arylated product Compound 7f in 76% yield using 6 eq Ar—I and AgOPiv instead of AgOAc.

The successful meta-arylation of substrates containing dihydrobenzofuran (Compound 8, 82% yield) and indoline (Compound 9, 69% yield) groups with

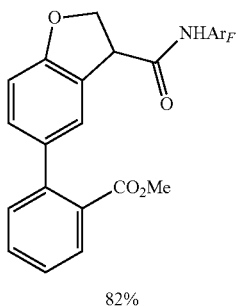

82%

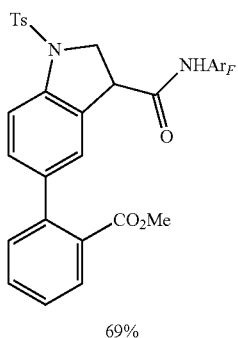

69% methyl 2-iodobenzoate is especially noteworthy in terms of demonstrating late-stage diversification of heterocycles with possible applications in medicinal chemistry. It is anticipated that further development of the ancillary pyridine ligand will broaden the scope of alkyl and aryl halides in this reaction, ultimately leading to a broadly useful method for meta-C—H functionalization using common ortho-directing groups and norbornene as a transient mediator.

In further studies of the generality of the contemplated reaction, the presence of an N—Ar$_F$ [4-(CF$_3$)C$_6$F$_4$NH—] group was found to not be needed as a steering functionality. Rather, other oxygen-containing amide-forming substituents such as a nitrophenylsulfonyl [Nos] group also functioned very well, as is seen from the reaction scheme shown below, from which a 95% yield of the meta,meta-diarylated compound was obtained.

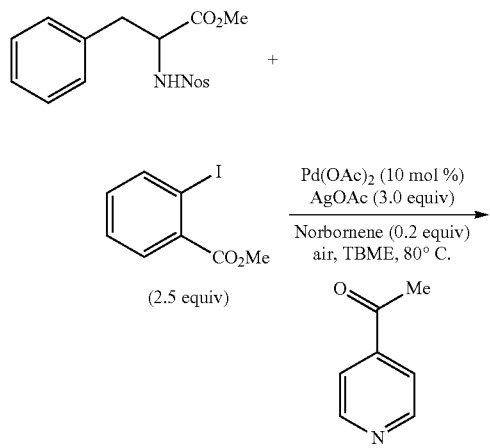

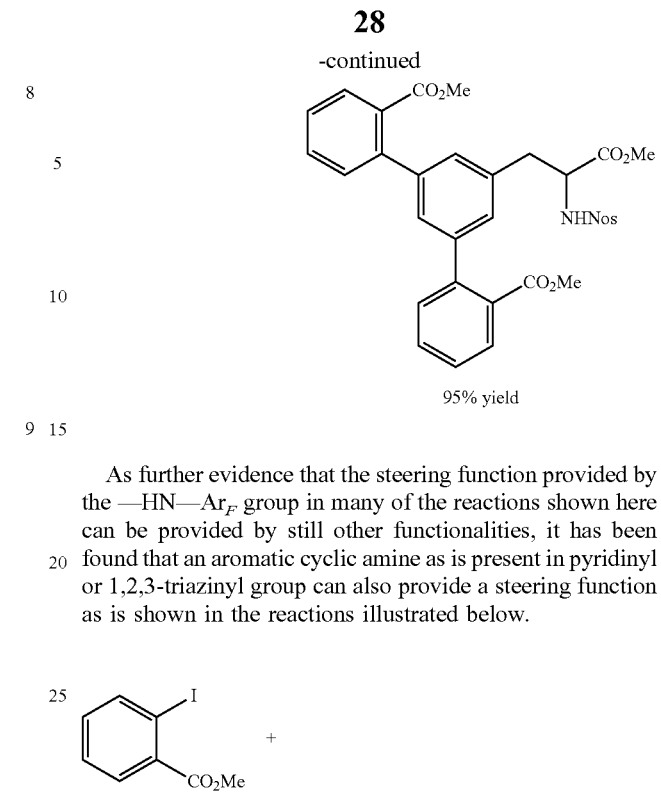

95% yield

As further evidence that the steering function provided by the —HN—Ar$_F$ group in many of the reactions shown here can be provided by still other functionalities, it has been found that an aromatic cyclic amine as is present in pyridinyl or 1,2,3-triazinyl group can also provide a steering function as is shown in the reactions illustrated below.

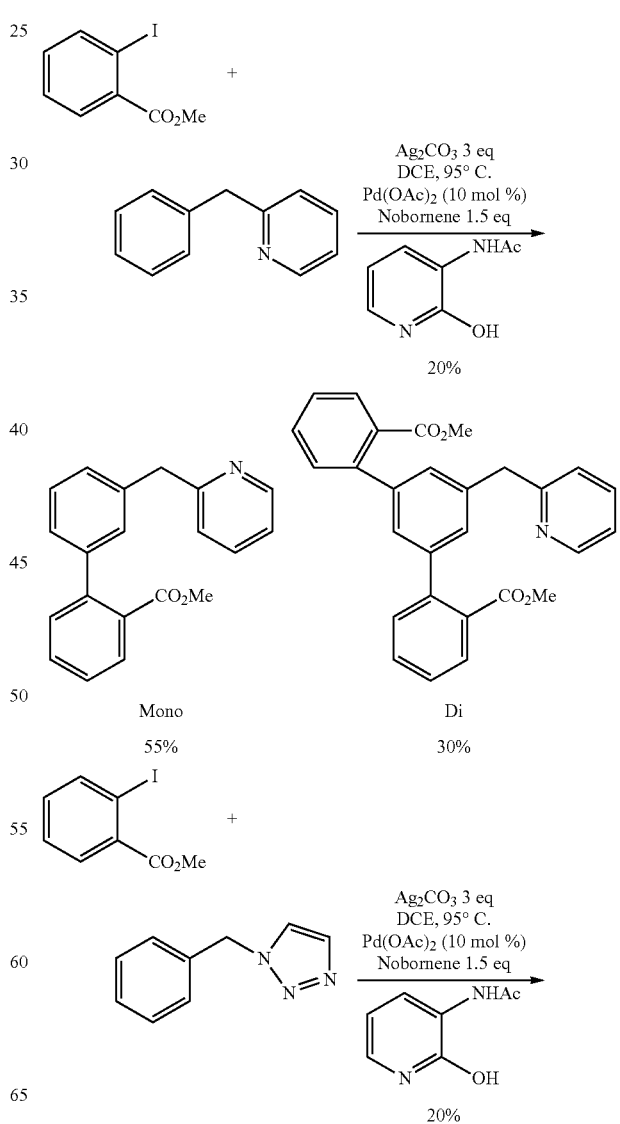

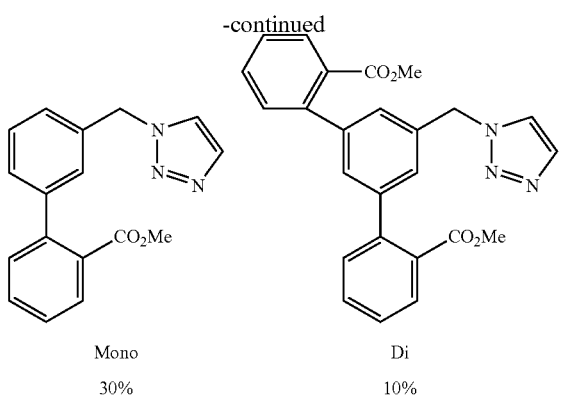

| Mono | Di |
|---|---|
| 30% | 10% |

Methods

General Information

Unless otherwise noted, all materials were used as received from commercial sources without further purification. Anhydrous solvents were obtained from the solvent purification system produced by JC Meyer Solvent Systems. Analytical thin layer chromatography (TLC) was performed on Merck Millipore precoated (0.25 mm thickness) silica gel plates with F254 indicator. Visualization was accomplished with UV light (254 nm) or the potassium permanganate stain solution. Flash chromatography was carried out with silica gel (32-63 μm) supplied by Dynamic Adsorbents.

$^1$H NMR spectra were recorded on a Bruker DRX-400 (400 MHz) spectrometer or a Bruker DRX-600 spectrometer (600 MHz) and chemical shifts were reported in ppm. The peak information was described as: br=broad, s=singlet, d=doublet, t=triplet, q=quartet, m=multiplet; coupling constants in Hz. $^{13}$C NMR spectra were recorded on a Bruker DRX-600 (150 MHz) spectrometer with complete proton decoupling. Chemical shifts of the NMR spectra were calibrated by the literature values of the solvent residual peaks. In $^{13}$C NMR spectra of the substrates and the products, peaks that correspond to those of the polyfluoroarylamide auxiliary appeared as nearly invisible due to multiple C—F couplings, and those peak values were not reported in the compound characterization section. High-resolution mass spectra (HRMS) were obtained on an Agilent LC/MSD TOF mass spectrometer.

Preparation of Substrates:

Procedure A

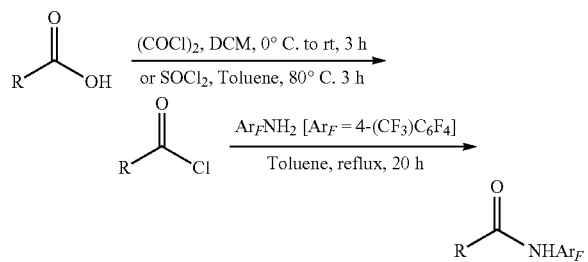

The previous reported procedure [Wang et al., *J. Am. Chem. Soc.* 135, 10326-10329 (2013)] was followed. Thus, 2,3,5,6-tetrafluoro-4-(trifluoromethyl)aniline (6.0 mmol) and an acid chloride (5.0 mmol), prepared from the corresponding carboxylic acid and oxalyl chloride (or thionyl chloride for substrate Compounds 1r, 1s and 1t), were dissolved in toluene (10.0 mL) in a 50 mL round-bottom flask. The mixture was stirred and refluxed under N$_2$ for 24 hours. After cooling to room temperature, the product mixture was concentrated in vacuo and was recrystallized from ethyl acetate/hexanes to give the pure amide substrate. Phenylacetic amide Compounds 1a-c, 1e-g, 1i, 1j, 1o and 1p had been synthesized and characterized before [Wang et al., *J. Am. Chem. Soc.* 135, 10326-10329 (2013)].

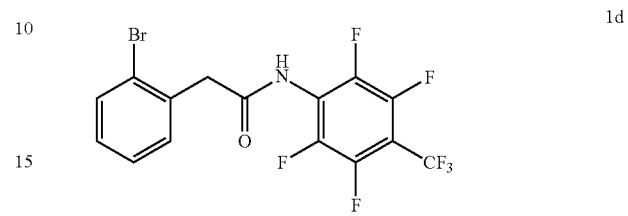

2-(2-Bromophenyl)-N-[2,3,5,6-tetrafluoro-4-(trifluoromethyl)phenyl]acetamide $^1$H NMR (600 MHz, acetone-d$^6$) δ 9.63 (br, 1H, N—H), 7.63 (d, J=8.0 Hz, 1H), 7.49 (d, J=8.0 Hz, 1H), 7.38 (t, J=8.0 Hz, 1H), 7.25 (t, J=8.0 Hz, 1H), 4.07 (s, 2H); $^{13}$C NMR (150 MHz, acetone-d$^6$) δ 168.38, 135.72, 133.48, 133.06, 130.00, 128.63, 125.68, 43.45. HRMS (ESI-TOF) m/z Calcd for C$_{15}$H$_6$BrF$_7$NO$^-$ [M–H]$^-$ 427.9526, found 427.9528.

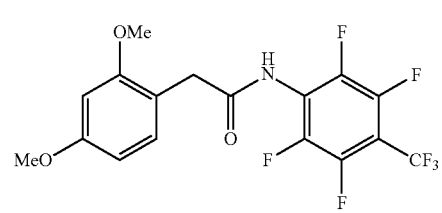

2-(2,4-Dimethoxyphenyl)-N-[2,3,5,6-tetrafluoro-4-(trifluoromethyl)phenyl]acetamide $^1$H NMR (600 MHz, acetone-d$^6$) δ 9.18 (br, 1H, N—H), 7.19 (d, J=8.2 Hz, 1H), 6.58 (s, 1H), 6.50 (d, J=8.2 Hz, 1H), 3.86 (s, 3H), 3.80 (s, 3H), 3.71 (s, 2H); $^{13}$C NMR (150 MHz, acetone-d$^6$) δ 169.96, 161.60, 159.43, 132.36, 116.24, 105.46, 99.22, 55.86, 55.63, 37.87. HRMS (ESI-TOF) m/z Calcd for C$_{17}$H$_{11}$F$_7$NO$_3^-$ [M–H]$^-$ 410.0633, found 410.0639.

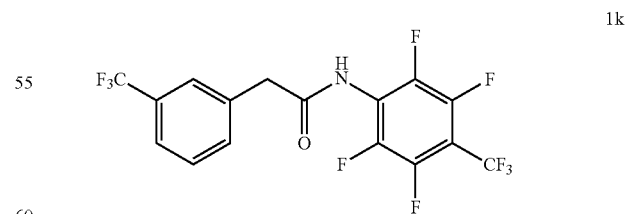

N-[2,3,5,6-tetrafluoro-4-(trifluoromethyl)phenyl]-2-[3-(trifluoromethyl)phenyl]acetamide $^1$H NMR (600 MHz, acetone-d$^6$) δ 9.74 (br, 1H, N—H), 7.75 (s, 1H), 7.69 (d, J=7.6 Hz, 1H), 7.64 (d, J=7.6 Hz, 1H), 7.60 (t, J=7.6 Hz, 1H), 4.05 (s, 2H); $^{13}$C NMR (150 MHz, acetone-d$^6$) δ 169.06, 137.20, 134.21, 131.00 (q, J=31.5 Hz), 130.21, 126.92 (q, J=3.0 Hz), 125.32 (q, J=268.5 Hz), 124.62 (q, J=3.0 Hz), 42.53. HRMS (ESI-TOF) m/z Calcd for C$_{16}$H$_6$F$_{10}$NO$^-$ [M−H]$^-$ 418.0295, found 418.0300.

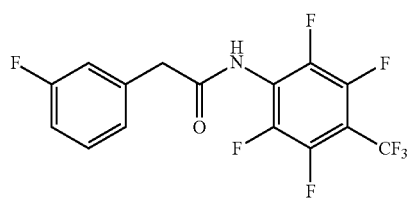

1l 2-(3-Fluorophenyl)-N-[2,3,5,6-tetrafluoro-4-(trifluoromethyl)phenyl]acetamide $^1$H NMR (600 MHz, acetone-d$^6$) δ 9.65 (br, 1H, N—H), 7.41-7.36 (m, 1H), 7.22 (d, J=7.8 Hz, 1H), 7.18 (d, J=10.2 Hz, 1H), 7.08-7.03 (m, 1H), 3.93 (s, 2H); $^{13}$C NMR (150 MHz, acetone-d$^6$) δ 167.72, 162.27 (d, J=243.0 Hz), 137.08 (d, J=7.5 Hz), 129.73 (d, J=9.0 Hz), 124.81 (d, J=3.0 Hz), 115.58 (d, J=22.5 Hz), 113.20 (d, J=21.0 Hz), 41.27. HRMS (ESI-TOF) m/z Calcd for C$_{15}$H$_6$F$_8$NO$^-$ [M−H]$^-$ 368.0327, found 368.0336.

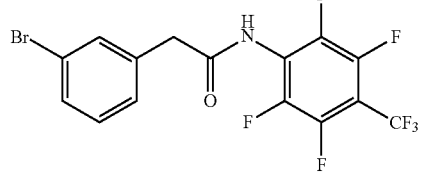

1m 2-(3-Bromophenyl)-N-[2,3,5,6-tetrafluoro-4-(trifluoromethyl)phenyl]acetamide $^1$H NMR (600 MHz, acetone-d$^6$) δ 9.70 (br, 1H, N—H), 7.62 (s, 1H), 7.49 (d, J=7.6 Hz, 1H), 7.42 (d, J=7.6 Hz, 1H), 7.34 (t, J=7.6 Hz, 1H), 3.94 (s, 2H); $^{13}$C NMR (150 MHz, acetone-d$^6$) δ 169.05, 138.42, 133.16, 131.26, 130.85, 129.17, 122.77, 42.48. HRMS (ESI-TOF) m/z Calcd for C$_{15}$H$_6$BrF$_7$NO$^-$ [M−H]$^-$ 427.9526, found 427.9524.

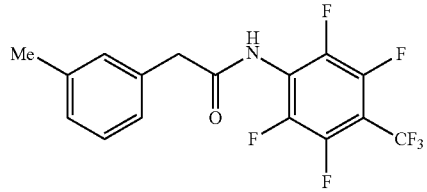

1n 2-(3-Methylphenyl)-N-[2,3,5,6-tetrafluoro-4-(trifluoromethyl)phenyl]acetamide $^1$H NMR (600 MHz, acetone-d$^6$) δ 9.54 (br, 1H, N—H), 7.23 (t, J=7.8 Hz, 1H), 7.21 (s, 1H), 7.17 (d, J=7.8 Hz, 1H), 7.09 (d, J=7.8 Hz, 1H), 3.83 (s, 2H), 2.32 (s, 3H); $^{13}$C NMR (150 MHz, acetone-d$^6$) γ 169.61, 138.82, 135.66, 130.79, 129.28, 128.49, 127.10, 43.16, 21.36. HRMS (ESI-TOF) m/z Calcd for C$_{16}$H$_9$F$_7$NO$^-$ [M−H]$^-$ 364.0578, found 364.0590.

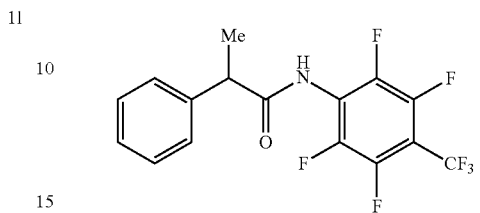

1q

2-Phenyl-N-[2,3,5,6-tetrafluoro-4-(trifluoromethyl)phenyl]propanamide $^1$H NMR (600 MHz, acetone-d$^6$) δ 9.47 (br, 1H, N—H), 7.41 (d, J=7.1 Hz, 2H), 7.38-7.33 (m, 2H), 7.30-7.25 (m, 1H), 4.07 (q, J=7.0 Hz, 1H), 1.51 (d, J=7.0 Hz, 3H); $^{13}$C NMR (150 MHz, acetone-d$^6$) δ 172.81, 142.19, 129.51, 128.35, 127.97, 47.03, 19.52. HRMS (ESI-TOF) m/z Calcd for C$_{16}$H$_9$F$_7$NO$^-$ [M−H]$^-$ 364.0578, found 364.0587.

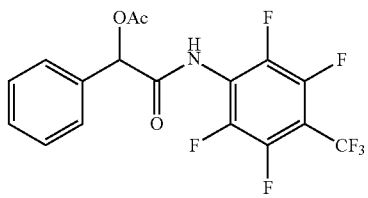

1r

2-Acetoxy-2-phenyl-N-[2,3,5,6-tetrafluoro-4-(trifluoromethyl)phenyl]acetamide $^1$H NMR (600 MHz, CDCl$_3$) δ 7.76 (br, 1H, N—H), 7.50-7.46 (m, 2H), 7.43-7.39 (m, 3H), 6.28 (s, 1H), 2.24 (s, 3H); $^{13}$C NMR (150 MHz, CDCl$_3$) δ 169.36, 166.56, 134.14, 129.85, 129.25, 127.69, 75.60, 21.02. HRMS (ESI-TOF) m/z Calcd for C$_{17}$H$_9$F$_7$NO$_3^-$ [M−H]$^-$ 408.0476, found 408.0480.

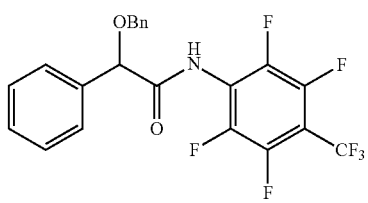

1s 2-(Benzyloxy)-2-phenyl-N-[2,3,5,6-tetrafluoro-4-(trifluoromethyl)phenyl]acetamide $^1$H NMR (600 MHz, acetone-d$^6$) δ 9.78 (br, 1H, N—H), 7.59 (d, J=7.2 Hz, 2H), 7.46-7.42 (m, 4H), 7.42-7.37 (m, 3H), 7.34 (t, J=7.2 Hz, 1H), 5.20 (s, 1H), 4.72 (d, J=11.6 Hz, 1H), 4.67 (d, J=11.6 Hz, 1H); $^{13}$C NMR (150 MHz, acetone-d⁶) δ 169.76, 138.23, 137.93, 129.54, 129.47, 129.29, 128.97, 128.82, 128.21, 82.48, 72.26. HRMS (ESI-TOF) m/z Calcd for $C_{16}H_9F_7NO^-$ [M–H]⁻ 456.0840, found 456.0862.

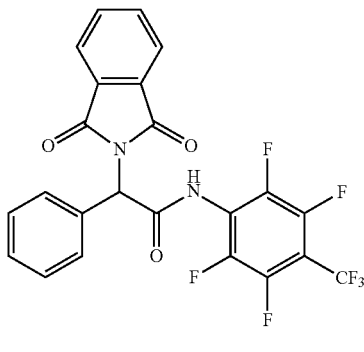

1t 2-(1,3-Dioxoisoindolin-2-yl)-2-phenyl-N-[2,3,5,6-tetrafluoro-4-(trifluoromethyl)phenyl]acetamide ¹H NMR (600 MHz, acetone-d⁶) δ 9.68 (br, 1H, N—H), 7.93-7.87 (m, 4H), 7.67 (d, J=7.3 Hz, 2H), 7.44-7.40 (m, 2H), 7.39-7.35 (m, 1H), 6.34 (s, 1H); ¹³C NMR (150 MHz, acetone-d⁶) δ 167.87, 166.55, 135.55, 135.53, 132.78, 130.97, 129.53, 129.38, 124.23, 58.04. HRMS (ESI-TOF) m/z Calcd for $C_{23}H_{10}F_7N_2O_3^-$ [M–H]⁻ 495.0585, found 495.0591.

Procedure B

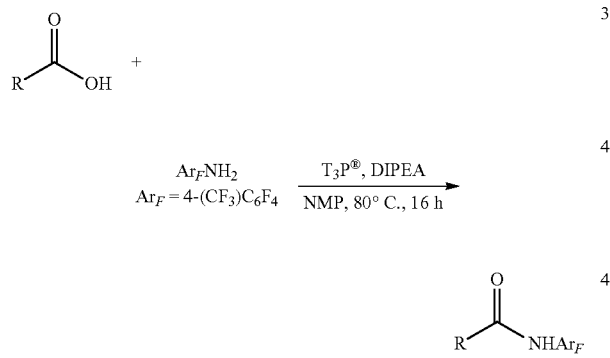

The carboxylic acid (2.0 mmol) and 2,3,5,6-tetrafluoro-4-(trifluoromethyl)aniline (2.2 mmol) were dissolved in 7.0 mL 1-methyl-2-pyrrolidone (NMP) in a 35 mL pressure tube. 2.5 mL (4.2 mmol) of propylphosphonic anhydride solution (T₃P®, 50 wt. % in ethyl acetate) and 0.7 mL (4.0 mmol) of N,N-diisopropylethylamine (DIPEA) were then added using syringes. The tube was sealed with a Teflon screw cap and the mixture was stirred at 80° C. for 16 hours. After cooling to room temperature, the mixture was diluted with ethyl acetate (15 mL) and water (10 mL), and then the organic layer was separated, washed with brine (10 mL×3) and dried over anhydrous Na₂SO₄. After filtration and evaporation, the resulting crude materials were passed through a short silica gel column with ethyl acetate/hexanes (1:1) as the eluent to remove the very polar compounds. The collected product fraction mixed with the residual 2,3,5,6-tetrafluoro-4-(trifluoromethyl)aniline was concentrated. The resulting solid mixture was recrystallized with ethyl acetate and hexanes to give the pure product. Use of T₃P® as a promoter for amide formation had been discussed in the previous literature [Ech-Chahad et al., *Tetrahedron Letters* 46, 5113-5115 (2005)]. Substrates 1u-x were prepared following this procedure.

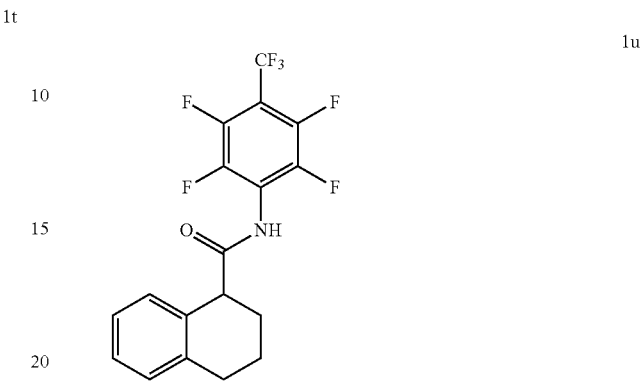

1u

N-[2,3,5,6-tetrafluoro-4-(trifluoromethyl)phenyl]-1,2,3,4-tetrahydronaphthalene-1-carboxamide ¹H NMR (600 MHz, CDCl₃) δ 7.30-7.20 (m, 4H), 6.81 (br, 1H, N—H), 3.95 (t, J=5.4 Hz, 1H), 2.95-2.82 (m, 2H), 2.42-2.35 (m, 1H), 2.14-2.07 (m, 1H), 1.94-1.85 (m, 2H); ¹³C NMR (150 MHz, CDCl₃) δ 173.09, 138.32, 132.74, 130.44, 130.05, 128.37, 126.91, 47.43, 29.19, 27.65, 20.39. HRMS (ESI-TOF) m/z Calcd for $C_{18}H_{11}F_7NO^-$ [M–H]⁻ 390.0734, found 390.0752.

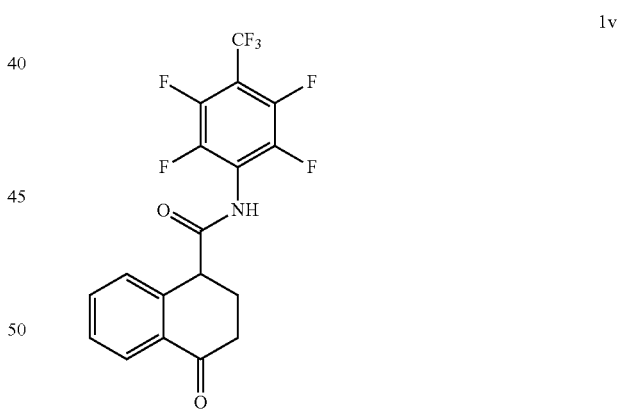

1v

4-Oxo-N-[2,3,5,6-tetrafluoro-4-(trifluoromethyl)phenyl]-1,2,3,4-tetrahydronaphthalene-1-carboxamide ¹H NMR (400 MHz, CDCl₃) δ 8.16 (d, J=8.0 Hz, 1H), 7.66 (t, J=8.0 Hz, 1H), 7.53 (t, J=8.0 Hz, 1H), 7.43 (d, J=8.0 Hz, 1H), 6.96 (br, 1H, N—H), 4.11 (t, J=4.8 Hz, 1H), 2.89-2.67 (m, 3H), 2.55-2.45 (m, 1H); ¹³C NMR (150 MHz, CDCl₃) δ 196.35, 170.31, 139.44, 134.69, 132.75, 129.38, 129.04, 128.61, 46.88, 35.75, 27.08. HRMS (ESI-TOF) m/z Calcd for $C_{18}H_9F_7NO_2^-$ [M–H]⁻ 404.0527, found 404.0535.

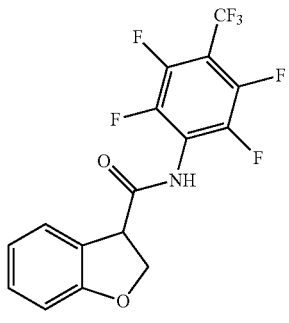

N-[2,3,5,6-tetrafluoro-4-(trifluoromethyl)phenyl]-2,3-dihydrobenzofuran-3-carboxamide $^1$H NMR (600 MHz, acetone-d$^6$) δ 9.92 (br, 1H, N—H), 7.48 (d, J=7.8 Hz, 1H), 7.20 (t, J=7.8 Hz, 1H), 6.90 (t, J=7.8 Hz, 1H), 6.81 (d, J=7.8 Hz, 1H), 4.95 (dd, J=5.5, 8.0 Hz, 1H), 4.81-4.74 (m, 2H); $^{13}$C NMR (150 MHz, acetone-d$^6$) δ 170.27, 161.14, 130.27, 126.57, 125.60, 121.31, 110.51, 73.75, 49.24. HRMS (ESI-TOF) m/z Calcd for $C_{16}H_7F_7NO_2^-$ [M−H]$^-$ 378.0370, found 378.0376.

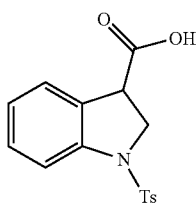 [SMILES: Cc1ccc(S(=O)(=O)N2CC(C(=O)O)c3ccccc32)cc1]

1-Tosylindoline-3-carboxylic acid 2,3-Dihydro-1H-indole-3-carboxylic acid (0.50 g, 3.0 mmol) was dissolved in a solvent mixture of 9 mL DMF and 6 mL H$_2$O. Diisopropylethylamine (1.3 mL, 7.5 mmol) was added, and the resulting mixture was stirred at room temperature for 5 minutes. Then, 4-toluenesulfonyl chloride (0.67 g, 3.5 mmol) was added. After stirring the mixture at room temperature for 7 hours, TLC indicated complete consumption of the starting material.

The mixture was diluted by the addition of 15 mL saturated aqueous NaHCO$_3$ solution and 10 mL of ethyl acetate. The organic layer was separated, and extracted with saturated aqueous NaHCO$_3$ (10 mL×3). The combined aqueous layer was acidified by hydrochloric acid (36%) to pH=5, and a white precipitate was observed. Ethyl acetate (20 mL×3) was used to extract the product. The combined organic layer was further washed with saturated aqueous NaCl (15 mL×4) to remove the residual DMF, and dried over anhydrous Na$_2$SO$_4$. After evaporation of solvent, the product was obtained as an off-white solid (0.89 g, 92% yield), which was directly used for the next step. $^1$H NMR (400 MHz, DMSO-d$^6$) δ 7.72 (d, J=8.4 Hz, 2H), 7.48 (d, J=8.4 Hz, 1H), 7.37 (d, J=8.4 Hz, 2H), 7.32-7.23 (m, 2H), 7.02 (t, J=8.0 Hz, 1H), 4.19-4.10 (m, 2H), 4.04 (dd, J=7.2, 16.0 Hz, 1H), 2.34 (s, 3H); $^{13}$C NMR (150 MHz, DMSO-d$^6$) δ 171.85, 144.49, 140.99, 132.89, 129.95, 129.41, 128.82, 127.26, 125.79, 123.66, 113.80, 51.84, 44.45, 21.02. HRMS (ESI-TOF) m/z Calcd for $C_{16}H_{16}NO_4S^+$ [M+H]$^+$ 318.0795, found 318.0796.

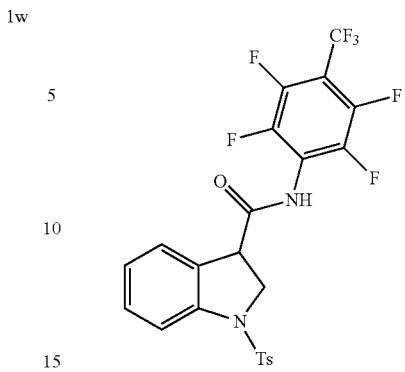

N-[2,3,5,6-tetrafluoro-4-(trifluoromethyl)phenyl]-1-tosylindoline-3-carboxamide $^1$H NMR (600 MHz, acetone-d$^6$) δ 9.88 (br, 1H, N—H), 7.79 (d, J=8.2 Hz, 2H), 7.63 (d, J=8.1 Hz, 1H), 7.42 (d, J=7.6 Hz, 1H), 7.37 (d, J=8.2 Hz, 2H), 7.33-7.29 (m, 1H), 7.08-7.03 (m, 1H), 4.54 (dd, J=7.0, 9.7 Hz, 1H), 4.38 (dd, J=7.0, 10.8 Hz, 1H), 4.29 (dd, J=9.7, 10.8 Hz, 1H), 2.37 (s, 3H); $^{13}$C NMR (150 MHz, acetone-d$^6$) δ 169.61, 145.40, 142.97, 134.93, 130.77, 130.67, 129.94, 128.38, 125.88, 124.57, 115.38, 53.16, 47.08, 21.41. HRMS (ESI-TOF) m/z Calcd for $C_{23}H_{14}F_7N_2O_3S^-$ [M−H]$^-$ 531.0619, found 531.0627.

Early Investigation of the Norbornene Migratory Insertion:
a. Screening of Inorganic Bases without AgOAc:

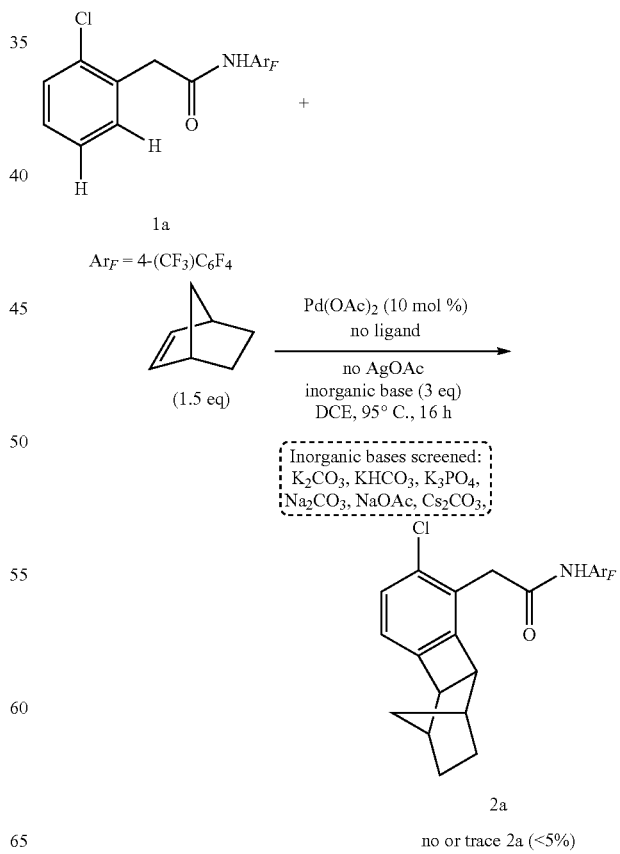

37 b. Screening of Inorganic Bases with AgOAc:

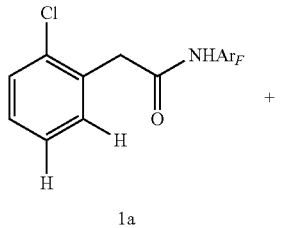

1a

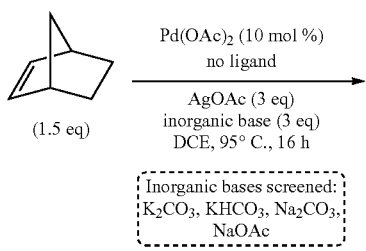

Pd(OAc)$_2$ (10 mol %)
no ligand
—————————
AgOAc (3 eq)
inorganic base (3 eq)
DCE, 95° C., 16 h Inorganic bases screened:
K$_2$CO$_3$, KHCO$_3$, Na$_2$CO$_3$, NaOAc

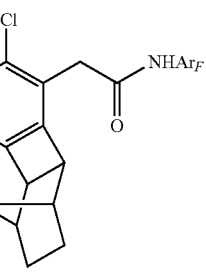

2a no or trace 2a (<5%)

c. Screening of Solvents:

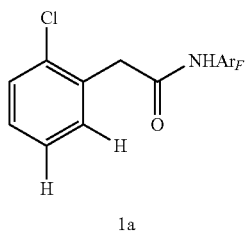

1a

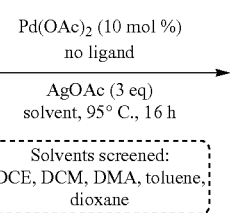

Pd(OAc)$_2$ (10 mol %)
no ligand
—————————
AgOAc (3 eq)
solvent, 95° C., 16 h

Solvents screened:
DCE, DCM, DMA, toluene, dioxane

38

-continued

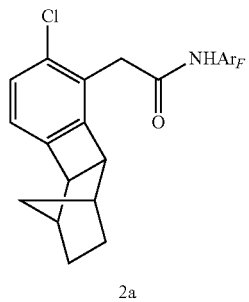

2a no or trace 2a (<5%)

Ligand Syntheses

Ligands L1-L7 and L9-L15 were commercially available and used as received from commercial sources. Ligands L8 [Kaneko et al., *Chem. Pharm. Bull.* 34, 3658-3671 (1986)], L16 [Wasa et al., *J. Am. Chem. Soc.* 134, 18570-18572 (2012)] and L17 [Li et al., *J. Am. Chem. Soc.* 136, 5267-5270 (2014)] were prepared according to the literature procedures. Ligands L18 and L19 were prepared according to the following procedures. Amines I-3 and II-1 were prepared following a literature procedures [Desai et al., *Tetrahedron Lett.* 30, 5223-5226 (1989)].

A. Synthesis of L18

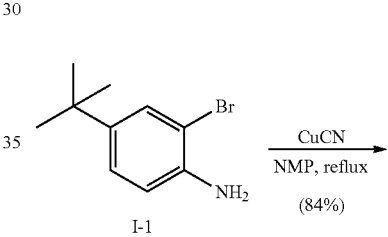

I-1

CuCN
————
NMP, reflux (84%)

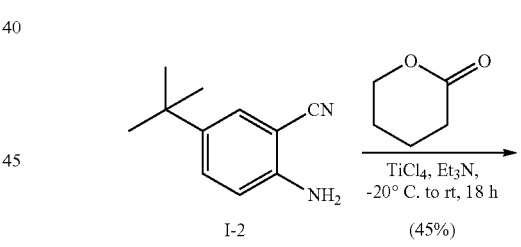

I-2

TiCl$_4$, Et$_3$N,
—————
-20° C. to rt, 18 h (45%)

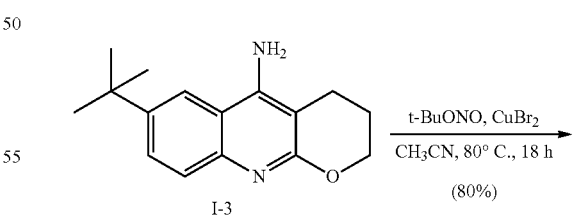

I-3 t-BuONO, CuBr$_2$
——————
CH$_3$CN, 80° C., 18 h (80%)

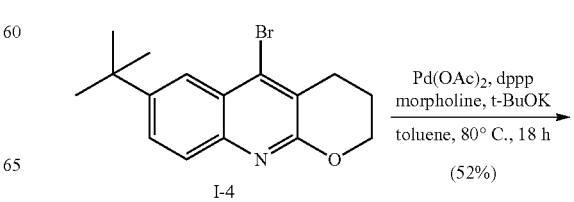

I-4

Pd(OAc)$_2$, dppp
morpholine, t-BuOK
————————
toluene, 80° C., 18 h (52%)

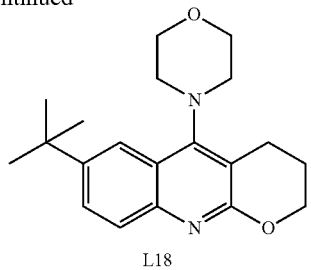

L18

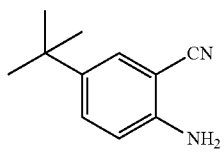

I-2

To a mixture of 2-bromo-4-tert-butylaniline (Compound I-1, 16.8 g, 74 mmol) and CuCN (13.29 g, 148 mmol) in a 250 mL round-bottom flask was added NMP (N-methylpyrrolidone, 100 mL). The mixture was heated to reflux under nitrogen until TLC analysis showed full conversion of the starting material. The mixture was cooled to room temperature and the solvent was removed under vacuum.

To the residue was added aq. NH$_4$OH at 0° C. Ethyl acetate was used for extraction (three times). The combined organic phase was dried over anhydrous MgSO$_4$, filtered, and evaporated under vacuum. The residue was purified by flash chromatography (ethyl acetate:hexanes=1:10) to provide the aminobenzonitrile Compound 1-2 as a yellow solid (10.8 g, 84% yield). $^1$H NMR (400 MHz, CDCl$_3$) δ 7.39-7.33 (m, 2H), 6.70 (d, J=8.4 Hz, 1H), 4.32 (br, 2H, NH$_2$), 1.25 (s, 9H); $^{13}$C NMR (100 MHz, CDCl$_3$) δ 147.48, 141.15, 131.77, 128.56, 118.22, 115.32, 95.63, 34.02, 31.21. HRMS (ESI-TOF) m/z Calcd for C$_{11}$H$_{15}$N$_2^+$ [M+H]$^+$ 175.1230, found 175.1235.

I-3

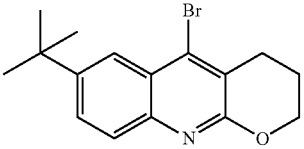

To a stirred solution of δ-valerolactone (3.0 g, 30 mmol) in methylene chloride (50 ml) at −20° C. was added titanium (IV) chloride (11.4 g, 60.0 mmol). The reaction mixture became dark yellow in color and then a mixture of triethylamine (6.1 g, 60 mmol) and 2-amino-5-tert-butylbenzonitrile (Compound I-2, 5.22 g, 30 mmol) in methylene chloride (10 ml) was added. The reaction mixture, which immediately darkened, was permitted to warm to room temperature and stirred for 8 hours. Additional δ-valerolactone (3.0 g, 30 mmol) was added and the stirring was continued for another 10 hours.

At the end of this period the reaction mixture was slowly poured into cold 28% aq. NH$_4$OH (100 ml) and methylene chloride (100 ml). The mixture was stirred for 15 minutes and filtered through a Celite® pad, which was washed with methylene chloride (50 ml) and water (100 ml). The organic layer was separated, washed with water and dried over anhydrous MgSO$_4$). The methylene chloride was removed under vacuum to afford an oil that was triturated with ether to give the crude product. Recrystallization from isopropyl alcohol afforded pure amine Compound 1-3 (3.46 g, 45% yield). $^1$H NMR (400 MHz, CDCl$_3$) δ 7.69 (d, J=8.8 Hz, 1H), 7.62 (dd, J=8.8, 2.0 Hz, 1H), 7.50 (d, J=2.0 Hz, 1H), 4.68 (br, 2H, NH$_2$), 4.35-4.30 (m, 2H), 2.64 (t, J=6.4 Hz, 2H), 2.15-2.06 (m, 2H), 1.39 (s, 9H); $^{13}$C NMR (100 MHz, CDCl$_3$) δ 160.33, 148.56, 145.49, 144.45, 128.04, 127.74, 115.48, 114.61, 97.30, 66.59, 34.93, 31.53, 21.90, 20.70. HRMS (ESI-TOF) m/z Calcd for C$_{16}$H$_{21}$N$_2$O$^+$ [M+H]$^+$ 257.1648, found 257.1651.

I-4

To a suspension of amine Compound I-3 (3.0 g, 11.7 mmol) and copper (II) bromide (6.52 g, 29.3 mmol) in CH$_3$CN (80 mL) was added tert-butyl nitrite (12 mL, 100.9 mmol). The suspension was heated at reflux under nitrogen overnight (about 18 hours). After cooling to room temperature the solvent was removed in vacuo. To the crude product was added aq. NH$_4$OH solution (20 mL) at 0° C. The aqueous layer was extracted with CH$_2$Cl$_2$ and the combined organic layer was concentrated in vacuo. The residue was purified by flash chromatography (ethyl acetate:hexanes=1:10) to give a yellow solid Compound I-4 (3.02 g, 80% yield). $^1$H NMR (400 MHz, CDCl$_3$) δ 7.98 (d, J=2.0 Hz, 1H), 7.75 (d, J=8.8 Hz, 1H), 7.69 (dd, J=8.8, 2.0 Hz, 1H), 4.38 (t, J=5.2 Hz, 2H), 2.99 (t, J=6.4 Hz, 2H), 2.14-2.06 (m, 2H), 1.41 (s, 9H); $^{13}$C NMR (100 MHz, CDCl$_3$) δ 159.35, 148.22, 144.28, 137.25, 128.90, 127.44, 124.58, 121.50, 119.57, 67.29, 35.07, 31.34, 27.51, 22.14. HRMS (ESI-TOF) m/z Calcd for C$_{16}$H$_{19}$BrNO$^+$ [M+H]$^+$ 320.0645, found 320.0647.

L18

A flame-dried round-bottom flask was charged with the bromide Compound I-4 (160 mg, 0.5 mmol), Pd(OAc)$_2$ (11.2 mg, 10 mol %), 1,3-bis-(diphenylphophino)propane (dppp, 20.6 mg, 10 mol %), and potassium tert-butoxide (112 mg, 2 eq). The flask was sealed by a rubber septum and evacuated and backfilled with nitrogen for three times. Toluene (5 mL), morpholine (130 mg, 0.13 mL, 3 eq) were injected through rubber septum and the mixture was heated to 100° C. with stirring until the starting material has been consumed as monitored by TLC.

The reaction mixture was cooled to room temperature, diluted with diethyl ether, washed with brine (30 mL), dried over anhydrous MgSO$_4$, filtered, and concentrated under reduced pressure. The residue was purified by flash chromatography (ethyl acetate hexanes=1:5) to give a white solid ligand L18 (83 mg, 52%). $^1$H NMR (400 MHz, CDCl$_3$) δ 8.00 (d, J=2.4 Hz, 1H), 7.75 (d, J=8.8 Hz, 1H), 7.64 (dd, J=8.8, 2.4 Hz, 1H), 4.39 (t, J=5.2 Hz, 2H), 3.94 (t, J=4.4 Hz, 4H), 3.50-3.20 (m, 4H), 2.97 (t, J=6.4 Hz, 2H), 2.10-2.01 (m, 2H), 1.41 (s, 9H); $^{13}$C NMR (150 MHz, CDCl$_3$) δ 160.54, 154.92, 146.40, 145.39, 128.00, 127.65, 123.16, 118.72, 114.34, 68.13, 67.02, 51.03, 35.01, 31.55, 24.12, 22.24. HRMS (ESI-TOF) m/z Calcd for C$_{20}$H$_{27}$N$_2$O$_2$$^+$ [M+H]$^+$ 327.2067, found 327.2073.

B. Synthesis of L19

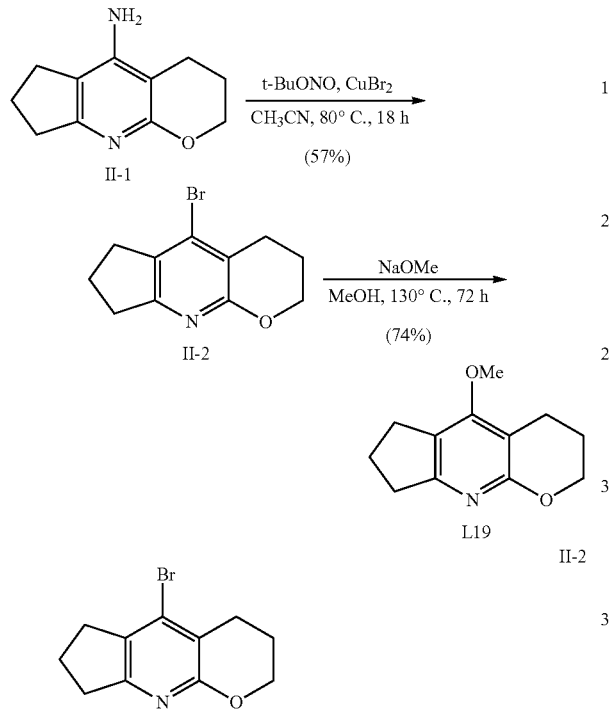

To a suspension of amine Compound II-1 (3.0 g, 15.8 mmol) and copper (II) bromide (8.85 g, 39.6 mmol) in CH$_3$CN (80 mL) was added tert-butyl nitrite (16 mL, 134.5 mmol). The suspension was heated at reflux under nitrogen overnight (about 18 hours).

After cooling to room temperature, solvent was removed in vacuo. To the crude product was added aq. NH$_4$OH solution (20 mL) at 0° C. The aqueous layer was extracted with CH$_2$Cl$_2$ and the combined organic layer was concentrated in vacuo. The residue was purified by flash chromatography (ethyl acetate:hexanes=1:10) to give a yellow solid Compound 11-2 (2.30 g, 57% yield). $^1$H NMR (400 MHz, CDCl$_3$) δ 4.26 (t, J=5.0 Hz, 2H), 2.98 (t, J=8.0 Hz, 2H), 2.87 (t, J=7.6 Hz, 2H), 2.73 (t, J=6.4 Hz, 2H), 2.15-2.05 (m, 2H), 2.05-1.96 (m, 2H); $^{13}$C NMR (100 MHz, CDCl$_3$) δ 161.68, 161.04, 134.30, 131.39, 114.00, 66.99, 35.28, 31.94, 25.65, 22.17, 22.08. HRMS (ESI-TOF) m/z Calcd for C$_{11}$H$_{15}$BrNO$^+$ [M+H]$^+$ 254.0175, found 254.0179.

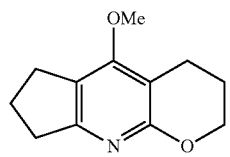

To a mixture of bromide Compound 11-2 (3.0 g, 11.7 mmol) and sodium methoxide (6.3 g, 117 mmol) in a 75 mL sealed tube was added anhydrous MeOH (30 mL). The suspension was heated at 130° C. under nitrogen for 72 hours. After cooling to room temperature solvent was removed in vacuo. To the crude product was added aq. NH$_4$Cl solution. The aqueous layer was extracted with CH$_2$Cl$_2$ and the combined organic layer was concentrated in vacuo. The residue was purified by flash chromatography (ethyl acetate:hexanes=1:5 to 1:2) to provide a white solid ligand L19 (1.80 g, 74% yield). $^1$H NMR (400 MHz, CDCl$_3$) δ 4.23 (t, J=5.2 Hz, 2H), 3.97 (s, 3H), 3.08 (t, J=7.6 Hz, 2H), 2.83 (t, J=7.6 Hz, 2H), 2.62 (t, J=6.4 Hz, 2H), 2.10-1.98 (m, 2H), 1.96-1.88 (m, 2H); $^{13}$C NMR (100 MHz, CDCl$_3$) δ 164.24, 162.30, 161.68, 116.26, 103.95, 66.80, 58.50, 34.18, 30.16, 23.28, 21.71, 19.57. HRMS (ESI-TOF) m/z Calcd for C$_{12}$H$_{18}$NO$_2$$^+$ [M+H]$^+$ 206.1176, found 206.1176.

Ligand-Enabled Norbornene-Mediated meta-C—H Alkylation of Phenylacetic Amides:

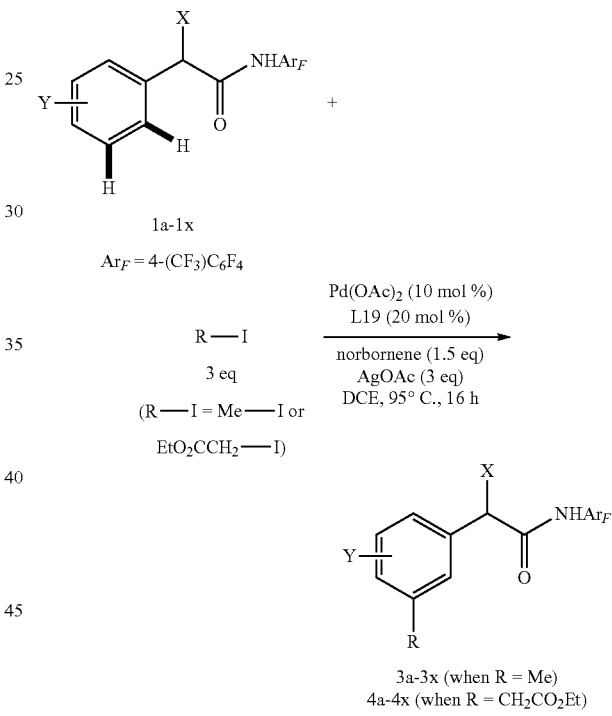

General Procedure for the ligand-enabled norbornene-mediated meta-C—H activation A 2-dram vial equipped with a magnetic stir bar was charged with phenylacetic amide substrates (0.10 mmol), Pd(OAc)$_2$ (2.2 mg, 10 mol %), L19 (4.1 mg, 20 mol %), AgOAc (50 mg, 0.30 mmol) and norbornene (14.1 mg, 0.15 mmol). Methyl iodide (19 μL, 0.30 mmol) or ethyl iodoacetate (36 μL, 0.30 mmol) was then added via a microsyringe. After 1.5 mL of DCE was injected, the vial was capped and closed tightly. The reaction mixture was then stirred at 95° C. for 16 hours.

After cooling to room temperature, the mixture was passed through a pad of Celite® with ethyl acetate as the eluent to remove any insoluble materials. The resulting solution was concentrated, and the residual mixture was dissolved with a minimal amount of acetone and loaded onto a silica gel column or a preparative TLC plate. The pure product was then isolated by column chromatography or preparative TLC with ethyl acetate and hexanes as the eluent.

In the reactions with substrate Compounds 1j and 1p-1t where di-alkylation occurred, 20 mol % of Pd(OAc)$_2$, 40 mol % of ligand L19, 5 equiv of alkyl iodide, 5 equiv of AgOAc and 3 equiv of norbornene were used, and the volume of DCE was increased to 2.5 mL. Otherwise, the conditions and workups were exactly the same as those of mono-alkylation.

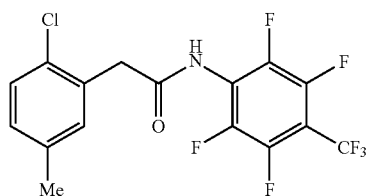

3a 2-(2-Chloro-5-methylphenyl)-N-[2,3,5,6-tetrafluoro-4-(trifluoromethyl)phenyl]acetamide Column chromatography using hexanes/EtOAc (4/1) as the eluent provided the pure product as a white solid (80% yield). $^1$H NMR (600 MHz, acetonitrile-d$^3$) δ 8.51 (br, 1H, N—H), 7.32 (d, J=8.4 Hz, 1H), 7.23 (d, J=1.8 Hz, 1H), 7.13 (dd, J=8.4, 1.8 Hz, 1H), 3.89 (s, 2H), 2.32 (s, 3H); $^{13}$C NMR (150 MHz, acetonitrile-d$^3$) δ 169.07, 138.34, 133.69, 133.35, 132.10, 130.66, 129.98, 41.12, 20.75. HRMS (ESI-TOF) m/z Calcd for C$_{16}$H$_8$ClF$_7$NO$^-$ [M–H]$^-$ 398.0188, found 398.0185.

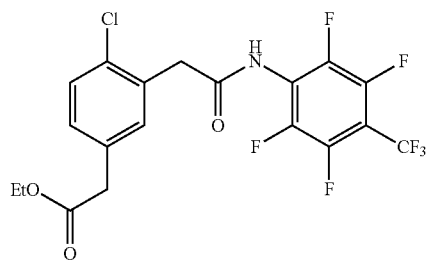

4a

2-[2-Chloro-5-(2-ethoxy-2-oxoethyl)phenyl]-N-[2,3,5,6-tetrafluoro-4-(trifluoromethyl)phenyl]-acetamide Column chromatography using hexanes/EtOAc (3/1) as the eluent provided the pure product as a white solid (63% yield). $^1$H NMR (600 MHz, acetone-d$^6$) δ 9.67 (br, 1H, N—H), 7.41 (d, J=2.4 Hz, 1H), 7.40 (d, J=8.4 Hz, 1H), 7.27 (dd, J=8.4, 2.4 Hz, 1H), 4.11 (q, J=7.2 Hz, 2H), 4.04 (s, 2H), 3.65 (s, 2H), 1.21 (t, J=7.2 Hz, 3H); $^{13}$C NMR (150 MHz, acetone-d$^6$) δ 171.39, 168.37, 134.88, 133.92, 133.80, 133.71, 130.81, 130.01, 61.22, 40.92, 40.73, 14.46. HRMS (ESI-TOF) m/z Calcd for C$_{19}$H$_{12}$ClF$_7$NO$_3^-$ [M–H]$^-$ 470.0399, found 470.0400.

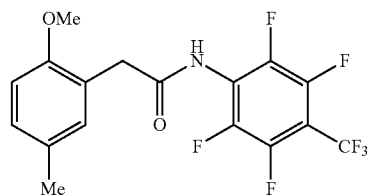

3b 2-(2-Methoxy-5-methylphenyl)-N-[2,3,5,6-tetrafluoro-4-(trifluoromethyl)phenyl]acetamide Column chromatography using hexanes/EtOAc (4/1) as the eluent provided the pure product as a white solid (91% yield). $^1$H NMR (400 MHz, acetonitrile-d$^3$) δ 8.36 (br, 1H, N—H), 7.10 (dd, J=8.4, 2.4 Hz, 1H), 7.07 (d, J=2.4 Hz, 1H), 6.89 (d, J=8.4 Hz, 1H), 3.81 (s, 3H), 3.69 (s, 2H), 2.27 (s, 3H); $^{13}$C NMR (150 MHz, acetonitrile-d$^3$) δ 170.35, 156.43, 132.81, 130.94, 130.09, 123.79, 111.78, 56.24, 38.75, 20.42. HRMS (ESI-TOF) m/z Calcd for C$_{17}$H$_{11}$F$_7$NO$_2^-$ [M–H]$^-$ 394.0683, found 394.0684.

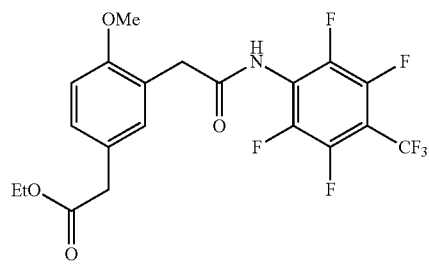

4b

2-[2-Methoxy-5-(2-ethoxy-2-oxoethyl)phenyl]-N-[2,3,5,6-tetrafluoro-4-(trifluoromethyl)phenyl]-acetamide 15 mol % of Pd(OAc)$_2$ and 30 mol % of L19 were used in the reaction. Preparative TLC using hexanes/EtOAc (4/1) as the eluent provided the pure product as a white solid (73% yield). $^1$H NMR (400 MHz, CDCl$_3$) δ 7.81 (br, 1H, N—H), 7.26 (dd, J=8.4, 2.4 Hz, 1H), 7.22 (d, J=2.4 Hz, 1H), 6.93 (d, J=8.4 Hz, 1H), 4.15 (q, J=7.2 Hz, 2H), 3.94 (s, 3H), 3.78 (s, 2H), 3.57 (s, 2H), 1.26 (t, J=7.2 Hz, 3H); $^{13}$C NMR (150 MHz, CDCl$_3$) δ 171.85, 168.86, 155.99, 132.64, 130.49, 127.51, 122.42, 111.13, 61.14, 55.86, 40.39, 39.48, 14.33. HRMS (ESI-TOF) m/z Calcd for C$_{20}$H$_{15}$F$_7$NO$_4^-$ [M–H]$^-$ 466.0895, found 466.0895.

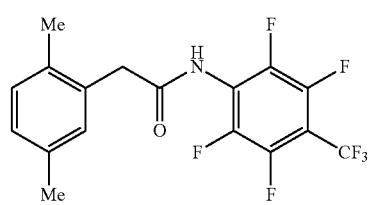

3c

2-(2,5-Dimethylphenyl)-N-[2,3,5,6-tetrafluoro-4-(trifluoromethyl)phenyl]acetamide Column chromatography using hexanes/EtOAc (4/1) as the eluent provided the pure product as a white solid (90% yield). $^1$H NMR (400 MHz, acetone-d$^6$) δ 9.38 (br, 1H, N—H), 7.13 (s, 1H), 7.07 (d, J=7.6 Hz, 1H), 6.99 (d, J=7.6 Hz, 1H), 3.85 (s, 2H), 2.30 (s, 3H), 2.27 (s, 3H); $^{13}$C NMR (150 MHz, acetone-d$^6$) δ 169.60, 136.11, 134.78, 134.05, 131.88, 130.98, 128.77, 41.22, 20.92, 19.17. HRMS (ESI-TOF) m/z Calcd for C$_{17}$H$_{11}$F$_7$NO$^-$ [M–H]$^-$ 378.0734, found 378.0737.

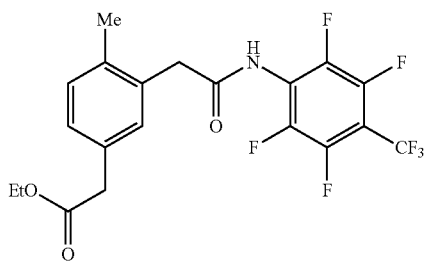

4c

2-[2-Methyl-5-(2-ethoxy-2-oxoethyl)phenyl]-N-[2,3,5,6-tetrafluoro-4-(trifluoromethyl)phenyl]acetamide Column chromatography using hexanes/EtOAc (4/1) as the eluent provided the pure product as a white solid (84% yield). $^1$H NMR (400 MHz, acetone-d$^6$) δ 7.23 (d, J=1.6 Hz, 1H), 7.16 (d, J=8.0 Hz, 1H), 7.12 (dd, J=8.0, 1.6 Hz, 1H), 4.09 (q, J=7.2 Hz, 2H), 3.90 (s, 2H), 3.57 (s, 2H), 2.33 (s, 3H), 1.20 (t, J=7.2 Hz, 3H); $^{13}$C NMR (150 MHz, acetone-d$^6$) δ 171.80, 169.39, 136.57, 134.37, 133.32, 132.05, 131.12, 129.06, 61.02, 41.16, 41.13, 19.29, 14.48. HRMS (ESI-TOF) m/z Calcd for C$_{20}$H$_{15}$F$_7$NO$_3^-$ [M–H]$^-$ 450.0946, found 450.0946.

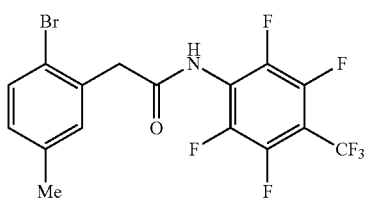

3d

2-(2-Bromo-5-methylphenyl)-N-[2,3,5,6-tetrafluoro-4-(trifluoromethyl)phenyl]acetamide Column chromatography using hexanes/EtOAc (4/1) as the eluent provided the pure product as a white solid (88% yield). $^1$H NMR (400 MHz, acetone-d$^6$) δ 7.48 (d, J=8.0 Hz, 1H), 7.30 (d, J=2.0 Hz, 1H), 7.06 (dd, J=8.0, 2.0 Hz, 1H), 4.01 (s, 2H), 2.30 (s, 3H); $^{13}$C NMR (150 MHz, acetone-d$^6$) δ 168.39, 138.51, 135.30, 133.72, 133.18, 130.70, 122.28, 43.40, 20.79. HRMS (ESI-TOF) m/z Calcd for C$_{16}$H$_8$BrF$_7$NO$^-$ [M–H]$^-$ 441.9683, found 441.9683.

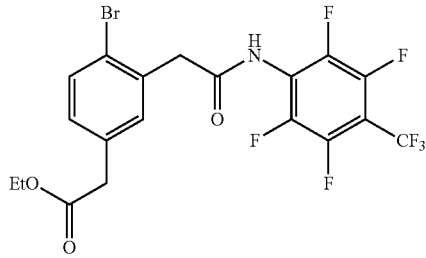

4d

2-[2-Bromo-5-(2-ethoxy-2-oxoethyl)phenyl]-N-[2,3,5,6-tetrafluoro-4-(trifluoromethyl)phenyl]acetamide Column chromatography using hexanes/EtOAc (4/1) as the eluent provided the pure product as a white solid (81% yield). $^1$H NMR (400 MHz, acetone-d$^6$) δ 7.57 (d, J=8.4 Hz, 1H), 7.41 (d, J=2.4 Hz, 1H), 7.19 (dd, J=8.4, 2.4 Hz, 1H), 4.11 (q, J=7.2 Hz, 2H), 4.05 (s, 2H), 3.64 (s, 2H), 1.21 (t, J=7.2 Hz, 3H); $^{13}$C NMR (150 MHz, acetone-d$^6$) δ 171.31, 168.29, 135.62, 135.53, 134.00, 133.37, 131.04, 124.01, 61.24, 43.38, 40.78, 14.46. HRMS (ESI-TOF) m/z Calcd for C$_{19}$H$_{12}$BrF$_7$NO$_3^-$ [M–H]$^-$ 513.9894, found 513.9895.

3e

2-(2-Fluoro-5-methylphenyl)-N-[2,3,5,6-tetrafluoro-4-(trifluoromethyl)phenyl]acetamide Column chromatography using hexanes/EtOAc (4/1) as the eluent provided the pure product as a white solid (86% yield). $^1$H NMR (600 MHz, acetone-d$^6$) δ 9.65 (br, 1H, N—H), 7.23 (d, J=6.6 Hz, 1H), 7.15-7.11 (m, 1H), 7.01 (t, J=9.0 Hz, 1H), 3.90 (s, 2H), 2.30 (s, 3H); $^{13}$C NMR (150 MHz, acetone-d$^6$) δ 168.68, 160.28 (d, J=241.5 Hz), 134.49 (d, J=3.0 Hz), 133.11 (d, J=3.0 Hz), 130.33 (d, J=7.5 Hz), 122.42 (d, J=15.0 Hz), 115.59 (d, J=22.5 Hz), 36.34, 20.57. HRMS (ESI-TOF) m/z Calcd for C$_{16}$H$_8$F$_8$NO$^-$ [M–H]$^-$ 382.0484, found 382.0484.

4e

2-[2-Fluoro-5-(2-ethoxy-2-oxoethyl)phenyl]-N-[2,3,5,6-tetrafluoro-4-(trifluoromethyl)phenyl]-acetamide Column chromatography using hexanes/EtOAc (4/1) as the eluent provided the pure product as a white solid (68% yield). $^1$H NMR (400 MHz, acetone-d$^6$) δ 9.70 (br, 1H, N—H), 7.36 (dd, J=7.2, 2.4 Hz, 1H), 7.30-7.25 (m, 1H), 7.09 (dd, J=8.4, 9.6 Hz, 1H), 4.10 (q, J=7.2 Hz, 2H), 3.94 (s, 2H), 3.63 (s, 2H), 1.21 (t, J=7.2 Hz, 3H); $^{13}$C NMR (150 MHz, acetone-d$^6$) δ 171.64, 168.52, 161.13 (d, J=243.0 Hz), 133.62 (d, J=4.5 Hz), 131.73 (d, J=4.5 Hz), 130.98 (d, J=7.5 Hz), 122.78 (d, J=16.5 Hz), 115.83 (d, J=21.0 Hz), 61.15, 40.61, 36.32, 14.47. HRMS (ESI-TOF) m/z Calcd for $C_{19}H_{12}F_8NO_3^-$ [M−H]$^-$ 454.0695, found 454.0695.

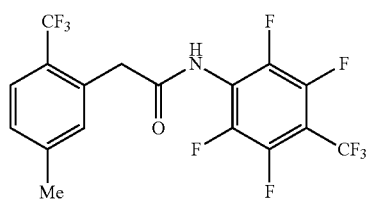

3f

2-(2-Trifluoromethyl-5-methylphenyl)-N-[2,3,5,6-tetrafluoro-4-(trifluoromethyl)phenyl]acetamide Preparative TLC using hexanes/EtOAc (4/1) as the eluent provided the pure product as a white solid (72% yield). $^1$H NMR (600 MHz, acetone-d$^6$) δ 9.64 (br, 1H, N—H), 7.61 (d, J=8.4 Hz, 1H), 7.41 (s, 1H), 7.32 (d, J=8.4 Hz, 1H), 4.10 (s, 2H), 2.41 (s, 3H); $^{13}$C NMR (150 MHz, acetone-d$^6$) δ 168.66, 143.53, 134.86, 133.62, 129.02, 126.77 (q, J=6.0 Hz), 39.87, 21.20 (two carbons are missing due to the F splitting and the signal overlapping). HRMS (ESI-TOF) m/z Calcd for $C_{17}H_8F_{10}NO^-$ [M−H]$^-$ 432.0452, found 432.0452.

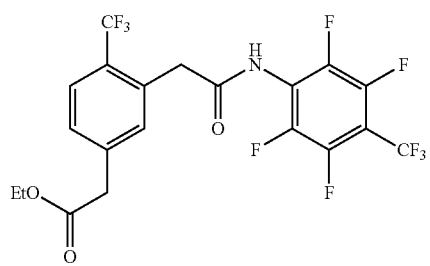

4f

2-[2-Trifluoromethyl-5-(2-ethoxy-2-oxoethyl)phenyl]-N-[2,3,5,6-tetrafluoro-4-(trifluoromethyl)phenyl]-acetamide 15 mol % of Pd(OAc)$_2$ and 30 mol % of ligand L19 were used in the reaction. Preparative TLC using hexanes/EtOAc (4/1) as the eluent provided the pure product as a white solid (75% yield). $^1$H NMR (400 MHz, acetone-d$^6$) δ 9.68 (br, 1H, N—H), 7.70 (d, J=8.0 Hz, 1H), 7.52 (s, 1H), 7.46 (d, J=8.0 Hz, 1H), 4.14 (s, 2H), 4.13 (q, J=7.2 Hz, 2H), 3.76 (s, 2H), 1.22 (t, J=7.2 Hz, 3H); $^{13}$C NMR (150 MHz, acetone-d$^6$) δ 171.06, 168.52, 140.24, 135.21, 133.88, 129.54, 127.99 (q, J=28.5 Hz), 126.90 (q, J=6.0 Hz), 125.63 (q, J=271.5 Hz), 61.36, 41.06, 39.85, 14.45. HRMS (ESI-TOF) m/z Calcd for $C_{20}H_{14}F_{10}NO_3^+$ [M+H]$^+$ 506.0809, found 506.0814.

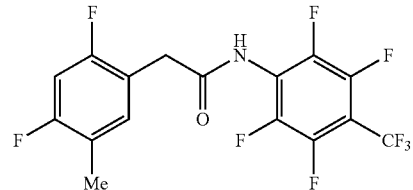 [SMILES: Cc1cc(CC(=O)Nc2c(F)c(F)c(C(F)(F)F)c(F)c2F)c(F)cc1F]

2-(2,4-Difluoro-5-methylphenyl)-N-[2,3,5,6-tetrafluoro-4-(trifluoromethyl)phenyl]acetamide 15 mol % of Pd(OAc)$_2$ and 30 mol % of ligand L19 were used in the reaction. Preparative TLC using hexanes/EtOAc (4/1) as the eluent provided the pure product as a white solid (87% yield). $^1$H NMR (400 MHz, acetone-d$^6$) δ 9.73 (br, 1H, N—H), 7.32 (t, J=8.4 Hz, 1H), 6.96 (t, J=10.0 Hz, 1H), 3.89 (s, 2H), 2.22 (s, 3H); $^{13}$C NMR (150 MHz, acetone-d$^6$) δ 168.57, 161.05 (dd, J=243.0, 12.0 Hz), 160.21 (dd, J 244.5, 12.0 Hz), 134.78 (t, J=6.0 Hz), 121.28 (dd, J=16.5, 3.0 Hz), 118.59 (dd, J=15.0, 4.5 Hz), 103.79 (t, J=25.5 Hz), 35.68, 13.81. HRMS (ESI-TOF) m/z Calcd for $C_{16}H_7F_9NO^-$ [M−H]$^-$ 400.0389, found 400.0390.

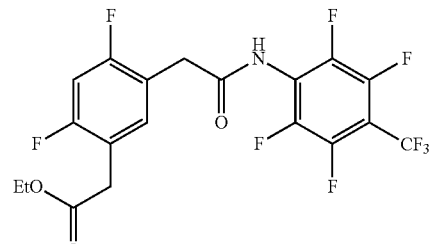

4g

2-[2,4-Difluoro-5-(2-ethoxy-2-oxoethyl)phenyl]-N-[2,3,5,6-tetrafluoro-4-(trifluoromethyl)phenyl]-acetamide 15 mol % of Pd(OAc)$_2$ and 30 mol % of ligand L19 were used in the reaction. Preparative TLC using hexanes/EtOAc (4/1) as the eluent provided the pure product as a white solid (72% yield). $^1$H NMR (600 MHz, acetone-d$^6$) δ 9.72 (br, 1H, N—H), 7.42 (t, J=8.4 Hz, 1H), 7.04 (t, J=9.6 Hz, 1H), 4.13 (q, J=7.2 Hz, 2H), 3.94 (s, 2H), 3.68 (s, 2H), 1.22 (t, J=7.2 Hz, 3H); $^{13}$C NMR (150 MHz, acetone-d$^6$) δ 170.69, 168.36, 161.22 (dd, J=246.0, 6.0 Hz), 161.14 (dd, J=244.5, 6.0 Hz), 135.23 (t, J=6.0 Hz), 119.05 (dd, J=16.5, 3.0 Hz), 118.94 (dd, J=16.5, 3.0 Hz), 104.11 (t, J=27.0 Hz), 61.37, 35.70, 34.34, 14.45. HRMS (ESI-TOF) m/z Calcd for $C_{19}H_{11}F_9NO_3^-$ [M−H]$^-$ 472.0601, found 472.0602.

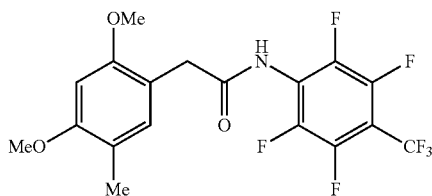

2-(2,4-Dimethoxy-5-methylphenyl)N-[2,3,5,6-tetra-fluoro-4-(trifluoromethyl)phenyl]acetamide 15 mol % of Pd(OAc)$_2$ and 30 mol % of ligand L19 were used in the reaction. Preparative TLC using hexanes/EtOAc (4/1) as the eluent provided the pure product as a white solid (58% yield). $^1$H NMR (600 MHz, CDCl$_3$) δ 7.77 (s, 1H), 7.04 (s, 1H), 6.50 (s, 1H), 3.94 (s, 3H), 3.87 (s, 3H), 3.69 (s, 2H), 2.15 (s, 3H); $^{13}$C NMR (150 MHz, CDCl$_3$) δ 169.62, 158.62, 155.87, 133.18, 119.51, 113.20, 95.16, 55.89, 55.73, 38.68, 15.37. HRMS (ESI-TOF) m/z Calcd for C$_{18}$H$_{15}$F$_7$NO$_3$$^+$ [M+H]$^+$ 426.0935, found 426.0934.

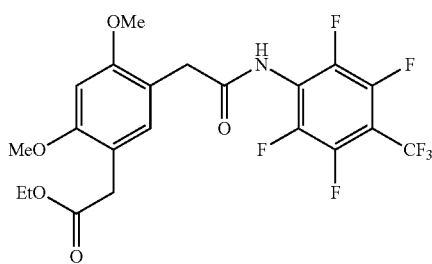

2-[2,4-Dimethoxy-5-(2-ethoxy-2-oxoethyl)phenyl]-N-[2,3,5,6-tetrafluoro-4-(trifluoromethyl)phenyl]-acetamide 15 mol % of Pd(OAc)$_2$ and 30 mol % of ligand L19 were used in the reaction. Preparative TLC using hexanes/EtOAc (4/1) as the eluent provided the pure product as a white solid (70% yield). $^1$H NMR (400 MHz, acetone-d$^6$) δ 9.24 (s, 1H, N—H), 7.10 (s, 1H), 6.71 (s, 1H), 4.08 (q, J=7.2 Hz, 2H), 3.90 (s, 3H), 3.85 (s, 3H), 3.71 (s, 2H), 3.51 (s, 2H), 1.20 (t, J=7.2 Hz, 3H); $^{13}$C NMR (150 MHz, acetone-d$^6$) δ 172.02, 169.91, 159.03, 158.67, 133.92, 115.93, 115.25, 96.40, 60.72, 56.12, 56.09, 37.83, 35.54, 14.57. HRMS (ESI-TOF) m/z Calcd for C$_{21}$H$_{19}$F$_7$NO$_5$$^+$ [M+H]$^+$ 498.1146, found 498.1145.

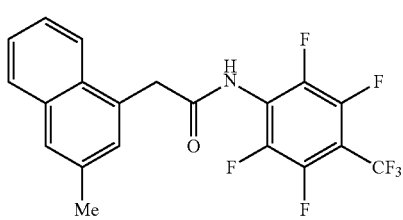

2-(3-Methylnaphthalen-1-yl)-N-[2,3,5,6-tetrafluoro-4-(trifluoromethyl)phenyl]acetamide Preparative TLC using hexanes/EtOAc (4/1) as the eluent provided the pure product as a white solid (84% yield). $^1$H NMR (400 MHz, CDCl$_3$) δ 7.94-7.90 (m, 1H), 7.85-7.81 (m, 1H), 7.68 (s, 1H), 7.55-7.50 (m, 2H), 7.38 (s, 1H), 6.76 (s, 1H), 4.24 (s, 2H), 2.55 (s, 3H); $^{13}$C NMR (150 MHz, CDCl$_3$) δ 168.99, 135.58, 134.55, 131.23, 130.16, 129.45, 128.51, 128.43, 126.85, 126.61, 123.23, 41.81, 21.67. HRMS (ESI-TOF) m/z Calcd for C$_{20}$H$_{11}$F$_7$NO$^-$ [M−H]$^-$ 414.0734, found 414.0741.

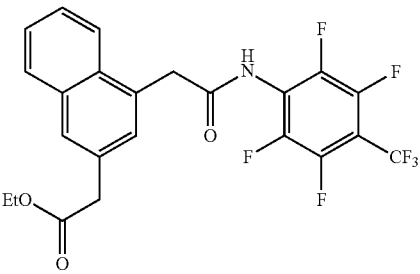

2-[3-(2-ethoxy-2-oxoethyl)naphthalen-1-yl]-N-[2,3,5,6-tetrafluoro-4-(trifluoromethyl)phenyl]-acetamide Preparative TLC using hexanes/EtOAc (4/1) as the eluent provided the pure product as a white solid (72% yield). $^1$H NMR (400 MHz, CDCl$_3$) δ 7.96 (d, J=8.0 Hz, 1H), 7.88 (d, J=8.0 Hz, 1H), 7.78 (s, 1H), 7.62-7.53 (m, 2H), 7.49 (s, 1H), 6.98 (s, 1H), 4.26 (s, 2H), 4.19 (q, J=7.2 Hz, 2H), 3.82 (s, 2H), 1.29 (t, J=7.2 Hz, 3H); $^{13}$C NMR (150 MHz, CDCl$_3$) 171.70, 168.85, 134.29, 131.68, 131.04, 130.50, 130.14, 129.49, 128.92, 127.42, 127.11, 123.39, 61.38, 41.87, 41.28, 14.34. HRMS (ESI-TOF) m/z Calcd for C$_{23}$H$_{15}$F$_7$NO$_3$$^-$ [M−H]$^-$ 486.0946, found 486.0950.

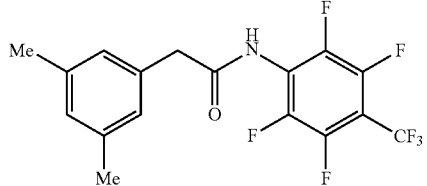

2-(3,5-Dimethylphenyl)-N-[2,3,5,6-tetrafluoro-4-(trifluoromethyl)phenyl]acetamide Preparative TLC using hexanes/EtOAc (4/1) as the eluent provided the pure product as a white solid (80% yield). $^1$H NMR (400 MHz, acetone-d$^6$) δ 6.99 (s, 2H), 6.91 (s, 1H), 3.78 (s, 2H), 2.27 (s, 6H); $^{13}$C NMR (150 MHz, acetone-d$^6$) δ 169.64, 138.68, 135.53, 129.29, 127.85, 43.12, 21.26. HRMS (ESI-TOF) m/z Calcd for C$_{17}$H$_{11}$F$_7$NO$^-$ [M−H]$^-$ 378.0734, found 378.0740.

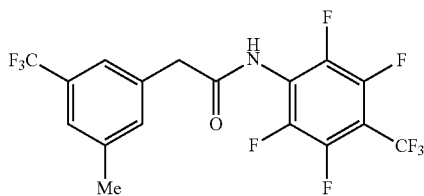

3k

2-[3-Trifluoromethyl-5-methylphenyl]-N-[2,3,5,6-tetrafluoro-4-(trifluoromethyl)phenyl]acetamide 20 mol % of Pd(OAc)$_2$ and 40 mol % of ligand L19 were used in the reaction. Preparative TLC using hexanes/EtOAc (4/1) as the eluent provided the pure product as a white solid (72% yield). $^1$H NMR (400 MHz, acetone-d$^6$) δ 9.71 (br, 1H, N—H), 7.54 (s, 1H), 7.50 (s, 1H), 7.45 (s, 1H), 3.99 (s, 2H), 2.43 (s, 3H); $^{13}$C NMR (150 MHz, acetone-d$^6$) δ 169.09, 140.35, 137.03, 134.83, 130.99 (q, J=31.5 Hz), 125.36 (q, J=270.0 Hz), 125.08 (q, J=3.0 Hz), 124.01 (q, J=3.0 Hz), 42.52, 21.16. HRMS (ESI-TOF) m/z Calcd for C$_{17}$H$_8$F$_{10}$NO$^-$ [M−H]$^-$ 432.0452, found 432.0450.

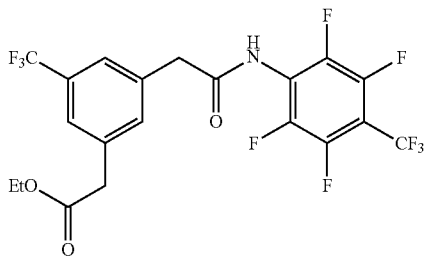

4k

2-[3-Trifluoromethyl-5-(2-ethoxy-2-oxoethyl)phenyl]-N-[2,3,5,6-tetrafluoro-4-(trifluoromethyl)-phenyl]acetamide 20 mol % of Pd(OAc)$_2$ and 40 mol % of ligand L19 were used in the reaction. Preparative TLC using hexanes/EtOAc (4/1) as the eluent provided the pure product as a white solid (51% yield). $^1$H NMR (400 MHz, acetone-d$^6$) δ 9.77 (br, 1H, N—H), 7.66 (s, 1H), 7.61 (s, 1H), 7.60 (s, 1H), 4.13 (q, J=7.2 Hz, 2H), 4.04 (s, 2H), 3.79 (s, 2H), 1.22 (t, J=7.2 Hz, 3H); $^{13}$C NMR (150 MHz, acetone-d$^6$) δ 171.23, 168.96, 137.27, 135.24, 131.04 (q, J=31.5 Hz), 125.71 (q, J=3.0 Hz), 125.46 (q, J=3.0 Hz), 61.35, 42.43, 40.89, 14.45 (two carbons are missing due to the F splitting and the signal overlapping). HRMS (ESI-TOF) m/z Calcd for C$_{20}$H$_{12}$F$_{10}$NO$_3^-$ [M−H]$^-$ 504.0663, found 504.0662.

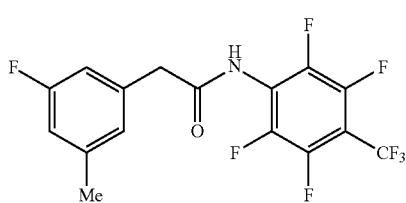

31

2-(3-Fluoro-5-methylphenyl)-N-[2,3,5,6-tetrafluoro-4-(trifluoromethyl)phenyl]acetamide 15 mol % of Pd(OAc)$_2$ and 30 mol % of ligand L19 were used in the reaction. Column chromatography using hexanes/EtOAc (4/1) as the eluent provided the pure product as a white solid (90% yield). $^1$H NMR (400 MHz, acetone-d$^6$) δ 9.64 (br, 1H, N—H), 7.04 (s, 1H), 6.97 (d, J=10.0 Hz, 1H), 6.88 (d, J=10.0 Hz, 1H), 3.87 (s, 2H), 2.34 (s, 3H); $^{13}$C NMR (150 MHz, acetone-d$^6$) δ 169.12, 163.64 (d, J=241.5 Hz), 141.53 (d, J=7.5 Hz), 137.99 (d, J=9.0 Hz), 126.87 (d, J=3.0 Hz), 115.11 (d, J=21.0 Hz), 113.90 (d, J=21.0 Hz), 42.67, 21.20. HRMS (ESI-TOF) m/z Calcd for C$_{16}$H$_{10}$F$_8$NO$^+$ [M+H]$^+$ 384.0629, found 384.0630.

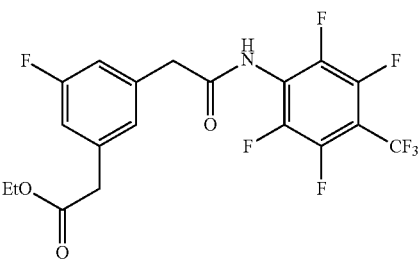

4l

2-[3-Fluoro-5-(2-ethoxy-2-oxoethyl)phenyl]-N-[2,3,5,6-tetrafluoro-4-(trifluoromethyl)phenyl]-acetamide Preparative TLC using hexanes/EtOAc (4/1) as the eluent provided the pure product as a white solid (86% yield). $^1$H NMR (400 MHz, acetone-d$^6$) δ 9.68 (s, 1H, N—H), 7.15 (s, 1H), 7.09 (d, J=10.0 Hz, 1H), 7.04 (d, J=10.0 Hz, 1H), 4.12 (q, J=7.2 Hz, 2H), 3.92 (s, 2H), 3.68 (s, 2H), 1.22 (t, J=7.2 Hz, 3H); $^{13}$C NMR (150 MHz, acetone-d$^6$) δ 171.24, 168.98, 163.49 (d, J=241.5 Hz), 138.30 (d, J=7.5 Hz), 138.25 (d, J=9.0 Hz), 127.24 (d, J=1.5 Hz), 115.67 (d, J=21.0 Hz), 115.43 (d, J=21.0 Hz), 61.28, 42.58, 41.05, 14.45. HRMS (ESI-TOF) m/z Calcd for C$_{19}$H$_{14}$F$_8$NO$_3^+$ [M+H]$^+$ 456.0840, found 456.0843.

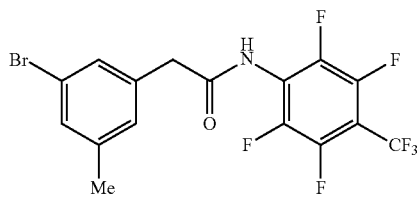

3m 2-(3-Bromo-5-methylphenyl)-N-[2,3,5,6-tetrafluoro-4-(trifluoromethyl)phenyl]acetamide 15 mol % of Pd(OAc)$_2$ and 30 mol % of ligand L19 were used in the reaction. Preparative TLC using hexanes/EtOAc (4/1) as the eluent provided the pure product as a white solid (56% yield). $^1$H NMR (400 MHz, acetone-d$^6$) δ 9.67 (br, 1H, N—H), 7.39 (s, 1H), 7.31 (s, 1H), 7.20 (s, 1H), 3.87 (s, 2H), 2.33 (s, 3H); $^{13}$C NMR (150 MHz, acetone-d$^6$) δ 169.07, 141.46, 138.06, 131.31, 130.12, 129.94, 122.59, 42.45, 21.00. HRMS (ESI-TOF) m/z Calcd for C$_{16}$H$_8$BrF$_7$NO$^-$ [M−H]$^-$ 441.9683, found 441.9685.

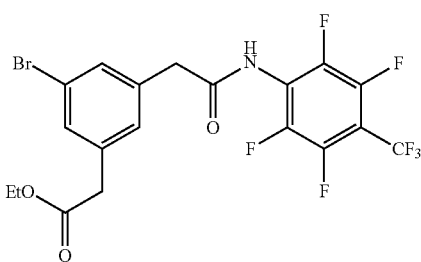

4m

2-[3-Bromo-5-(2-ethoxy-2-oxoethyl)phenyl]-N-[2,3,5,6-tetrafluoro-4-(trifluoromethyl)phenyl]acetamide 15 mol % of Pd(OAc)$_2$ and 30 mol % of ligand L19 were used in the reaction. Preparative TLC using hexanes/EtOAc (4/1) as the eluent provided the pure product as a white solid (47% yield). $^1$H NMR (400 MHz, acetone-d$^6$) δ 9.73 (s, 1H, N—H), 7.50 (s, 1H), 7.44 (s, 1H), 7.32 (s, 1H), 4.12 (q, J=7.2 Hz, 2H), 3.91 (s, 2H), 3.67 (s, 2H), 1.21 (t, J=7.2 Hz, 3H); $^{13}$C NMR (150 MHz, acetone-d$^6$) δ 171.24, 168.97, 138.26, 131.80, 131.58, 130.31, 122.54, 61.31, 42.39, 40.83, 14.45. HRMS (ESI-TOF) m/z Calcd for C$_{19}$H$_{12}$BrF$_7$NO$_3^-$ [M−H]$^-$ 513.9894, found 513.9900.

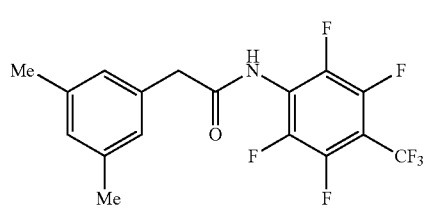

3n

2-(3,5-Dimethylphenyl)-N-[2,3,5,6-tetrafluoro-4-(trifluoromethyl)phenyl]acetamide Product as a white solid (84% yield). Product Compounds 3n and 3j are the same compound.

4n

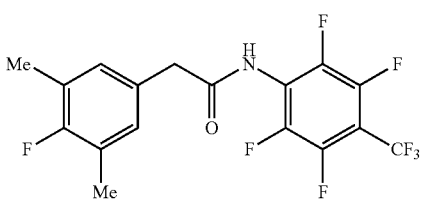

2-[3-Methyl-5-(2-ethoxy-2-oxoethyl)phenyl]-N-[2,3,5,6-tetrafluoro-4-(trifluoromethyl)phenyl]-acetamide Column chromatography using hexanes/EtOAc (4/1) as the eluent provided the pure product as a white solid (32% yield). $^1$H NMR (400 MHz, acetone-d$^6$) δ 7.11 (s, 2H), 7.04 (s, 1H), 4.10 (q, J=7.2 Hz, 2H), 3.82 (s, 2H), 3.58 (s, 2H), 2.31 (s, 3H), 1.21 (t, J=7.2 Hz, 3H); $^{13}$C NMR (150 MHz, acetone-d$^6$) δ 171.71, 169.48, 138.94, 135.80, 129.55, 129.33, 128.09, 61.05, 43.02, 41.47, 21.27, 14.48. HRMS (ESI-TOF) m/z Calcd for C$_{20}$H$_{15}$F$_7$NO$_3^-$ [M−H]$^-$ 450.0946, found 450.0948.

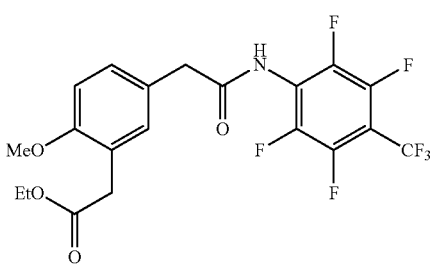

4o

2-[4-Methoxy-3-(2-ethoxy-2-oxoethyl)phenyl]-N-[2,3,5,6-tetrafluoro-4-(trifluoromethyl)phenyl]-acetamide 20 mol % of Pd(OAc)$_2$ and 40 mol % of ligand L19 were used in the reaction. Preparative TLC using hexanes/EtOAc (4/1) as the eluent provided the pure product as a white solid (68% yield). $^1$H NMR (400 MHz, acetone-d$^6$) δ 9.54 (br, 1H, N—H), 7.27 (dd, J=8.0, 2.4 Hz, 1H), 7.21 (d, J=2.4 Hz, 1H), 6.95 (d, J=8.0 Hz, 1H), 4.09 (q, J=7.2 Hz, 2H), 3.81 (s, 3H), 3.79 (s, 2H), 3.57 (s, 2H), 1.20 (t, J=7.2 Hz, 3H); $^{13}$C NMR (150 MHz, acetone-d$^6$) δ 171.67, 169.83, 157.74, 132.64, 129.92, 127.39, 124.51, 111.51, 60.80, 55.92, 42.33, 36.31, 14.54. HRMS (ESI-TOF) m/z Calcd for C$_{20}$H$_{15}$F$_7$NO$_4^-$ [M−H]$^-$ 466.0895, found 466.0900.

3p

2-(4-Fluoro-3,5-dimethylphenyl)-N-[2,3,5,6-tetrafluoro-4-(trifluoromethyl)phenyl]acetamide Preparative TLC using hexanes/EtOAc (4/1) as the eluent provided the pure product as a white solid (85% yield). $^1$H NMR (400 MHz, acetone-d$^6$) δ 9.55 (br, 1H, N—H), 7.06 (d, J=7.2 Hz, 1H), 3.78 (s, 2H), 2.22 (s, 3H), 2.21 (s, 3H); $^{13}$C NMR (150 MHz, acetone-d$^6$) δ 169.66, 159.79 (d, J=240.0 Hz), 130.88 (d, J=4.5 Hz), 130.69 (d, J=6.0 Hz), 124.98 (d, J=18.0 Hz), 42.29, 14.54, 14.51. HRMS (ESI-TOF) m/z Calcd for C$_{17}$H$_{10}$F$_8$NO$^-$ [M−H]$^-$ 396.0640, found 396.0640.

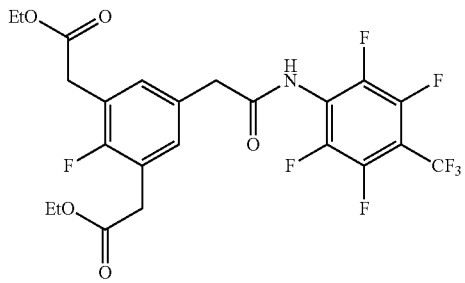

2-[4-Fluoro-3,5-di-(2-ethoxy-2-oxoethyl)phenyl]-N-[2,3,5,6-tetrafluoro-4-(trifluoromethyl)phenyl]-acetamide Preparative TLC using hexanes/EtOAc (4/1) as the eluent provided the pure product as a white solid (59% yield). $^1$H NMR (400 MHz, acetone-d$^6$) δ 9.69 (br, 1H, N—H), 7.27 (d, J=6.8 Hz, 2H), 4.12 (q, J=7.2 Hz, 4H), 3.86 (s, 2H), 3.68 (s, 4H), 1.22 (t, J=7.2 Hz, 6H); $^{13}$C NMR (150 MHz, acetone-d$^6$) δ 170.76, 169.33, 159.54 (d, J=244.5 Hz), 132.32 (d, J=4.5 Hz), 131.34 (d, J=4.5 Hz), 122.84 (d, J=16.5 Hz), 61.30, 42.12, 34.98, 34.96, 14.45. HRMS (ESI-TOF) m/z Calcd for $C_{23}H_{18}F_8NC_5^-$ [M–H]$^-$ 540.1063, found 540.1067.

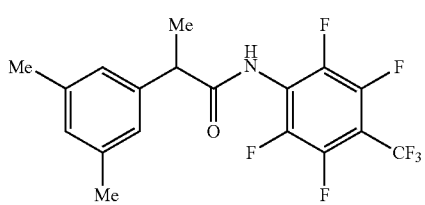

2-(3,5-Dimethylphenyl)-N-[2,3,5,6-tetrafluoro-4-(trifluoromethyl)phenyl]propanamide $^1$H NMR (400 MHz, acetone-d$^6$) Preparative TLC using hexanes/EtOAc (4/1) as the eluent provided the pure product as a white solid (72% yield). δ 9.42 (br, 1H, N—H), 7.01 (s, 2H), 6.91 (s, 1H), 3.96 (q, J=7.2 Hz, 1H), 2.28 (s, 6H), 1.47 (d, J=7.2 Hz, 3H); $^{13}$C NMR (150 MHz, acetone-d$^6$) δ 172.86, 142.05, 138.80, 129.44, 126.13, 46.93, 21.33, 19.46. HRMS (ESI-TOF) m/z Calcd for $C_{18}H_{15}F_7NO^+$ [M+H]$^+$ 394.1036, found 394.1038.

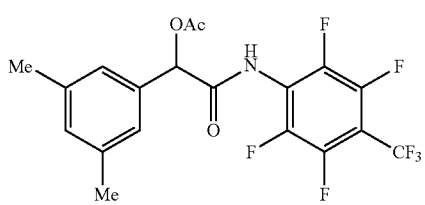

2-Acetoxy-2-(3,5-dimethylphenyl)-N-[2,3,5,6-tetrafluoro-4-(trifluoromethyl)phenyl]acetamide Preparative TLC using hexanes/EtOAc (4/1) as the eluent provided the pure product as a white solid (75% yield). $^1$H NMR (400 MHz, CDCl$_3$) δ 7.56 (s, 1H), 7.10 (s, 2H), 7.05 (s, 1H), 6.23 (s, 1H), 2.34 (s, 6H), 2.25 (s, 3H); $^{13}$C NMR (150 MHz, CDCl$_3$) 169.28, 166.56, 139.07, 133.94, 131.60, 125.51, 75.68, 21.42, 21.11. HRMS (ESI-TOF) m/z Calcd for $C_{19}H_{13}F_7NO_3^-$ [M–H]$^-$ 436.0789, found 436.0786.

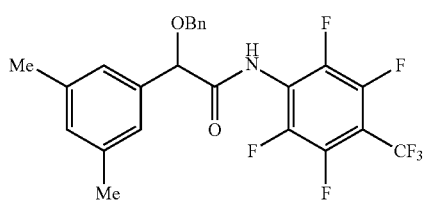

2-(Benzyloxy)-2-(3,5-dimethylphenyl)-N-[2,3,5,6-tetrafluoro-4-(trifluoromethyl)phenyl]acetamide Preparative TLC using hexanes/EtOAc (4/1) as the eluent provided the pure product as a white solid (72% yield). $^1$H NMR (600 MHz, acetone-d$^6$) δ 9.74 (br, 1H, N—H), 7.42 (d, J=7.8 Hz, 2H), 7.38 (t, J=7.8 Hz, 2H), 7.33 (t, J=7.8 Hz, 1H), 7.19 (s, 2H), 7.03 (s, 1H), 5.09 (s, 1H), 4.68 (d, J=11.4 Hz, 1H), 4.65 (d, J=11.4 Hz, 1H), 2.32 (s, 6H); $^{13}$C NMR (150 MHz, acetone-d$^6$) δ 169.84, 138.88, 138.32, 137.75, 131.03, 129.27, 128.94, 128.77, 126.03, 82.60, 72.12, 21.33. HRMS (ESI-TOF) m/z Calcd for $C_{24}H_{17}F_7NO_2^-$ [M–H]$^-$ 484.1153, found 484.1153.

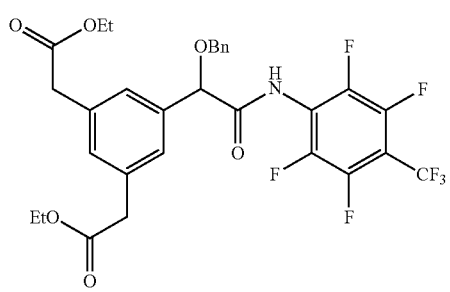

2-(Benzyloxy)-2-[3,5-di-(2-ethoxy-2-oxoethyl)phenyl]-N-[2,3,5,6-tetrafluoro-4-(trifluoromethyl)phenyl]-acetamide Preparative TLC using hexanes/EtOAc (4/1) as the eluent provided the pure product as a white solid (52% yield). $^1$H NMR (400 MHz, acetone-d$^6$) δ 9.81 (br, 1H, N—H), 7.46-7.31 (m, 7H), 7.28 (s, 1H), 5.18 (s, 1H), 4.71 (d, J=11.2 Hz, 1H), 4.67 (d, J=11.2 Hz, 1H), 4.11 (q, J=7.2 Hz, 4H), 3.67 (s, 4H), 1.21 (t, J=7.2 Hz, 6H); $^{13}$C NMR (150 MHz, acetone-d$^6$) δ 171.50, 138.16, 136.22, 131.54, 129.28, 129.10, 128.84, 127.72, 82.23, 72.30, 61.16, 41.44, 14.47. HRMS (ESI-TOF) m/z Calcd for $C_{30}H_{25}F_7NC_6^-$ [M–H]$^-$ 628.1576, found 628.1574.

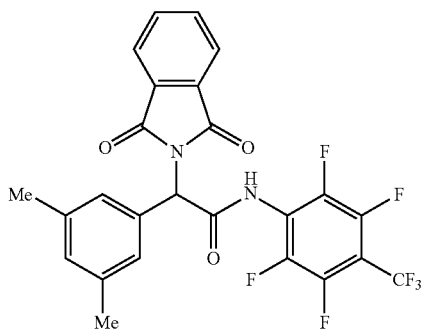

3t

2-(3,5-Dimethylphenyl)-2-(1,3-dioxoisoindolin-2-yl)-N-[2,3,5,6-tetrafluoro-4-(trifluoromethyl)phenyl]-acetamide Preparative TLC using hexanes/EtOAc (4/1) as the eluent provided the pure product as a white solid (82% yield). $^1$H NMR (400 MHz, acetone-d$^6$) δ 9.53 (br, 1H, N—H), 7.95-7.85 (m, 4H), 7.28 (s, 2H), 7.02 (s, 1H), 6.23 (s, 1H), 2.30 (s, 6H); $^{13}$C NMR (150 MHz, acetone-d$^6$) δ 167.87, 166.63, 138.86, 135.54, 135.32, 132.78, 131.04, 128.63, 124.22, 58.08, 21.33. HRMS (ESI-TOF) m/z Calcd for $C_{25}H_{14}F_7N_2O_3^-$ [M–H]$^-$ 523.0898, found 523.0892.

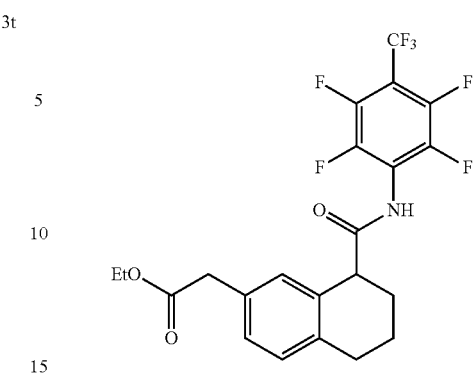

4u

Ethyl 2-(8-{[2,3,5,6-tetrafluoro-4-(trifluoromethyl)-phenyl]carbamoyl}-5,6,7,8-tetrahydronaph-thalen-2-yl)acetate 15 mol % of Pd(OAc)$_2$ and 30 mol % of ligand L19 were used in the reaction. Preparative TLC using hexanes/EtOAc (4/1) as the eluent provided the pure product as a white solid (43% yield). $^1$H NMR (400 MHz, CDCl$_3$) δ 7.20-7.15 (m, 2H), 7.15 (s, 1H), 7.05 (br, 1H, N—H), 4.14 (q, J=7.2 Hz, 2H), 3.92 (t, J=5.6 Hz, 1H), 3.60 (s, 2H), 2.92-2.77 (m, 2H), 2.41-2.33 (m, 1H), 2.13-2.03 (m, 1H), 1.92-1.82 (m, 2H), 1.26 (t, J=7.2 Hz, 3H); $^{13}$C NMR (150 MHz, CDCl$_3$) δ 173.04, 171.80, 137.08, 132.99, 132.77, 130.89, 130.57, 129.28, 61.22, 47.31, 40.83, 28.88, 27.54, 20.41, 14.27. HRMS (ESI-TOF) m/z Calcd for $C_{22}H_{17}F_7NO_3^-$ [M–H]$^-$ 476.1102, found 476.1106.

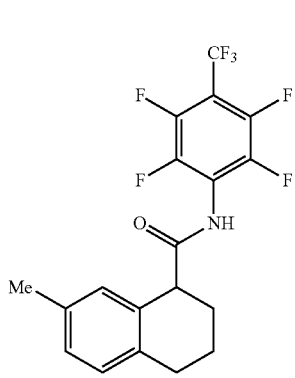

3u

7-Methyl-N-[2,3,5,6-tetrafluoro-4-(trifluoromethyl)-phenyl]-1,2,3,4-tetrahydronaphthalene-1-carboxamide 15 mol % of Pd(OAc)$_2$ and 30 mol % of ligand L19 were used in the reaction. Preparative TLC using hexanes/EtOAc (4/1) as the eluent provided the pure product as a white solid (71% yield). $^1$H NMR (400 MHz, CDCl$_3$) δ 7.13-7.07 (m, 2H), 7.05 (s, 1H), 6.85 (br, 1H, N—H), 3.90 (t, J=5.6 Hz, 1H), 2.90-2.75 (m, 2H), 2.40-2.33 (m, 1H), 2.14-2.04 (m, 1H), 1.91-1.82 (m, 2H); $^{13}$C NMR (150 MHz, CDCl$_3$) δ 173.25, 136.59, 135.15, 132.55, 130.48, 130.28, 129.26, 47.46, 28.77, 27.73, 21.08, 20.53. HRMS (ESI-TOF) m/z Calcd for $C_{19}H_{13}F_7NO^-$ [M–H]$^-$ 404.0891, found 404.0895.

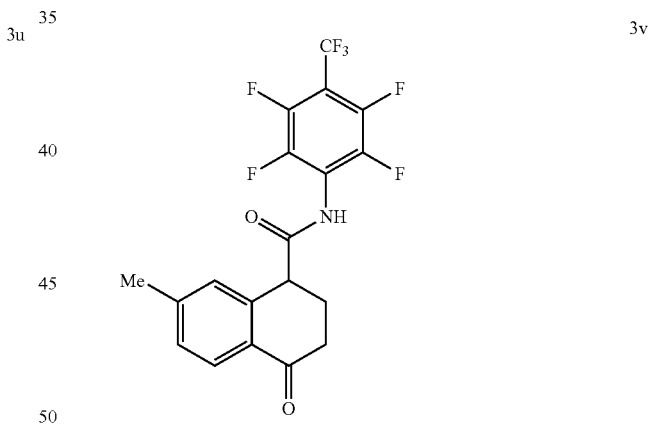

3v

7-Methyl-4-oxo-N-[2,3,5,6-tetrafluoro-4-(trifluoromethyl)phenyl]-1,2,3,4-tetrahydronaphthalene-1-carboxamide 15 mol % of Pd(OAc)$_2$ and 30 mol % of ligand L19 were used in the reaction. Preparative HPLC using C18 column provided the pure product as a white solid (71% yield). $^1$H NMR (400 MHz, acetone-d$^6$) δ 9.79 (br, 1H, N—H), 7.90 (d, J=8.0 Hz, 1H), 7.30 (s, 1H), 7.27 (d, J=8.0 Hz, 1H), 4.34 (t, J=5.6 Hz, 1H), 2.90-2.80 (m, 1H), 2.65-2.56 (m, 1H), 2.55-2.48 (m, 2H), 2.39 (s, 3H); $^{13}$C NMR (150 MHz, acetone-d$^6$) δ 196.25, 171.92, 145.12, 141.93, 131.55, 129.90, 129.59, 127.93, 46.65, 36.14, 27.75, 21.66. HRMS (ESI-TOF) m/z Calcd for $C_{19}H_{11}F_7NO_2^-$ [M–H]$^-$ 418.0683, found 418.0697.

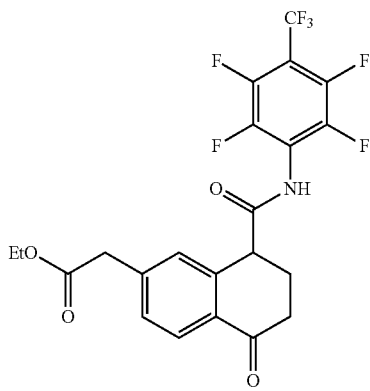

4v

Ethyl 2-(5-Oxo-8-{[2,3,5,6-tetrafluoro-4-(trifluoromethyl)phenyl]carbamoyl}-5,6,7,8-tetrahydro-naphthalen-2-yl)acetate 15 mol % of Pd(OAc)$_2$ and 30 mol % of ligand L19 were used in the reaction. Preparative TLC using hexanes/EtOAc (4/1) as the eluent provided the pure product as a white solid (69% yield). $^1$H NMR (600 MHz, CDCl$_3$) δ 8.11 (d, J=8.0 Hz, 1H), 7.40 (d, J=8.0 Hz, 1H), 7.37 (s, 1H), 7.24 (br, 1H, N—H), 4.17 (q, J=7.2 Hz, 2H), 4.09 (t, J=5.3 Hz, 1H), 3.72 (d, J=15.8 Hz, 1H), 3.69 (d, J=15.8 Hz, 1H), 2.85-2.77 (m, 1H), 2.75-2.69 (m, 2H), 2.52-2.45 (m, 1H), 1.27 (t, J=7.2 Hz, 3H); $^{13}$C NMR (150 MHz, CDCl$_3$) δ 196.06, 170.88, 170.21, 141.21, 139.72, 131.65, 130.39, 130.19, 128.91, 61.64, 46.76, 41.24, 35.77, 26.97, 14.27. HRMS (ESI-TOF) m/z Calcd for $C_{22}H_{15}F_7NC_4^-$ [M–H]$^-$ 490.0895, found 490.0900.

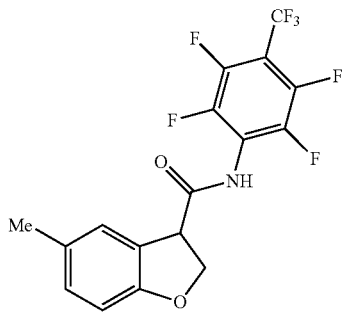

3w

5-Methyl-N-[2,3,5,6-tetrafluoro-4-(trifluoromethyl)-phenyl]-2,3-dihydrobenzofuran-3-carboxamide 20 mol % of Pd(OAc)$_2$ and 40 mol % of ligand L19 were used in the reaction. Preparative TLC using hexanes/EtOAc (4/1) as the eluent provided the pure product as a white solid (81% yield). $^1$H NMR (600 MHz, acetone-d$^6$) δ 9.86 (br, 1H, N—H), 7.28 (s, 1H), 7.01 (d, J=8.2 Hz, 1H), 6.69 (d, J=8.2 Hz, 1H), 4.90 (dd, J=8.8, 6.4 Hz, 1H), 4.76 (t, J=8.8 Hz, 1H), 4.70 (dd, J=8.8, 6.4 Hz, 1H), 2.26 (s, 3H); $^{13}$C NMR (150 MHz, acetone-d$^6$) δ 170.33, 159.14, 130.64, 130.43, 126.53, 125.99, 110.06, 73.83, 49.34, 20.80. HRMS (ESI-TOF) m/z Calcd for $C_{17}H_9F_7NO_2^-$ [M–H]$^-$ 392.0527, found 392.0524.

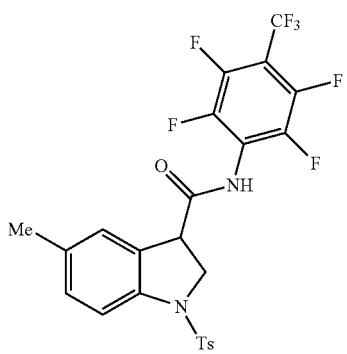

3x

5-Methyl-N-[2,3,5,6-tetrafluoro-4-(trifluoromethyl)-phenyl]-1-tosylindoline-3-carboxamide 20 mol % of Pd(OAc)$_2$ and 40 mol % of ligand L19 were used in the reaction. Preparative TLC using hexanes/EtOAc (3/1) as the eluent provided the pure product as a white solid (73% yield). $^1$H NMR (400 MHz, acetone-d$^6$) δ 9.87 (br, 1H, N—H), 7.77 (d, J=8.4 Hz, 2H), 7.52 (d, J=8.0 Hz, 1H), 7.37 (d, J=8.4 Hz, 2H), 7.24 (s, 1H), 7.13 (d, J=8.0 Hz, 1H), 4.48 (dd, J=7.2, 10.0 Hz, 1H), 4.35 (dd, J=7.2, 10.8 Hz, 1H), 4.28 (dd, J=10.0, 10.8 Hz, 1H), 2.38 (s, 3H), 2.27 (s, 3H); $^{13}$C NMR (150 MHz, acetone-d$^6$) δ 169.65, 145.29, 140.71, 134.83, 134.27, 130.96, 130.62, 130.41, 128.42, 126.34, 115.34, 53.32, 47.11, 21.41, 20.88. HRMS (ESI-TOF) m/z Calcd for $C_{24}H_{16}F_7N_2O_3S^-$ [M–H]$^-$ 545.0775, found 545.0778.

LC-MS Analyses of the Reactions Giving Low Yields:

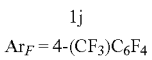

1j

Ar$_F$ = 4-(CF$_3$)C$_6$F$_4$

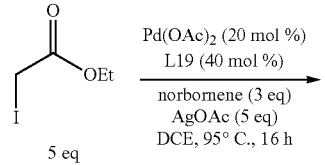

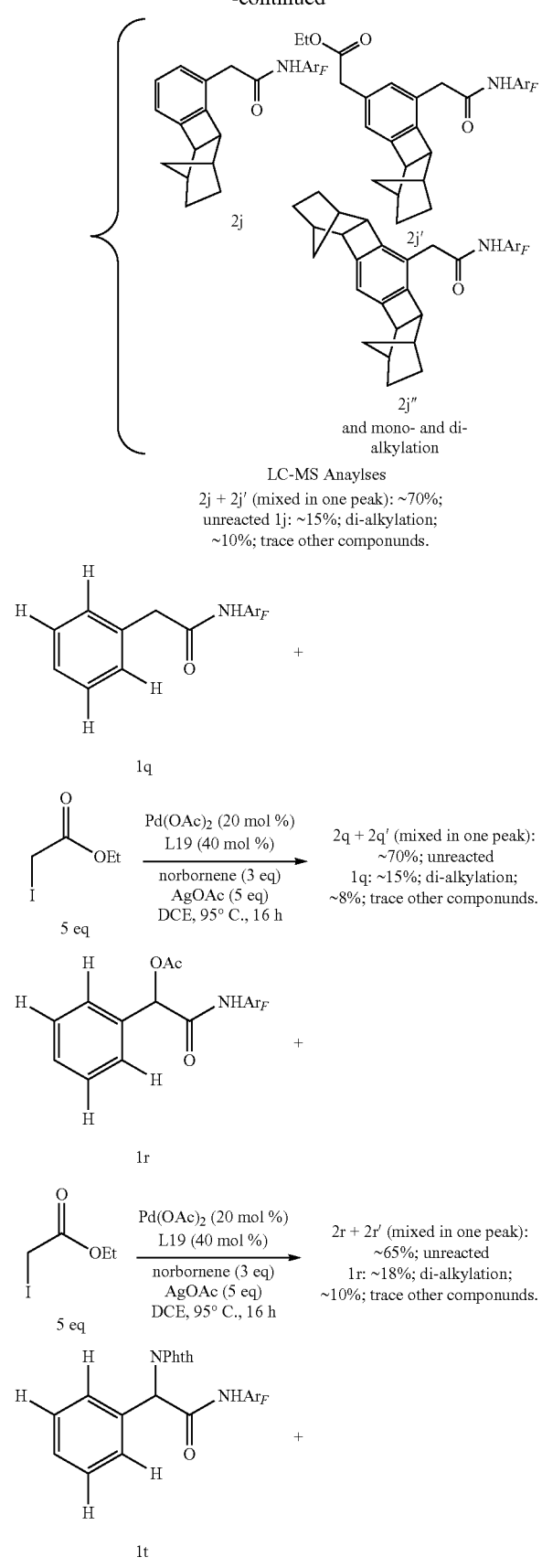
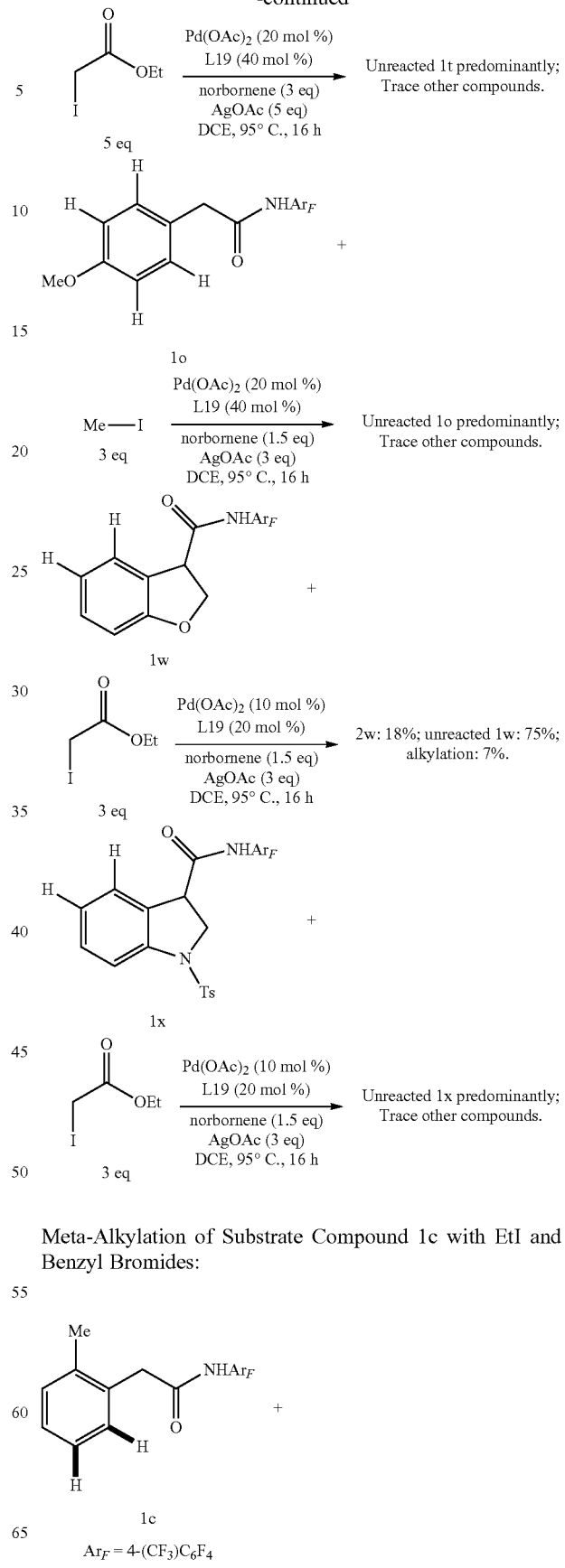
Meta-Alkylation of Substrate Compound 1c with EtI and Benzyl Bromides:
$Ar_F = 4\text{-}(CF_3)C_6F_4$ -continued

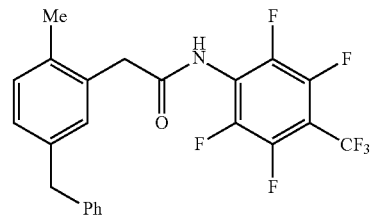

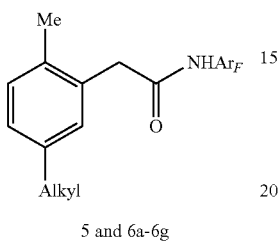

5 and 6a-6g

General Procedure

A 2-dram vial equipped with a magnetic stir bar was charged with the amide substrate (36.5 mg, 0.10 mmol), Pd(OAc)$_2$ (2.2 mg, 10 mol %), ligand L19 (4.1 mg, 20 mol %), AgOAc (50 mg, 0.30 mmol) and norbornene (14.1 mg, 0.15 mmol). Ethyl iodide (48 μL, 0.60 mmol) or a benzyl bromide (0.60 mmol) and 0.70 mL of DCE were then added to the mixture. The vial was capped and closed tightly. The mixture was stirred at 95° C. for 16 hours.

After cooling to room temperature, the mixture was passed through a pad of Celite® with ethyl acetate as the eluent to remove any insoluble compounds. The resulting solution was concentrated, and the residual mixture was dissolved with a minimal amount of acetone and loaded onto a preparative TLC plate. The pure product was then isolated by preparative TLC with ethyl acetate and hexanes as the eluent.

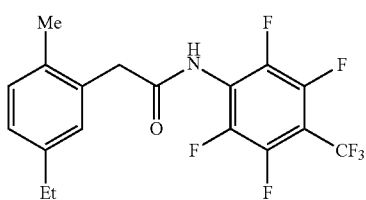

2-(5-Ethyl-2-methylphenyl)-N-[2,3,5,6-tetrafluoro-4-(trifluoromethyl)phenyl]acetamide Preparative TLC using hexanes/EtOAc (4/1) as the eluent provided the pure product as a white solid (21% yield). $^1$H NMR (400 MHz, acetone-d$^6$) δ 9.46 (br, 1H, N—H), 7.17 (d, J=1.6 Hz, 1H), 7.11 (d, J=7.6 Hz, 1H), 7.03 (dd, J=7.6, 1.6 Hz, 1H), 3.87 (s, 2H), 2.58 (q, J=7.6 Hz, 2H), 2.31 (s, 3H), 1.19 (t, J=7.6 Hz, 3H); $^{13}$C NMR (150 MHz, acetone-d$^6$) δ 169.60, 142.69, 135.05, 134.12, 131.05, 130.63, 127.55, 41.26, 28.93, 19.21, 16.08. HRMS (ESI-TOF) m/z Calcd for C$_{18}$H$_{13}$F$_7$NO$^-$ [M–H]$^-$ 392.0891, found 392.0892.

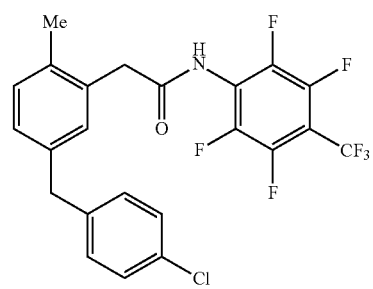

2-(5-Benzyl-2-methylphenyl)-N-[2,3,5,6-tetrafluoro-4-(trifluoromethyl)phenyl]acetamide 15 mol % of Pd(OAc)$_2$ and 30 mol % of ligand L19 were used in the reaction. Preparative TLC using hexanes/EtOAc (4/1) as the eluent provided the pure product as a white solid (66% yield). $^1$H NMR (400 MHz, acetone-d$^6$) δ 9.50 (br, 1H, N—H), 7.30-7.14 (m, 6H), 7.12 (d, J=7.6 Hz, 1H), 7.05 (dd, J=7.6, 1.6 Hz, 1H), 3.93 (s, 2H), 3.87 (s, 2H), 2.31 (s, 3H); $^{13}$C NMR (150 MHz, acetone-d$^6$) δ 169.49, 142.44, 140.04, 135.59, 134.34, 131.67, 131.17, 129.62, 129.20, 128.63, 126.76, 41.98, 41.18, 19.24. HRMS (ESI-TOF) m/z Calcd for C$_{23}$H$_{15}$F$_7$NO$^-$ [M–H]$^-$ 454.1047, found 454.1050.

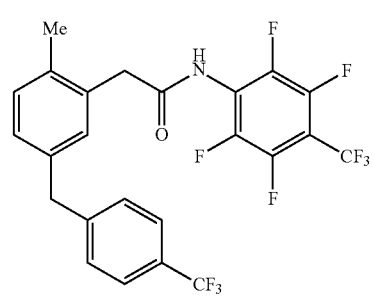

2-[5-(4-Chlorobenzyl)-2-methylphenyl]-N-[2,3,5,6-tetrafluoro-4-(trifluoromethyl)phenyl]acetamide 15 mol % of Pd(OAc)$_2$ and 30 mol % of ligand L19 were used in the reaction. Preparative TLC using hexanes/EtOAc (4/1) as the eluent provided the pure product as a white solid (65% yield). $^1$H NMR (400 MHz, acetone-d$^6$) δ 9.50 (br, 1H, N—H), 7.29 (d, J=8.4 Hz, 2H), 7.24 (d, J=8.4 Hz, 2H), 7.19 (s, 1H), 7.13 (d, J=7.6 Hz, 1H), 7.05 (d, J=7.6 Hz, 1H), 3.93 (s, 2H), 3.87 (s, 2H), 2.31 (s, 3H); $^{13}$C NMR (150 MHz, acetone-d$^6$) δ 169.46, 141.44, 139.51, 135.81, 134.50, 132.12, 131.63, 131.34, 131.26, 129.19, 128.61, 41.16, 41.13, 19.24. HRMS (ESI-TOF) m/z Calcd for C$_{23}$H$_{14}$ClF$_7$NO$^-$ [M–H]$^-$ 488.0658, found 488.0658.

2-[5-(4-Trifluoromethylbenzyl)-2-methylphenyl]-N-[2,3,5,6-tetrafluoro-4-(trifluoromethyl)phenyl]-acetamide DCM was used as solvent instead of DCE. Preparative TLC using hexanes/EtOAc (4/1) as the eluent provided the pure product as a white solid (71% yield). $^1$H NMR (400 MHz, acetone-d$^6$) δ 9.51 (br, 1H, N—H), 7.62 (d, J=8.0 Hz, 2H), 7.47 (d, J=8.0 Hz, 2H), 7.24 (s, 1H), 7.16 (d, J=8.0 Hz, 1H), 7.10 (d, J=8.0 Hz, 1H), 4.06 (s, 2H), 3.89 (s, 2H), 2.33 (s, 3H); $^{13}$C NMR (150 MHz, acetone-d$^6$) δ 169.44, 147.29, 139.00, 136.01, 134.62, 131.71, 131.34, 130.31, 128.71, 126.07 (q, J=3.6 Hz), 41.62, 41.10, 19.25 (two carbons are missing due to the F splitting and the signal overlapping). HRMS (ESI-TOF) m/z Calcd for C$_{24}$H$_{14}$F$_{10}$NO$^-$ [M–H]$^-$ 522.0921, found 522.0922.

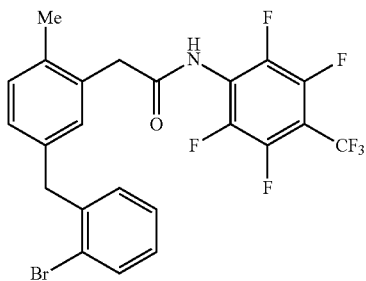

6d

2-[5-(2-Bromobenzyl)-2-methylphenyl]-N-[2,3,5,6-tetrafluoro-4-(trifluoromethyl)phenyl]acetamide Preparative TLC using hexanes/EtOAc (4/1) as the eluent provided the pure product as a white solid (75% yield). $^1$H NMR (400 MHz, acetone-d$^6$) δ 9.51 (br, 1H, N—H), 7.59 (d, J=8.0 Hz, 1H), 7.33-7.25 (m, 2H), 7.21 (s, 1H), 7.18-7.12 (m, 2H), 7.04 (d, J=8.0 Hz, 1H), 4.08 (s, 2H), 3.87 (s, 2H), 2.32 (s, 3H); $^{13}$C NMR (150 MHz, acetone-d$^6$) δ 169.45, 141.42, 138.19, 135.90, 134.44, 133.60, 132.19, 131.76, 131.20, 129.02, 128.69, 128.61, 125.17, 41.68, 41.16, 19.27. HRMS (ESI-TOF) m/z Calcd for C$_{23}$H$_{14}$BrF$_7$NO$^-$ [M–H]$^-$ 532.0152, found 532.0153.

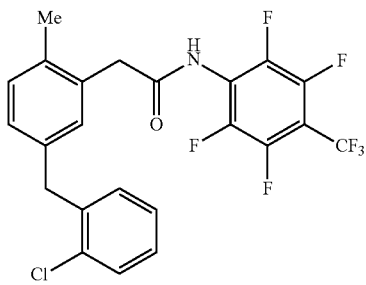

6e

2-[5-(2-Chlorobenzyl)-2-methylphenyl]-N-[2,3,5,6-tetrafluoro-4-(trifluoromethyl)phenyl]acetamide Preparative TLC using hexanes/EtOAc (4/1) as the eluent provided the pure product as a white solid (75% yield). $^1$H NMR (400 MHz, acetone-d$^6$) δ 9.47 (br, 1H, N—H), 7.42-7.38 (m, 1H), 7.30-7.22 (m, 3H), 7.21 (s, 1H), 7.13 (d, J=8.0 Hz, 1H), 7.04 (d, J=8.0 Hz, 1H), 4.07 (s, 2H), 3.87 (s, 2H), 2.32 (s, 3H); $^{13}$C NMR (150 MHz, acetone-d$^6$) δ 169.45, 139.73, 138.22, 135.87, 134.55, 134.43, 132.14, 131.70, 131.19, 130.23, 128.78, 128.64, 127.99, 41.15, 39.14, 19.26. HRMS (ESI-TOF) m/z Calcd for C$_{23}$H$_{14}$ClF$_7$NO$^-$ [M–H]$^-$ 488.0658, found 488.0662.

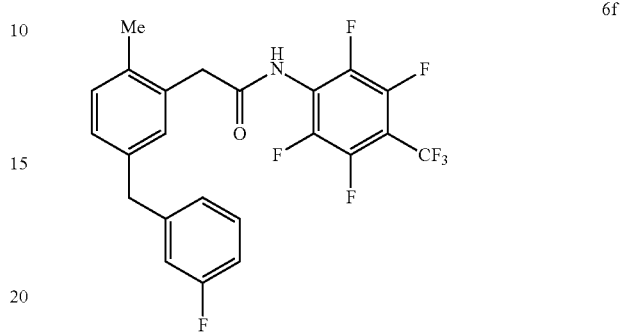

6f

2-[5-(3-Fluorobenzyl)-2-methylphenyl]-N-[2,3,5,6-tetrafluoro-4-(trifluoromethyl)phenyl]acetamide 15 mol % of Pd(OAc)$_2$ and 30 mol % of ligand L19 were used in the reaction. Preparative TLC using hexanes/EtOAc (4/1) as the eluent provided the pure product as a white solid (63% yield). $^1$H NMR (400 MHz, acetone-d$^6$) δ 9.51 (br, 1H, N—H), 7.34-7.26 (m, 1H), 7.22 (s, 1H), 7.14 (d, J=8.0 Hz, 1H), 7.10-7.05 (m, 2H), 7.00-6.90 (m, 2H), 3.96 (s, 2H), 3.88 (s, 2H), 2.32 (s, 3H); $^{13}$C NMR (150 MHz, acetone-d$^6$) δ 169.48, 163.75 (d, J=243.0 Hz), 145.43 (d, J=7.5 Hz), 139.29, 135.88, 134.52, 131.69, 131.28, 130.93 (d, J=7.5 Hz), 128.67, 125.56, 116.22 (d, J=21.0 Hz), 113.45 (d, J=21.0 Hz), 41.54, 41.13, 19.25. HRMS (ESI-TOF) m/z Calcd for C$_{23}$H$_{14}$F$_8$NO$^-$ [M–H]$^-$ 472.0953, found 472.0956.

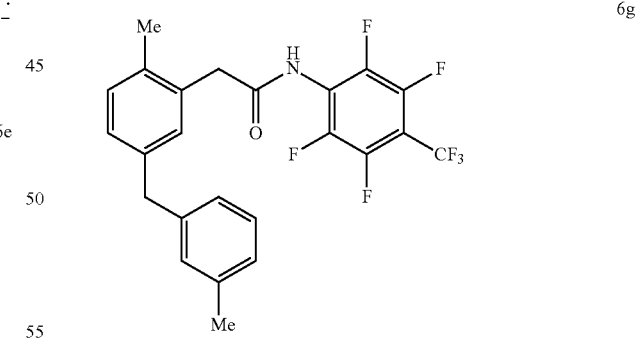

6g

2-[5-(3-Methylbenzyl)-2-methylphenyl]-N-[2,3,5,6-tetrafluoro-4-(trifluoromethyl)phenyl]acetamide 15 mol % of Pd(OAc)$_2$ and 30 mol % of L19 were used in the reaction. Preparative TLC using hexanes/EtOAc (4/1) as the eluent provided the pure product as a white solid (60% yield). $^1$H NMR (400 MHz, acetone-d$^6$) δ 9.48 (br, 1H, N—H), 7.20 (s, 1H), 7.16-7.09 (m, 2H), 7.06-6.96 (m, 4H), 3.88 (s, 2H), 3.86 (s, 2H), 2.31 (s, 3H), 2.26 (s, 3H); $^{13}$C NMR (150 MHz, acetone-d$^6$) δ 169.51, 142.32, 140.16, 138.56, 135.52, 134.31, 131.62, 131.14, 130.34, 129.10, 128.63, 127.44, 126.70, 41.96, 41.18, 21.37, 19.23. HRMS (ESI-TOF) m/z Calcd for $C_{24}H_{17}F_7NO^-$ [M−H]$^-$ 468.1204, found 468.1207.

Meta-Arylation of Substrate 1c with Aryl Iodides

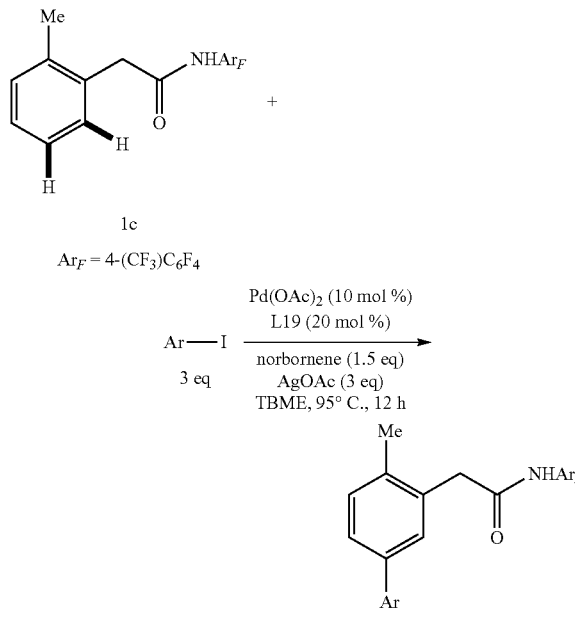

General Procedure

A 2-dram vial equipped with a magnetic stir bar was charged with the amide substrate (36.5 mg, 0.10 mmol), Pd(OAc)$_2$ (2.2 mg, 10 mol %), ligand L19 (4.1 mg, 20 mol %), AgOAc (50 mg, 0.30 mmol) and norbornene (14.1 mg, 0.15 mmol). Aryl iodide (0.30 mmol) and 1.0 mL of t-butyl methyl ether were then added to the mixture. The vial was capped and closed tightly. The mixture was stirred at 95° C. for 12 hours.

After cooling to room temperature, the mixture was passed through a pad of Celite® with ethyl acetate as the eluent to remove all the insoluble compounds. The resulting solution was concentrated, and the residual mixture was dissolved with a minimal amount of acetone and loaded onto a preparative TLC plate. The pure product was then isolated by preparative TLC with ethyl acetate and hexanes as the eluent.

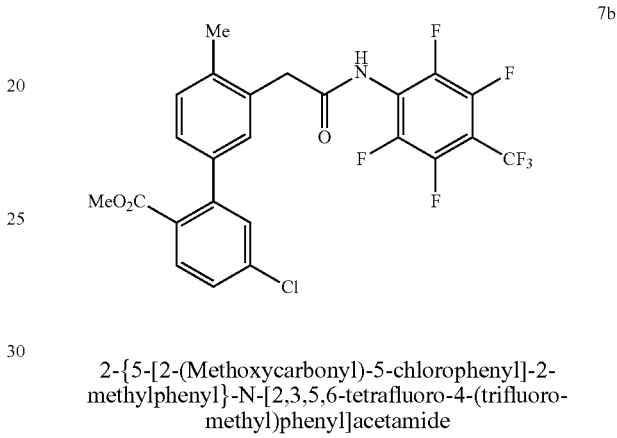

7a

2-{5-[2-(Methoxycarbonyl)phenyl]-2-methylphenyl}-N-[2,3,5,6-tetrafluoro-4-(trifluoromethyl)phenyl]-acetamide Preparative TLC using hexanes/EtOAc (4/1) as the eluent provided the pure product as a white solid (64% yield). $^1$H NMR (600 MHz, acetone-d$^6$) δ 9.54 (br, 1H, N—H), 7.75 (d, J=7.6 Hz, 1H), 7.59 (t, J=7.6 Hz, 1H), 7.46 (t, J=7.6 Hz, 1H), 7.44 (d, J=7.6 Hz, 1H), 7.30 (d, J=1.4 Hz, 1H), 7.27 (d, J=7.7 Hz, 1H), 7.17 (dd, J=7.7, 1.4 Hz, 1H), 3.97 (s, 2H), 3.60 (s, 3H), 2.41 (s, 3H); $^{13}$C NMR (150 MHz, acetone-d$^6$) δ 169.70, 169.43, 142.44, 139.82, 137.14, 134.19, 132.37, 132.01, 131.35, 131.26, 130.96, 130.31, 128.03, 127.96, 52.15, 41.17, 19.40. HRMS (ESI-TOF) m/z Calcd for $C_{24}H_{17}F_7NO_3^+$ [M+H]$^+$ 500.1091, found 500.1090.

2-{5-[2-(Methoxycarbonyl)-5-chlorophenyl]-2-methylphenyl}-N-[2,3,5,6-tetrafluoro-4-(trifluoromethyl)phenyl]acetamide Preparative TLC using hexanes/EtOAc (4/1) as the eluent provided the pure product as a white solid (45% yield). $^1$H NMR (400 MHz, acetone-d$^6$) δ 9.56 (br, 1H, N—H), 7.79 (d, J=8.4 Hz, 1H), 7.51 (dd, J=8.4, 2.0 Hz, 1H), 7.45 (d, J=2.0 Hz, 1H), 7.32 (d, J=2.0 Hz, 1H), 7.29 (d, J=8.0 Hz, 1H), 7.19 (dd, J=8.0, 2.0 Hz, 1H), 3.99 (s, 2H), 3.61 (s, 3H), 2.42 (s, 3H); $^{13}$C NMR (150 MHz, acetone-d$^6$) δ 169.34, 168.72, 144.53, 138.40, 137.87, 137.37, 134.43, 132.23, 131.19, 131.12, 131.08, 130.96, 128.02, 128.00, 52.37, 41.13, 19.42. HRMS (ESI-TOF) m/z Calcd for $C_{24}H_{16}ClF_7NO_3^+$ [M+H]$^+$ 534.0701, found 534.0694.

2-{5-[2-(Methoxycarbonyl)-4-methylphenyl]-2-methylphenyl}-N-[2,3,5,6-tetrafluoro-4-(trifluoromethyl)phenyl]acetamide Preparative TLC using hexanes/EtOAc (4/1) as the eluent provided the pure product as a white solid (66% yield). $^1$H NMR (400 MHz, acetone-d⁶) 9.51 (br, 1H, N—H), 7.55 (s, 1H), 7.41 (d, J=7.6 Hz, 1H), 7.31 (d, J=7.6 Hz, 1H), 7.27 (d, J=2.0 Hz, 1H), 7.24 (d, J=8.0 Hz, 1H), 7.14 (dd, J=8.0, 2.0 Hz, 1H), 3.96 (s, 2H), 3.60 (s, 3H), 2.41 (s, 3H), 2.40 (s, 3H); $^{13}$C NMR (150 MHz, acetone-d⁶) δ 169.81, 169.44, 139.78, 139.63, 137.81, 136.87, 134.11, 132.64, 132.19, 131.27, 131.23, 130.92, 130.74, 128.04, 52.09, 41.20, 20.83, 19.38. HRMS (ESI-TOF) m/z Calcd for $C_{25}H_{19}F_7NO_3^+$ [M+H]⁺ 514.1248, found 514.1250.

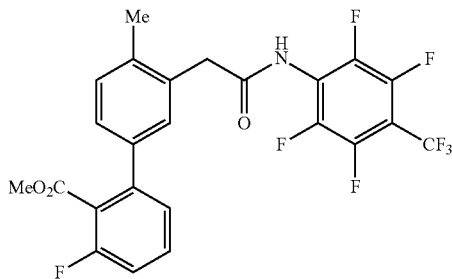

7d

2-{5-[2-(Methoxycarbonyl)-3-fluorophenyl]-2-methylphenyl}-N-[2,3,5,6-tetrafluoro-4-(trifluoro-methyl)phenyl]acetamide Preparative TLC using hexanes/EtOAc (4/1) as the eluent provided the pure product as a white solid (39% yield). $^1$H NMR (600 MHz, acetone-d⁶) δ 9.63 (br, 1H, N—H), 7.61-7.57 (m, 1H), 7.36 (d, J=1.8 Hz, 1H), 7.32-7.28 (m, 2H), 7.27-7.24 (m, 1H), 7.23 (dd, J=7.8, 1.8 Hz, 1H), 3.99 (s, 2H), 3.69 (s, 3H), 2.41 (s, 3H); $^{13}$C NMR (150 MHz, acetone-d⁶) 169.27, 166.44, 160.30 (d, J=247.5 Hz), 142.74 (d, J=3.0 Hz), 138.17, 137.81 (d, J=1.5 Hz), 134.84, 132.43 (d, J=9.0 Hz), 131.37, 130.98, 127.81, 126.46 (d, J=1.5 Hz), 122.55 (d, J=18.0 Hz), 115.14 (d, J=21.0 Hz), 52.72, 41.07, 19.42. HRMS (ESI-TOF) m/z Calcd for $C_{24}H_{16}F_8NO_3^+$ [M+H]⁺ 518.0997, found 518.0996.

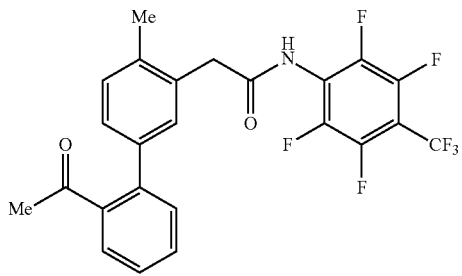

7e

2-[5-(2-Acetylphenyl)-2-methylphenyl]-N-[2,3,5,6-tetrafluoro-4-(trifluoromethyl)phenyl]acetamide Preparative TLC using hexanes/EtOAc (4/1) as the eluent provided the pure product as a white solid (48% yield). $^1$H NMR (400 MHz, CD₃CN) δ 7.58-7.52 (m, 2H), 7.47-7.40 (m, 2H), 7.30 (d, J=8.0 Hz, 1H), 7.23 (d, J=1.6 Hz, 1H), 7.18 (dd, J=8.0, 1.6 Hz, 1H), 3.86 (s, 2H), 2.38 (s, 3H), 2.10 (s, 3H); $^{13}$C NMR (150 MHz, CD₃CN) δ 204.80, 169.84, 141.67, 140.99, 139.69, 137.97, 134.71, 131.88, 131.77, 131.57, 131.31, 128.85, 128.74, 128.34, 41.13, 30.63, 19.41. HRMS (ESI-TOF) m/z Calcd for $C_{24}H_{17}F_7NO_2^+$ [M+H]⁺ 484.1142, found 484.1145.

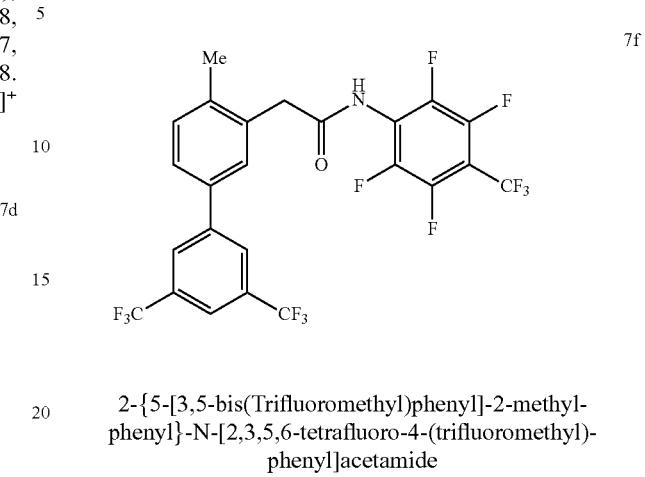

7f

2-{5-[3,5-bis(Trifluoromethyl)phenyl]-2-methylphenyl}-N-[2,3,5,6-tetrafluoro-4-(trifluoromethyl)phenyl]acetamide 6 Equivalents of ArI was used, and AgOAc was replaced by AgOPiv (3 eq.) in this reaction. Column chromatography using hexanes/EtOAc (4/1) as the eluent provided the pure product as a white solid (76% yield). $^1$H NMR (400 MHz, acetone-d⁶) δ 9.62 (br, 1H, N—H), 8.28 (s, 2H), 8.02 (s, 1H), 7.86 (d, J=2.0 Hz, 1H), 7.71 (dd, J=8.0, 2.0 Hz, 1H), 7.40 (d, J=8.0 Hz, 1H), 4.06 (s, 2H), 2.44 (s, 3H); $^{13}$C NMR (150 MHz, acetone-d⁶) δ 169.33, 144.09, 139.45, 136.35, 135.64, 132.65 (q, J=33.0 Hz), 132.08, 130.11, 127.93, 127.00, 124.54 (q, J=270.0 Hz), 121.43 (m), 41.20, 19.40. HRMS (ESI-TOF) m/z Calcd for $C_{24}H_{13}F_{13}NO^+$ [M+H]⁺ 578.0784, found 578.0785.

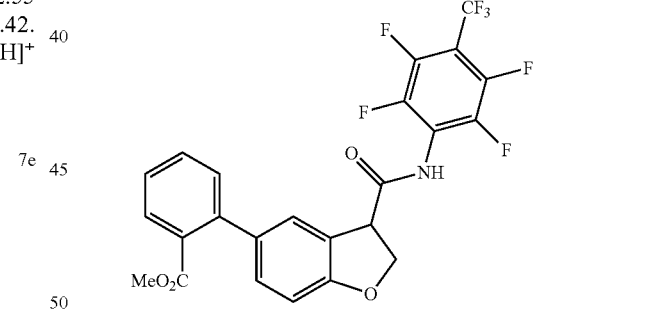

8

5-[2-(Methoxycarbonyl)phenyl]-N-[2,3,5,6-tetrafluoro-4-(trifluoromethyl)phenyl]-2,3-dihydro-benzofuran-3-carboxamide The general procedure for arylation was followed. 15 mol % of Pd(OAc)₂ and 30 mol % of ligand L19 were used in the reaction. Preparative TLC using hexanes/EtOAc (3/1) as the eluent provided the pure product as a white solid (82% yield). $^1$H NMR (600 MHz, CD₃CN) δ 8.79 (br, 1H, N—H), 7.73 (d, J=7.6 Hz, 1H), 7.56 (t, J=7.6 Hz, 1H), 7.42 (t, J=7.6 Hz, 1H), 7.38 (d, J=7.6 Hz, 1H), 7.35 (s, 1H), 7.17 (d, J=8.2 Hz, 1H), 6.87 (d, J=8.2 Hz, 1H), 4.93 (dd, J=5.9, 9.2 Hz, 1H), 4.80 (dd, J=9.2, 9.5 Hz, 1H), 4.61 (dd, J=5.9, 9.5 Hz, 1H), 3.61 (s, 3H); $^{13}$C NMR (150 MHz, CD₃CN) δ 170.59, 169.96, 160.70, 142.37, 134.76, 132.29, 132.20, 131.56, 130.90, 130.46, 128.06, 126.71, 125.80, 110.35, 74.60, 52.54, 49.20. HRMS (ESI-TOF) m/z Calcd for $C_{24}H_{15}F_7NC_4^+$ [M+H]$^+$ 514.0884, found 514.0884.

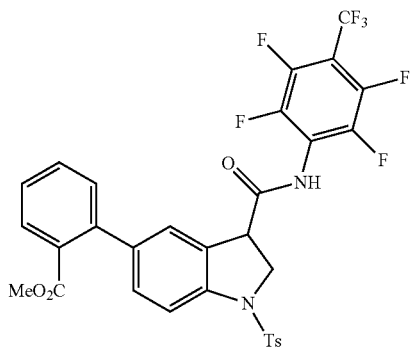

5-[2-(Methoxycarbonyl)phenyl]-N-[2,3,5,6-tetrafluoro-4-(trifluoromethyl)phenyl]-1-tosylindoline-3-carboxamide The general procedure for arylation was followed. 15 mol % of Pd(OAc)$_2$ and 30 mol % of ligand L19 were used in the reaction. Preparative TLC using hexanes/EtOAc (3/1) as the eluent provided the pure product as a white solid (69% yield). $^1$H NMR (400 MHz, CD$_3$CN) δ 8.76 (br, 1H, N—H), 7.80 (d, J=8.4 Hz, 2H), 7.75 (d, J=7.6 Hz, 1H), 7.61 (d, J=8.4 Hz, 1H), 7.56 (t, J=7.6 Hz, 1H), 7.44 (t, J=7.6 Hz, 1H), 7.36 (d, J=8.4 Hz, 2H), 7.34 (d, J=7.6 Hz, 1H), 7.27 (s, 1H), 7.23 (d, J=8.4 Hz, 1H), 4.39-4.30 (m, 2H), 4.24 (dd, J=9.2, 9.4 Hz, 1H), 3.55 (s, 3H), 2.38 (s, 3H); $^{13}$C NMR (150 MHz, CD$_3$CN) δ 169.85, 169.65, 146.14, 142.16, 141.89, 137.93, 134.35, 132.44, 132.01, 131.47, 130.87, 130.74, 130.64, 130.50, 128.53, 128.46, 125.94, 115.04, 53.62, 52.54, 47.01, 21.54. HRMS (ESI-TOF) m/z Calcd for $C_{31}H_{22}F_7N_2O_5S^+$ [M+H]$^+$ 667.1132, found 667.1133.

Formation and Characterization of the Benzocyclobutene Byproducts

When ligand L19 was used under the standard conditions excluding alkyl halides, the benzocyclobutene Compounds 2a and 2c can be obtained in very high yields after 3 hours.

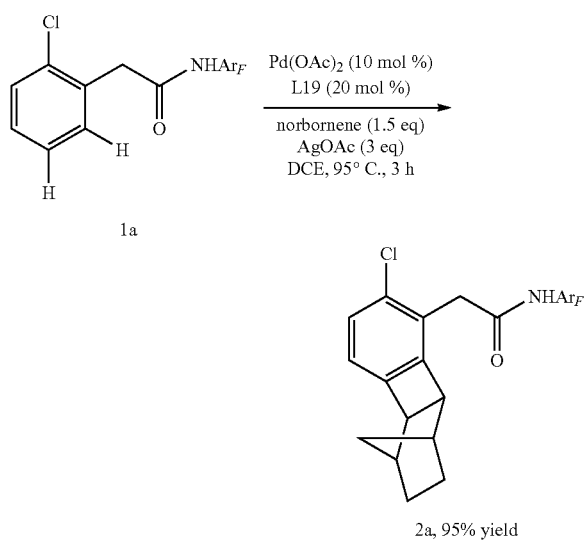

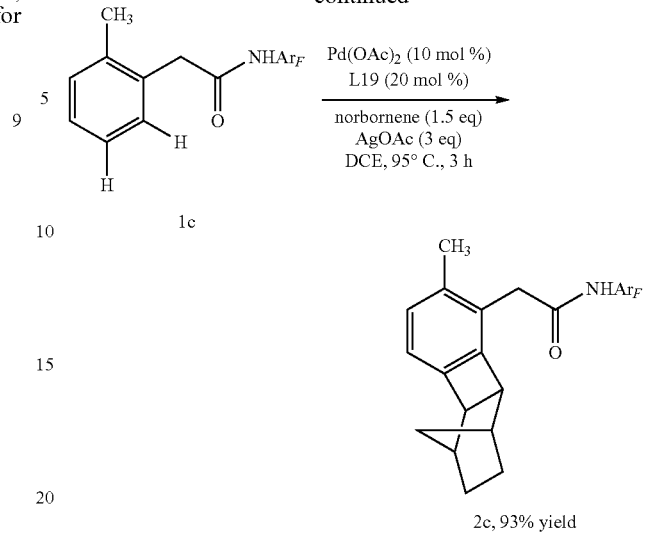

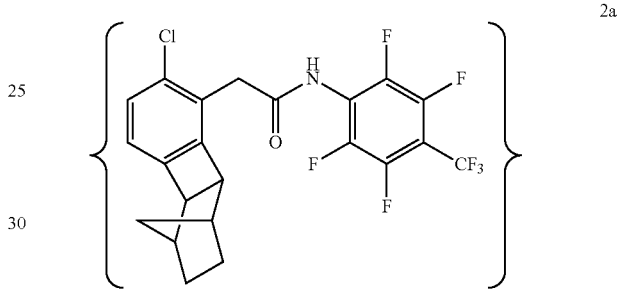

2-(6-Chloro-1,2,3,4,4a,8b-hexahydro-1,4-methanobiphenylen-5-yl)-N-[2,3,5,6-tetrafluoro-4-(trifluoromethyl)phenyl]acetamide $^1$H NMR (400 MHz, acetone-d$^6$) δ 9.64 (br, 1H, N—H), 7.28 (d, J=7.6 Hz, 1H), 6.97 (d, J=7.6 Hz, 1H), 3.97-3.91 (m, 2H), 3.25 (d, J=3.6 Hz, 1H), 3.13 (d, J=3.6 Hz, 1H), 2.37 (s, 1H), 2.26 (s, 1H), 1.63-1.57 (m, 2H), 1.22-1.17 (m, 2H), 0.98 (d, J=10.4 Hz, 1H), 0.90 (d, J=10.4 Hz, 1H); $^{13}$C NMR (150 MHz, acetone-d$^6$) δ 168.10, 148.43, 145.59, 133.67, 129.58, 128.43, 123.52, 50.13, 49.70, 37.21, 36.82, 36.45, 32.49, 28.32, 28.19. HRMS (ESI-TOF) m/z Calcd for $C_{22}H_{14}ClF_7NO^-$ [M–H]$^-$ 476.0658, found 476.0653.

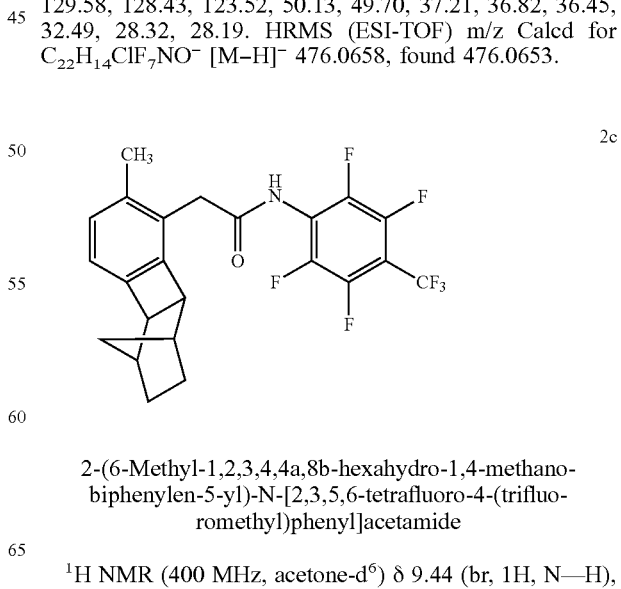

2-(6-Methyl-1,2,3,4,4a,8b-hexahydro-1,4-methanobiphenylen-5-yl)-N-[2,3,5,6-tetrafluoro-4-(trifluoromethyl)phenyl]acetamide $^1$H NMR (400 MHz, acetone-d$^6$) δ 9.44 (br, 1H, N—H), 7.04 (d, J=7.2 Hz, 1H), 6.81 (d, J=7.2 Hz, 1H), 3.84-3.76 (m, 2H), 3.19 (d, J=4.0 Hz, 1H), 3.07 (d, J=4.0 Hz, 1H), 2.33 (s, 1H), 2.32 (s, 3H), 2.21 (s, 1H), 1.60-1.54 (m, 2H), 1.20-1.12 (m, 2H), 0.93 (d, J=10.4 Hz, 1H), 0.88 (d, J=10.4 Hz, 1H); $^{13}$C NMR (150 MHz, acetone-d$^6$) δ 167.79, 145.43, 142.91, 135.19, 129.05, 127.07, 120.21, 48.57, 48.23, 35.95, 35.56, 34.88, 31.13, 27.06, 27.03, 18.47. HRMS (ESI-TOF) m/z Calcd for $C_{23}H_{17}F_7NO^-$ [M−H]$^-$ 456.1204, found 456.1205.

Confirmation of Product Structures

Aside from analyses of NMR spectra, the structures of the meta-C—H alkylation products were also confirmed by the comparison with two authentic samples prepared from commercially available 2,5-dimethylphenylacetic acid and 3,5-dimethylphenyl-acetic acid.

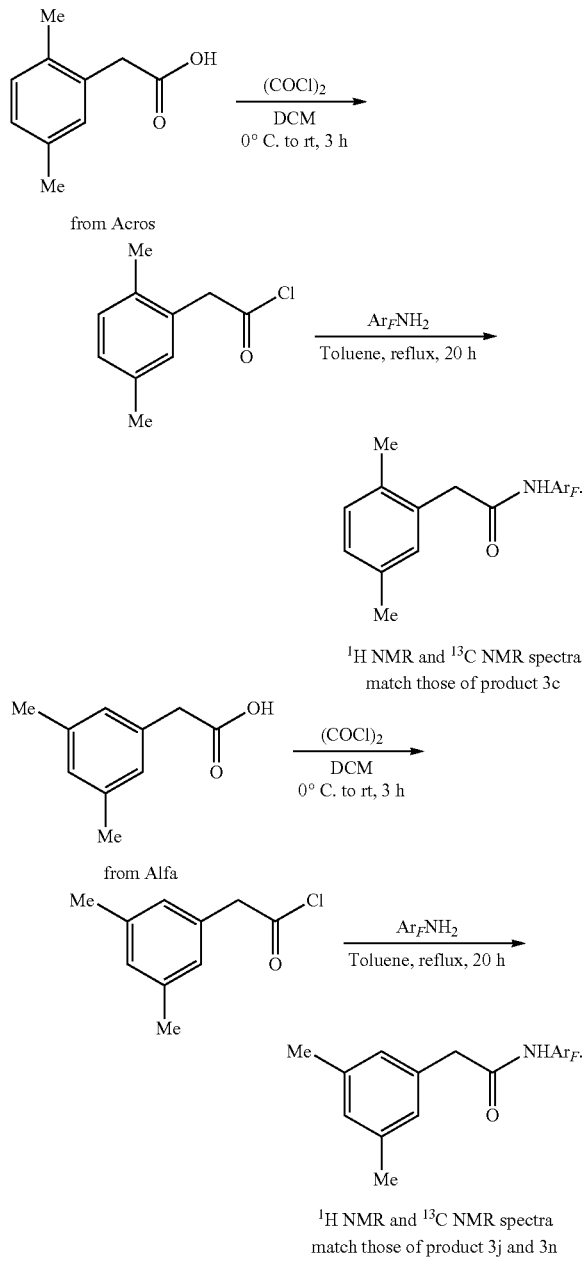

General Procedure for the Ligand-Enabled Norbornene-Mediated Meta-C—H Activation A 2-dram vial equipped with a magnetic stir bar was charged with N-nitrobenzylsulfonyl [Nos]-phenylalanine methyl ester substrates (0.10 mmol), Pd(OAc)$_2$ (2.2 mg, 10 mol %), 4-acetylpyridine (3.0 mg, 25 mol %), AgOAc (49.8 mg, 0.30 mmol) and norbornene (1.9 mg, 20 mol %). Methyl 2-iodobenzoate (37.5 μL, 0.25 mmol) was then added via a microsyringe. After 1.0 mL of TBME was injected, the vial was capped and closed tightly.

The reaction mixture was then stirred at 80° C. for 24 hours. After cooling to room temperature, the mixture was passed through a pad of Celite® with ethyl acetate as the eluent to remove all the insoluble materials. The resulting solution was concentrated, and the residual mixture was dissolved with a minimal amount of acetone and loaded onto a silica gel column or a preparative TLC plate. The pure product was then isolated by column chromatography or preparative TLC with ethyl acetate and hexanes (v/v, 1/2) as the eluent.

General Procedure for the Ligand-Enabled Norbornene-Mediated Meta-C—H Activation A 2-dram vial equipped with a magnetic stir bar was charged with 2-benzylpyridine (16.9 mg, 0.10 mmol) substrates (0.10 mmol), Pd(OAc)$_2$ (2.2 mg, 10 mol %), ligand L19 (3.0 mg, 20 mol %)), AgOAc (50 mg, 0.30 mmol) and norbornene (14.1 mg, 0.15 mmol). Methyl 2-iodobenzoate (43.0 μL, 0.30 mmol) was then added via a microsyringe. After 1.0 mL of DCE was injected, the vial was capped and closed tightly.

The reaction mixture was then stirred at 90° C. for 16 hours. After cooling to room temperature, the mixture was passed through a pad of Celite® with ethyl acetate as the eluent to remove all the insoluble materials. The resulting solution was concentrated, and the residual mixture was dissolved with a minimal amount of acetone and loaded onto a silica gel column or a preparative TLC plate. The pure product was then isolated by column chromatography or preparative TLC with ethyl acetate and hexanes as the eluent.

The invention claimed is:

1. A method of forming a carbon-to-carbon (C—C) bond at a position meta to a substituent previously present on the ring of an aromatic reactive substrate compound comprising the steps of
    a) providing a reaction mixture containing
        i) said aromatic reactive substrate compound of Formula I dissolved or dispersed in a non-aqueous polar solvent having a boiling point at 1 atmosphere of about 100° to about 200° C., that further contains dissolved or dispersed therein
        ii) a catalytic amount of a Pd(II) catalyst,
        iii) a catalytic amount of pyridine or a substituted pyridine ligand,
        iv) an ethylenically unsaturated bicyclic compound of Formula II as a transient mediator present in excess over the amount of reactive substrate,
        v) about 1.5 to about 5 equivalents of an oxidant based on the amount of said reactive substrate, and
        vi) about 1.1 to about 10 equivalents of a reactive coupling agent;
    b) heating said reaction mixture to a temperature of about 70° to about 120° C. and maintaining said temperature for a time period sufficient to carry out the C—C bond formation at a position meta to said substituent and form a reaction product;

wherein
said aromatic reactive substrate compound has a structural formula shown in Formula I, below:

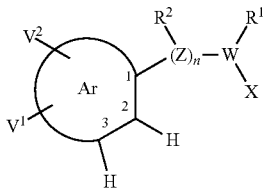

I wherein, the circled Ar is a carbocyclic aromatic ring structure in which the bond shown to Z is at the 1-position of the ring and the substituent bonded at the 1-position constitutes the substituent previously present on the ring, the ring position rotated clock-wise from the 1-position is the ortho-position at which a hydrogen (H) is bonded, and the next position clock-wise from the ortho-position at which another hydrogen (H) is bonded is the meta-position and is the position at which the new C—C bond is formed, said aromatic ring structure containing a single ring, or two or three fused rings in which one ring contains 6 ring atoms and the other one or two rings independently contain 6 or 5 ring atoms, n is one, —$ZR^2$— is —$CH_2$—, —CHY— or —$CHR^3$—, wherein Y is a protected hydroxyl or a protected amino group, and $R^3$ is a $C_1$-$C_{10}$-hydrocarbyl group that is straight, branched or includes a 4- to 6-membered ring bonded to a straight or branched chain, or $R^3$ together with the adjacent ring carbon atom, other than the ortho carbon noted above at the 2-position, and their associated atoms form a 5- or 6-membered aliphatic ring that can include one hetero atom in the ring that is O or protected N (nitrogen), W is C (carbon), a) W-X is a carbonyl group as discussed below, X is =O (oxo), $R^1$ is i) a perfluoro $C_1$-$C_{12}$-hydrocarbyl-amino group, $V^1$ and $V^2$ are the same or different substituents and are independently selected from the group consisting of hydrogen, halogen, a $C_1$-$C_6$-hydrocarbyl group, a perfluoro $C_1$-$C_6$-hydrocarbyl group and a $C_1$-$C_6$-hydrocarbyloxy group; and said transient mediator is an ethylenically unsaturated bicyclic compound of Formula II

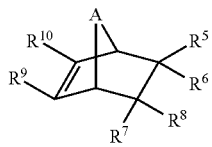

II wherein
A is $CH_2$, C=O or O,
each of $R^5$, $R^6$, $R^7$, $R^8$, $R^9$, and $R^{10}$ is independently H, $C_1$-$C_6$-hydrocarbyl, $C_1$-$C_6$-hydrocarbyloxy, $C_1$-$C_6$-hydrocarbyl carboxylate, $C_1$-$C_6$-hydrocarboyl, one or both of $R^5$ plus $R^6$ and $R^7$ plus $R^8$ together with the carbon atom to which they are bonded form one or two carbonyl groups, or one each of $R^5$ and $R^6$, or $R^7$ and $R^8$ together with the atoms to which they are bonded form a further 4- to 6-membered aliphatic or aromatic ring that itself can be independently substituted with one or two substituent groups selected from the group consisting of a $C_1$-$C_6$-hydrocarbyl, a $C_1$-$C_6$-hydrocarbyloxy, a $C_1$-$C_6$-hydrocarbyl carboxylate and a nitro group.

2. The method according to claim 1, wherein one or both of $V^1$ and $V^2$ are other than hydrido.

3. The method according to claim 1, wherein $R^1$ is a 4-$(CF_3)C_6F_4$NH— group.

4. The method according to claim 1, wherein —$ZR^2$— is —$CH_2$—.

5. The method according to claim 1, wherein —$ZR^2$— is —CHY—.

6. The method according to claim 1, wherein —$ZR^2$— is —$CHR^3$—.

7. The method according to claim 1, wherein W is nitrogen that is a ring atom of an aromatic ring system that contains at least one additional nitrogen atom that is adjacent to W in the aromatic ring.

8. The method according to claim 1, wherein W is the carbon of a >CH— group, X is a N-sulfonamido or N-carboxamido group, and $R^1$ is a $C_1$-$C_6$-hydrocarbyl carboxylate group.

9. The method according to claim 1, wherein W is C and W, X and $R^1$ together form a heteroaromatic ring structure that contains one ring or two fused rings that each contains 5- or 6-members and a total of one to four heteroatoms that are independently nitrogen, oxygen or sulfur.

10. The method according to claim 1, wherein said reactive coupling agent is an aromatic, benzylic or aliphatic bromide or iodide compound of the Formula $R^{15}$-Q, wherein $R^{15}$ is an aromatic group, a straight, branched or cyclic aliphatic $C_1$-$C_{10}$-hydrocarbyl group, or a benzylic group, and Q is bromo or iodo.

11. The method according to claim 1, wherein said transient mediator is norbornene.

12. The method according to claim 1, wherein said pyridine or a substituted pyridine ligand corresponds in structure to Formula L, below,

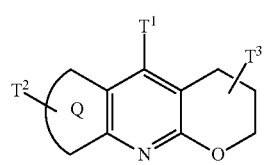

L wherein

Q is a 5- or 6-membered ring that is aliphatic or aromatic;

$T^1$ is hydrido, a $C_1$-$C_6$-hydrocarbyl group, a di-$C_1$-$C_6$-hydrocarbyl secondary amino group or the two hydrocarbyl groups along with the amine nitrogen atom forms a 5- or 6-membered ring that can contain an additional oxygen atom; and $T^2$ and $T^3$ are independently hydrido or the same or different $C_1$-$C_6$-hydrocarbyl group.

13. The method according to claim 1 further including the step of recovering said reaction product.

14. The method according to claim 12, wherein said pyridine or a substituted pyridine ligand corresponds in structure to a structural formula below,
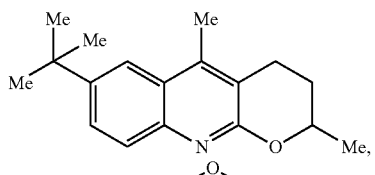
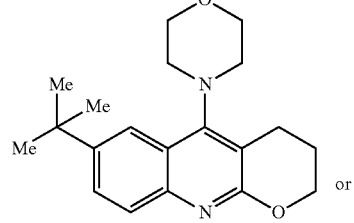
or
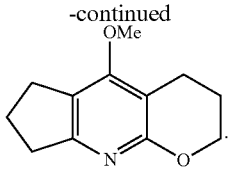
15. The method according to claim 12, wherein said pyridine or a substituted pyridine ligand corresponds in structure to the structural formula below,
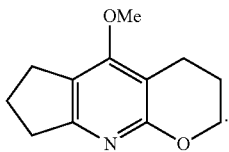 [SMILES: COc1c2c(nc3c1CCCO3)CCC2]
* * * * *